(12) United States Patent
Harris et al.

(10) Patent No.: US 12,383,626 B2
(45) Date of Patent: *Aug. 12, 2025

(54) POLYOXAZOLINE-DRUG CONJUGATES WITH NOVEL PHARMACOKINETIC PROPERTIES

(71) Applicant: Serina Therapeutics (AL), Inc., Huntsville, AL (US)

(72) Inventors: J Milton Harris, Huntsville, AL (US); Michael D Bentley, Huntsville, AL (US); Tacey X Viegas, Madison, AL (US); Randall W Moreadith, Huntsville, AL (US); Zhihao Fang, Madison, AL (US); Kunsang Yoon, Madison, AL (US); Rebecca Weimer, Huntsville, AL (US)

(73) Assignee: Serina Therapeutics (AL), Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/654,902

(22) Filed: May 3, 2024

(65) Prior Publication Data

US 2024/0293560 A1 Sep. 5, 2024

Related U.S. Application Data

(63) Continuation of application No. 17/621,613, filed as application No. PCT/US2020/040140 on Jun. 28, 2020.

(60) Provisional application No. 62/868,619, filed on Jun. 28, 2019.

(51) Int. Cl.
*A61K 47/59* (2017.01)
*A61K 31/05* (2006.01)

(52) U.S. Cl.
CPC .............. *A61K 47/59* (2017.08); *A61K 31/05* (2013.01)

(58) Field of Classification Search
CPC ....... A61K 47/56; A61K 47/59; A61K 47/595
See application file for complete search history.

(56) References Cited

U.S. PATENT DOCUMENTS

| | | | |
|---|---|---|---|
| 7,943,141 B2 | 5/2011 | Harris et al. | |
| 7,960,516 B2 * | 6/2011 | Matheus | C07K 16/2863 530/387.3 |
| 8,088,884 B2 | 1/2012 | Harris et al. | |
| 8,101,706 B2 | 1/2012 | Yoon et al. | |
| 8,110,651 B2 | 2/2012 | Yoon et al. | |
| 8,383,093 B1 | 2/2013 | Moreadith et al. | |
| 9,155,797 B2 | 10/2015 | Riggs-Sauthier et al. | |
| 2014/0112880 A1 | 4/2014 | Moreadith et al. | |
| 2014/0271527 A1 | 9/2014 | Moreadith et al. | |
| 2019/0134208 A1 | 5/2019 | Harris et al. | |

FOREIGN PATENT DOCUMENTS

| | | | |
|---|---|---|---|
| WO | 2009099670 | 8/2009 | |
| WO | 2012084060 | 6/2012 | |
| WO | WO-2013067199 A2 * | 5/2013 | ........... A61K 31/381 |
| WO | 2013084060 | 6/2013 | |
| WO | 2014087226 | 6/2014 | |
| WO | WO-2016147186 A1 * | 9/2016 | ........... A61K 31/352 |
| WO | 2020023947 | 1/2020 | |

OTHER PUBLICATIONS

Douillet et al (Journal of Crystal Growth , 2012, vol. 342, pp. 2-8) (Year: 2012).*
Thakuria and Thakur, Comprehensive Supramolecular Chemistry II, 2017, vol. 5, pp. 283-309 (Year: 2017).*
Moreadith et al (European Polymer Journal, 2017, vol. 88, pp. 524-552) (Year: 2017).*
Chang et al ('Lyophilized Biologics' in Lyophilized Biologics and Vaccines, 2015, Varshney and Singh, Eds, pp. 93-119) (Year: 2015).*
Harris et al (European Polymer Journal, 2019, vol. 120, article 109241) (Year: 2019).*
Anand et al (Brain Research Reviews, 2009, vol. 60, pp. 255-266) (Year: 2009).*
Conjos-Sanchez et al (Journal of controlled Release, 2015, vol. 198, pp. 80-90) (Year: 2015).*
Eskow Jaunarajs, Karen et al., Rotigotine Polyoxazoline Conjugate SER-214 Provides Robust and Sustained Antiparkinsonian Benefit, Movement Disorders, 2013 [retrieved on Aug. 27, 2020]. Retrieved from the Internet: <URL: https://onlinelibrary.wiley.com/doi/10.1002/mds.25625>, entire document; pp. 1675-1682.
International Search Report dated Nov. 16, 2020 of International Patent Application No. PCT/US2020/040140.
Extended European Search Report dated Dec. 4, 2023 of corresponding European Patent Application No. 20830744.7.

(Continued)

*Primary Examiner* — Karen A. Canella
(74) *Attorney, Agent, or Firm* — Bradley Arant Boult Cummings LLP

(57) ABSTRACT

Polyoxazoline (POZ) conjugates wherein the conformation of the POZ conjugate and the release rate of an agent from the POZ conjugate can be controlled by selecting one or more characteristics of the POZ polymer and methods of controlling the conformation of a POZ conjugate and the release rate of an agent prior are provided as well as methods of treatment using such POZ conjugates and methods. Pharmaceutical compositions including a POZ conjugate are also provided.

20 Claims, 7 Drawing Sheets

(56) References Cited

OTHER PUBLICATIONS

Mero et al., Journal of Controlled Release, Elsevier "Synthesis and Characterization of poly(2-ethyl 2-oxazoline)-conjugates with proteins and drugs: Suitable alternatives to PEG-conjugates?", Oct. 22, 2007, vol. 125, No. 2, pp. 87-95.
Supplementary European Search Report dated Jul. 26, 2023 of corresponding European Patent Application No. 20830744.7.
Non-Final Office Action dated Jun. 11, 2024 of corresponding U.S. Appl. No. 17/621,613.
Decision of Rejection dated Nov. 27, 2024 of corresponding Chinese Patent Application No. 202080060438.2.

* cited by examiner

Rotigotine

Buprenorphine

Dexanabinol

Cannabidiol d9-tetrahydrocannabinol

Cannabigerol

POLYOXAZOLINE-DRUG CONJUGATES WITH NOVEL PHARMACOKINETIC PROPERTIES

CROSS-REFERENCE TO RELATED APPLICATIONS

This application is a continuation of U.S. patent application Ser. No. 17/621,613, filed Dec. 21, 2021, which is a national stage entry of International Application No. PCT/US2020/040140, filed Jun. 28, 2020, which claims priority to U.S. Provisional Patent Application No. 62/868,619, filed Jun. 28, 2019, the entire disclosures of which are incorporated herein.

BACKGROUND

Use of polymer conjugates (for example, polyoxazolines (POZ) conjugates) for drug modification and drug delivery has attracted increasing research activity in recent years. One aspect of this research involves attachment of drugs as pendent groups along the polymer backbone, where the drugs can be released from the polymer backbone after administration to a subject. The rate at which such drugs are released from the polymer backbone is variable. The Applicant has previously described the slow release of pendant rotigotine from POZ conjugates (linked via triazole-ester linkages), resulting in a near linear pharmacokinetic (PK) profile suitable for once-a-week subcutaneous injection of POZ-rotigotine conjugates in humans. However, the rate of release of various drugs from POZ polymers has been reported to be variable.

The ability to control the release rate of an agent from a polymer conjugate is therapeutically useful. For example, the slow/sustained release of an agent from a polymer conjugate may reduce local adverse effects, reduce adverse effects associated with peak blood levels, or extend the half-life of an agent. Such a sustained release is also associated with the added advantages of convenience of dosing, improved compliance, and less fluctuation in blood levels during administration. Likewise, the fast/immediate release of an agent from a polymer conjugate is useful in achieving high concentrations of the agent in the body over a short period of time.

The prior art is in need of solutions to control the release rate of an agent (for example a drug) from POZ conjugates. Furthermore, the prior art is in need of solutions to provide a desired release profile of an agent from a POZ conjugate (such as a sustained release profile). The present disclosure provides a solution to these problems.

Red italic numbers correspond to $^1$H while blue numbers in regular font are the assigned $^{13}$C chemical shifts.

Figure 3:
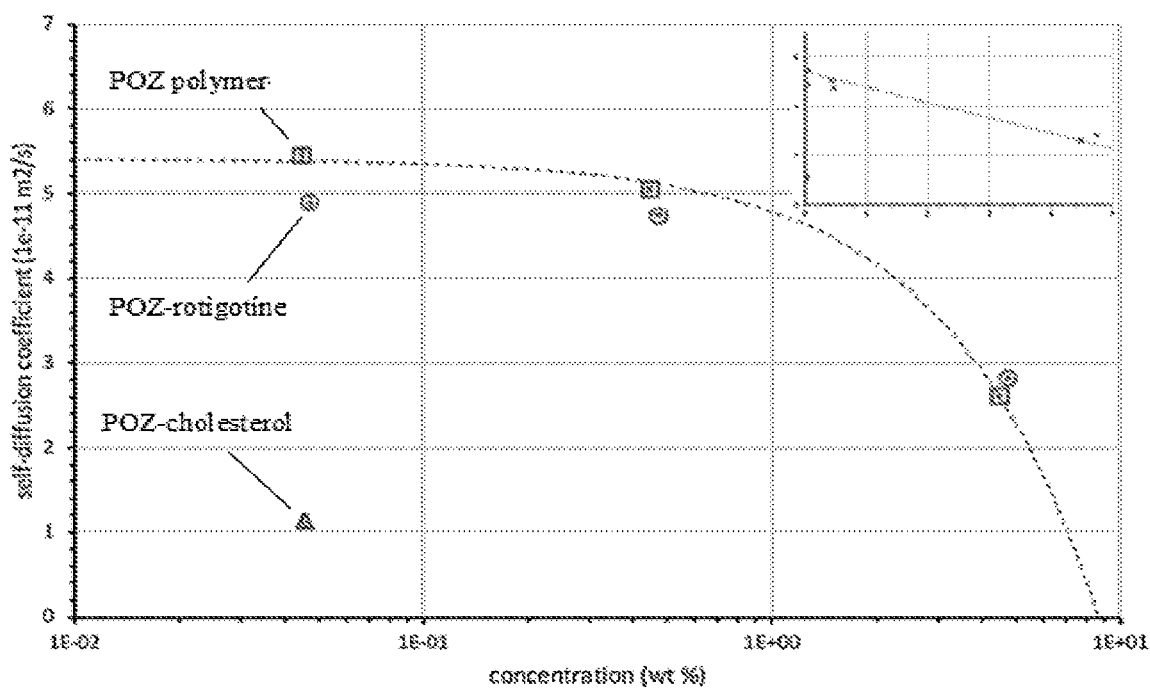

FIG. 3 shows self-diffusion coefficients of pure POZ (□), POZ-rotigotine (○), and POZ-cholesterol (Δ). Dashed line shows linearity of POZ diffusion due to obstruction. Insert provides identical data on linear scale.

Figure 4:
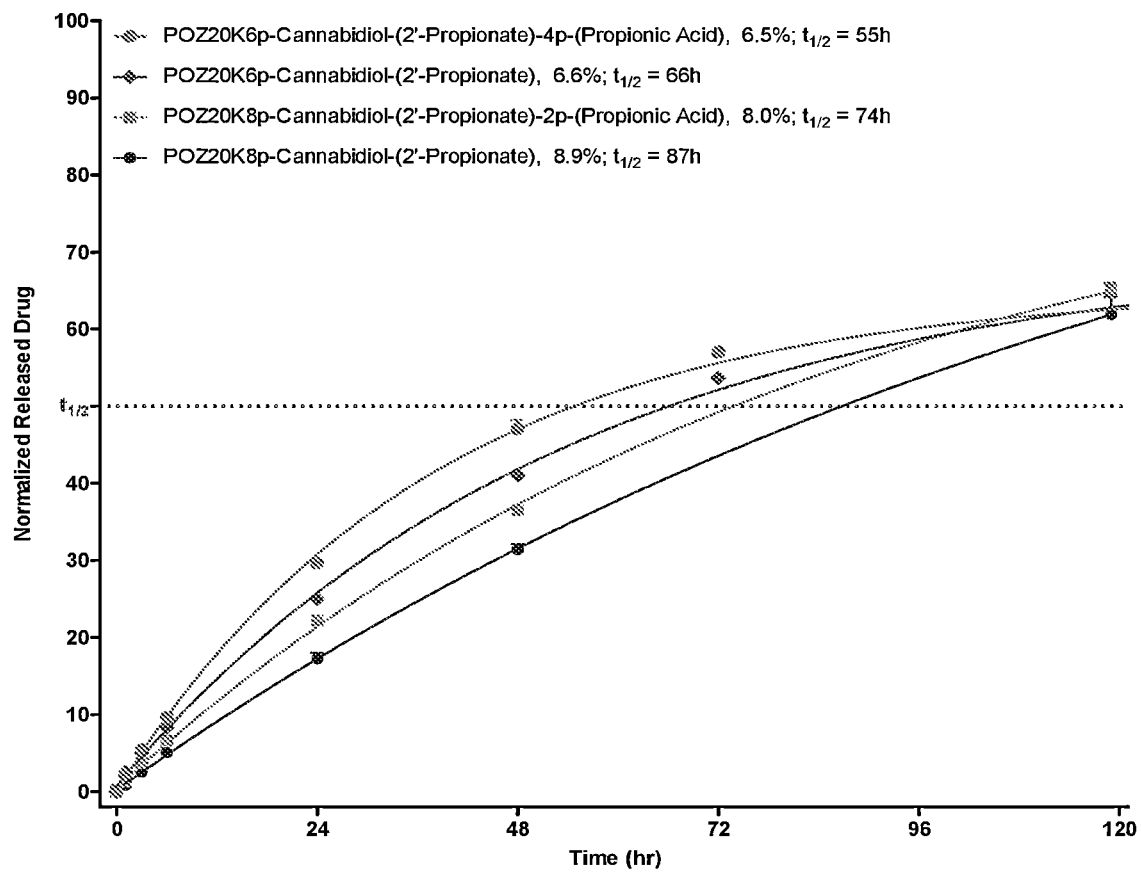

FIG. 4 shows the hydrolysis rates of POZ-CBD conjugates in female human plasma at 37° C.

Figure 5:
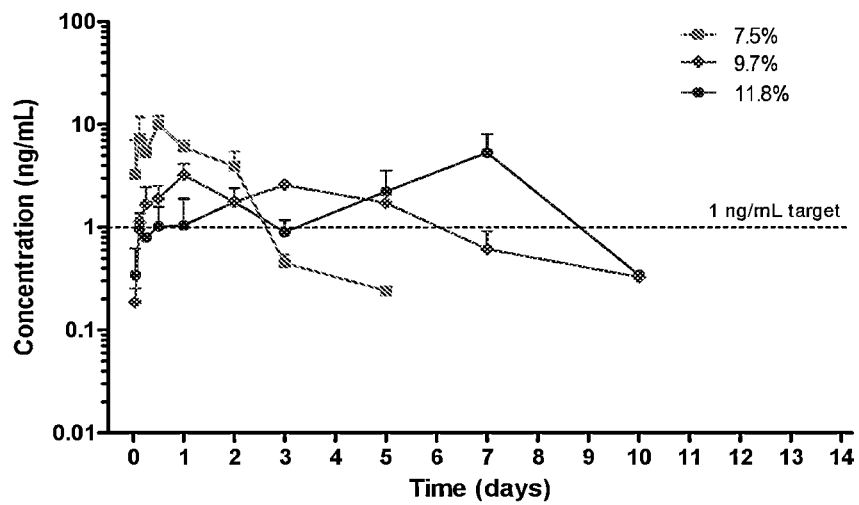

FIG. 5 shows a pharmacokinetic profile of rotigotine following a single SC injection of POZ-ROT conjugates to male monkeys at a dose of 1.5 mg/kg. Drug loading of 7.5% (□), 9.7% (Δ) and 11.8 (○). n=3±SD.

Figure 6:
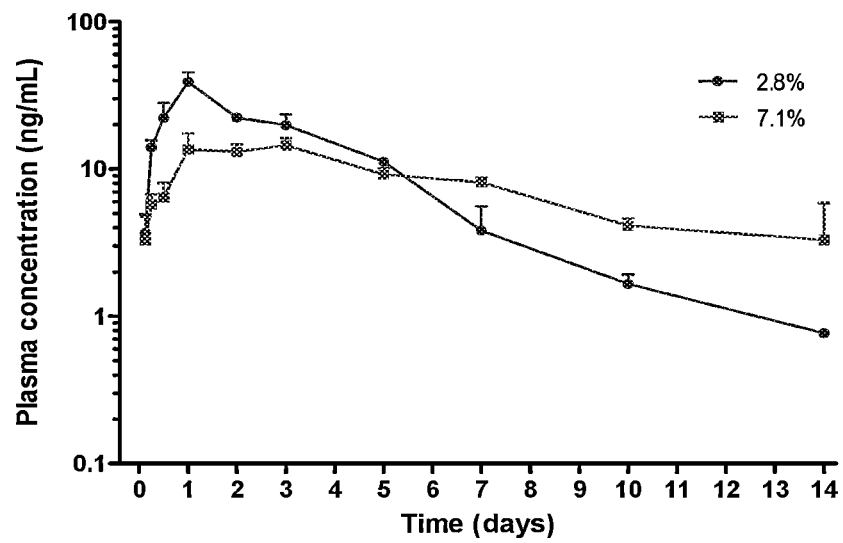

FIG. 6 shows a pharmacokinetic profile of cannabidiol following a single SC injection of POZ-CBD conjugate to male monkeys at a dose of 4.5 mg/kg. Drug loading of 2.8% (○) and 7.1% (□). n=3±SD.

Figure 7:
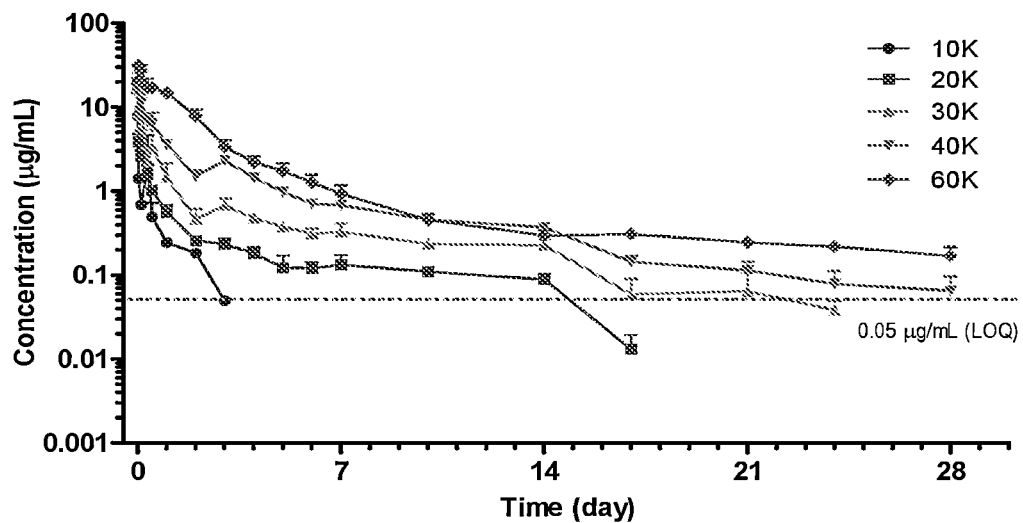

FIG. 7 shows the plasma concentrations of POZ cyanine 5 conjugates of different molecular weights after intravenous injection to rats at a dose of 10 mg/kg. The molecular weights tested are 10K (●), 20K (■), 30K (▲), 40K (▼) and 60K (♦). n=3±SD.

Figure 8:
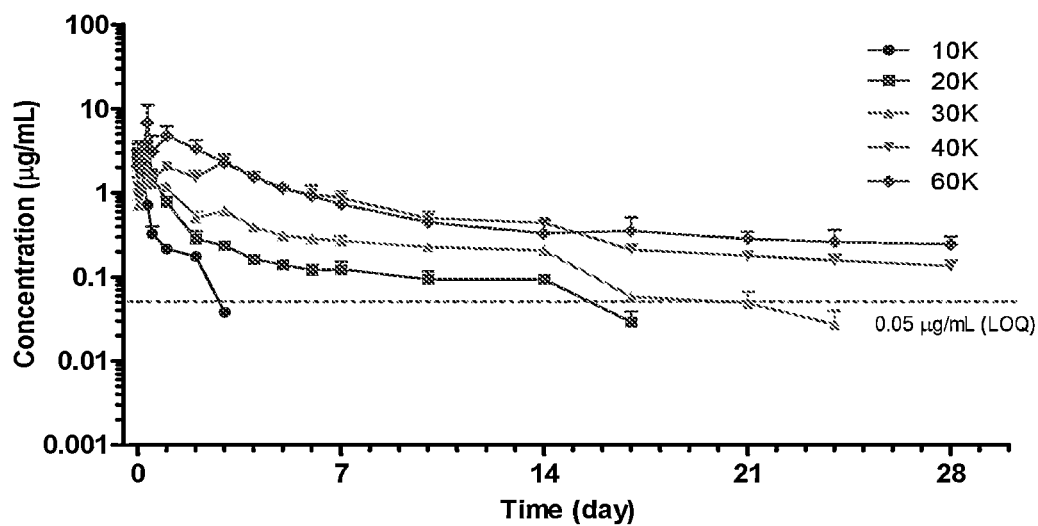

FIG. 8 shows the plasma concentrations of POZ cyanine 5 conjugates of different molecular weights after subcutaneous injection to rats at a dose of 10 mg/kg. The molecular weights tested are 10K (●), 20K (■), 30K (▲), 40K (▼) and 60K (♦). n=3±SD.

Figure 9:
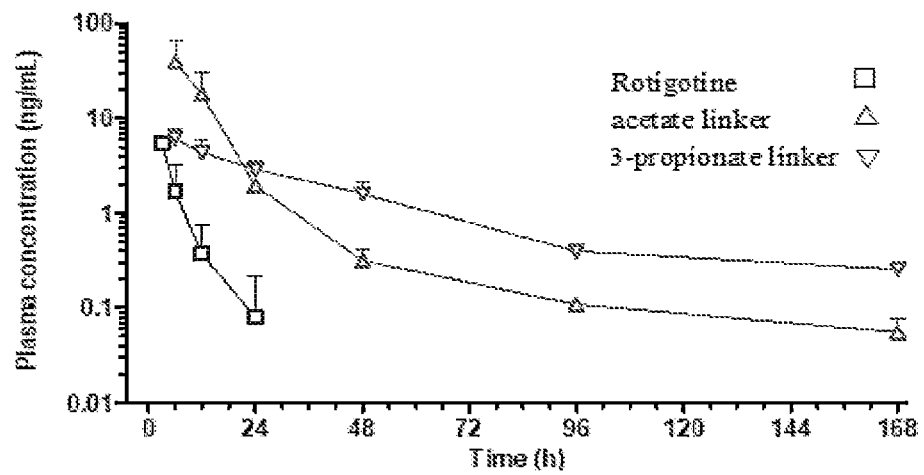

FIG. 9 shows a pharmacokinetic profile of rotigotine following a single SC injection of rotigotine and POZ-ROT conjugate to male rats. Rotigotine, dose 0.5 mg/kg (□), acetate linker, loading 10.9%, dose 1.6 mg/kg (Δ), and 3-propionate linker, loading 13.3%, dose 1.6 mg/kg (∇). n=3 SD.

Figure 10:
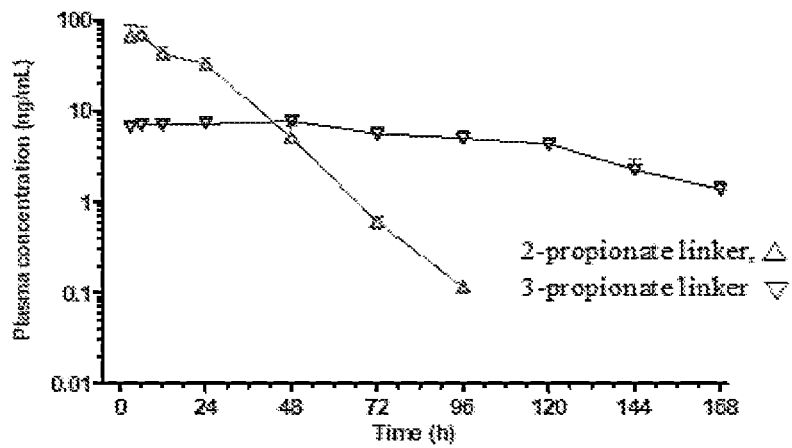

FIG. 10 shows a pharmacokinetic profile of buprenorphine following a single SC injection of POZ-BUP conjugate to male monkeys. 2-propionate linker, drug loading 11.2%, dose 1.5 mg/kg (Δ), and 3-propionate linker, drug loading 13.3%, dose 1.5 mg/kg (∇). n=3±SD.

SUMMARY

The present disclosure provides POZ conjugates that modulate the conformation of the POZ conjugate. As such, the present disclosure provides for a POZ conjugate and a method to control the conformation of a POZ conjugate. In addition, the present disclosure provides for a POZ conjugate and a method to modulate the release of the agent from the POZ conjugate. Furthermore, the present disclosure provides for a POZ conjugate and a method to allow the selection of a release profile of the agent from the POZ conjugate. Still further, the present disclosure provides compositions, including pharmaceutical compositions, comprising such POZ polymer conjugates. Methods of treatment using the described POZ conjugates, methods, and pharmaceutical compositions are also provided.

In a general form, the POZ conjugates of the present disclosure comprise a POZ polymer portion and an agent. The agent is linked to the POZ polymer through a physiologically degradable linkage (i.e., a linkage between the agent and the POZ polymer). Cleavage of the physiologically degradable linker may be controlled by altering the conformation of the POZ conjugate to increase or decrease access of a cleaving function (for example, an enzyme) to the physiologically degradable linker.

The conformation of the POZ conjugate may be controlled in several ways as described herein. For example, the conformation of the POZ conjugate may be controlled through the selection of a POZ polymer characteristic, through the selection of an agent characteristic, through the selection of a loading characteristic, or combinations of the foregoing.

DETAILED DESCRIPTION

Introduction

The POZ conjugates of the present disclosure comprise a POZ polymer portion and an agent. The agent is linked to the POZ polymer through a physiologically degradable linkage. Cleavage of the physiologically degradable linker may be controlled by altering the conformation of the POZ conjugate to increase or decrease access of a cleaving function to the physiologically degradable linker.

The factors that control the release rate of an agent from a POZ conjugate are not fully understood. In previous work, the Applicant has shown the manner in which an agent is linked to the POZ polymer portion of the POZ conjugate can influence the release rate of the agent from the POZ conjugate. Specifically, when rotigotine (i.e., the agent) was linked in a pendant position along the polymer backbone of a 20K POZ polymer through a degradable triazine-alkyl ester linkage (i.e., a physiologically degradable linkage), the hydrolysis rate varied depending on the structure of the linkage (see Structure 1 below, where R* is H, R** is —CH$_2$CH$_3$, a is random, n is typically 190, o is typically 10, and p can be varied to vary hydrolysis rate).

Structure 1

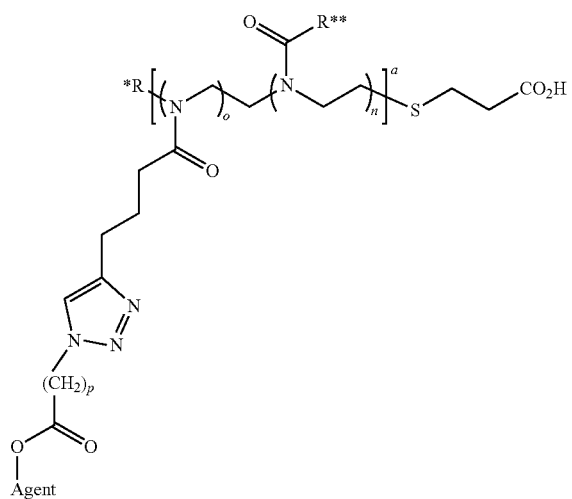

In further investigation of the observed differences in the release rate of the agent, the Applicant unexpectedly discovered that the conformation of the POZ conjugate impacted the release rate of the agent from the POZ conjugate.

While not being bound to any particular theory, it is believed that the water soluble POZ polymer portion of the POZ conjugate folds loosely around the agent to form a shell around the agent. The surrounding POZ polymer shell is flexible and mobile and has the ability to interfere, but not prevent, access of the required cleaving function (for example an enzyme, such as an esterase) to the physiologically degradable linker. This interference with the approach of the cleaving function slows cleavage of the physiologically degradable linker and therefore slows the release rate of the agent from the POZ conjugate. When the POZ polymer shell surrounds the agent, the POZ conjugate is in a compact conformation.

The flexibility and mobility of the POZ polymer shell is dependent, at least in part, on one or more properties of the POZ conjugate. As such, the release rate of the agent from the POZ conjugate can be controlled by selecting one or more characteristics of the POZ conjugate. Such characteristics include, but are not limited to, a POZ polymer characteristic, an agent characteristic, a loading characteristic, or a combination of the foregoing.

In one embodiment, an agent characteristic (i.e., the nature of the agent) influences the release rate of an agent from the POZ conjugate. Consider two POZ conjugates of the Structure 1 above. In the first POZ conjugate, R* is H, R** is —CH$_2$CH$_3$, a is random, n is 190, o is 10, p is 3, and the agent has a Log P of 7.0. In the second POZ conjugate, the values are the same except the agent has a Log P of 2.5 (less hydrophobic). In the first POZ conjugate, the POZ polymer shell is less flexible and mobile (i.e., is it wrapped tighter around the agent and/or core) as compared to the second POZ conjugate as the hydrophilic POZ polymer portion interacts with the more hydrophobic agent. In this situation, the POZ polymer shell of the first POZ conjugate restricts access of the cleaving function to the physiologically degradable linker to a greater extent than in the second POZ conjugate and the release rate of the agent from the first POZ conjugate is slower than the release rate of the agent from the second POZ conjugate.

In another embodiment, a POZ polymer characteristic (i.e., the size of the POZ polymer portion) influences the release rate of an agent from the POZ conjugate. Consider two POZ conjugates of Structure 1. In the first POZ conjugate, R* is H, R** is —CH$_2$CH$_3$, a is random, n is 390, o is 10, p is 3, and the agent has a Log P of 6.1. In the second POZ conjugate, the values are the same except for n, which in the second POZ conjugate is 190. In the first POZ conjugate, the POZ polymer shell is less flexible and mobile and/or more completely surrounds the agent and/or core as compared to the second POZ conjugate due to the increased molecular weight of the first POZ conjugate. In this situation, the POZ polymer shell of the first POZ conjugate restricts access of the cleaving function to the physiologically degradable linker to a greater extent than in the second POZ conjugate and the release rate of the agent from the first POZ conjugate is slower than the release rate of the agent from the second POZ conjugate.

In another embodiment, a loading characteristic (i.e., the loading percentage) influences the release rate of an agent from the POZ conjugate. Consider two POZ conjugates of Structure 1. In the first POZ conjugate, R* is H, R** is —CH$_2$CH$_3$, a is random, n is 190, o is 15, p is 3, and the agent has a Log P of 4.9. In the second POZ conjugate, the values are the same except for o, which in the second POZ conjugate is 5. In the first POZ conjugate, the POZ polymer shell is less flexible and mobile (i.e., is it wrapped tighter around the agent and/or core) as compared to the second POZ conjugate due to the increased number of agents available to interact with the POZ polymer forming the shell. In this situation, the POZ polymer shell of the first POZ conjugate restricts access of the cleaving function to the physiologically degradable linker to a greater extent than in the second POZ conjugate and the release rate of the agent from the first POZ conjugate is slower than the release rate of the agent from the second POZ conjugate. In certain embodiments, the greater the hydrophobic character of the agent, the greater the impact of the loading percentage in stimulating the formation of the compact conformation.

In another embodiment, a different POZ polymer characteristic (i.e., the nature of the pendent groups on the POZ polymer portion of the POZ conjugate) influences the release rate of an agent from the POZ conjugate. Consider two POZ conjugates of Structure 1. In the first POZ conjugate, R* is H, R** is —CH$_2$CH$_3$, a is random, n is 190, o is 6, p is 3, and the agent has a Log P of 6.1. In the second POZ conjugate R* is H, R** is 70% —CH$_2$CH$_3$ and 30%

—CH₃, a is random, n is 190, o is 6, p is 3, and the agent has a Log P of 6.1. The second POZ conjugate contains 30% —CH₃ groups, which are less hydrophobic than the —CH₂CH₃ groups on the first POZ conjugate. In the first POZ conjugate, the POZ polymer shell is less flexible and mobile (i.e., it is wrapped tighter around the agent and/or core) as compared to the second POZ conjugate due to the increased hydrophobic character of the POZ polymer portion. In this situation, the POZ polymer shell of the first POZ conjugate restricts access of the cleaving function to the physiologically degradable linker to a greater extent than in the second POZ conjugate and the release rate of the agent from the first POZ conjugate is slower than the release rate of the agent from the second POZ conjugate.

In another embodiment, a different POZ polymer characteristic (i.e., the presence of a hydrophilic or hydrophobic pendent moiety on the POZ polymer portion of the POZ conjugate) influences the release rate of an agent from the POZ conjugate. Consider two POZ conjugates, the first of Structure 1 and the second of Structure 2 below. In the first POZ conjugate, R* is H, R** is —CH₂CH₃, a is random, n is 190, o is 6, p is 3, and the agent has a Log P of 6.1. In the second POZ conjugate (Structure 2), R* is H, R is —CH₂CH₃, R* is a linked propionic acid, a is random, n is 190, o is 6, m is 4, and the agent has a Log P of 6.1. The second POZ conjugate contains in addition to the 190 —CH₂CH₃ pendant groups present on the first POZ conjugate, 4 propionic acid pendant moieties (which are hydrophilic due, at least in part, to the C—O bond). Without being bound to any particular theory, the 4 pendant hydrophilic moieties attract water to the area near the backbone of the POZ polymer portion (the core) and prevent the POZ polymer shell from wrapping around the agent and/or the core to the same extent as when the hydrophilic pendent moieties are absent (resulting in the POZ polymer shell being more flexible and mobile in the second POZ conjugate). In this situation, the POZ polymer shell of the first POZ conjugate restricts access of the cleaving function to the physiologically degradable linker to a greater extent than in the second POZ conjugate and the release rate of the agent from the first POZ conjugate is slower than the release rate of the agent from the second POZ conjugate.

Structure 1

Therefore, the conformation of the POZ conjugate is a factor that influences the conformation and/or release rate of an agent from a POZ conjugate. Through modification of the conformation of the POZ conjugate, the release rate of the agent from the POZ conjugate may be modulated. For example, if the compact conformation of the POZ conjugate is inhibited, the release rate of the agent from the POZ conjugate is increased (relative to a POZ conjugate where the compact conformation is not inhibited). Conversely, if the compact conformation of the POZ conjugate is stimulated, the release rate of the agent from the POZ conjugate is decreased (relative to a POZ conjugate where the compact conformation is not stimulated).

The present disclosure provides POZ conjugates and methods for controlling the conformation of the POZ conjugate by modulating a POZ conjugate characteristic. The present disclosure further provides for a POZ conjugate and a method to modulate the release of the agent from the POZ conjugate by modulating a POZ conjugate characteristic. The present disclosure also further provides POZ conjugates and methods for modulating (i.e., selecting or tuning) a release rate (i.e., a release profile) of an agent from a POZ conjugate by modulating a POZ conjugate characteristic. In certain embodiments of this method, a release rate/release profile of the agent may be selected. The present disclosure further provides POZ conjugates and methods for selecting a release profile of an agent from a POZ conjugate by modulating a POZ conjugate characteristic. Still further, the present disclosure provides compositions, including pharmaceutical compositions, comprising such POZ polymer conjugates. Methods of treatment using the described POZ conjugates, methods, and pharmaceutical compositions are also provided.

Definitions

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

The articles "a" and "an" are used herein to refer to one or to more than one (i.e., to at least one) of the grammatical object of the article. By way of example, "an element" means one element or more than one element.

As used herein, the term "active" or "activated" when used in conjunction with a particular functional group refers to a functional group that reacts readily with an electrophile or a nucleophile on another molecule. This is in contrast to those groups that require catalysts or impractical reaction conditions in order to react (i.e., a "non-reactive" or "inert" group).

As used herein, the term "agent" refers to any molecule having a therapeutic or diagnostic application, wherein the agent is capable of being linked to a group on a POZ polymer or a linking group attached to a POZ polymer. The agent includes, but is not limited to, a therapeutic agent (such as but not limited to a drug), a diagnostic agent, and an organic small molecule. In certain embodiments, an agent is hydrophobic or an agent is not soluble in water (for example, a hydrophobic drug). In certain embodiments, an agent has a log P value ≥0.5 or ≥2.0.

As used herein, the term "physiologically degradable" or "physiologically releasable" refers to a linkage containing a cleavable moiety. The terms degradable and releasable do not imply any particular mechanism by which the linker is cleaved.

As used herein, the term "cleavable moiety" refers to a group that is cleavable in a subject in vivo under physiological conditions in the subject (for example, after a POZ conjugate of the present disclosure has been administered to the subject). In one embodiment, the cleavable moiety is cleaved by a chemical reaction. In aspect of this embodiment, the cleavage is by reduction of an easily reduced group in the cleavable moiety, such as, but not limited to, a disulfide. In another aspect of this embodiment, the cleavable moiety is cleaved through hydrolysis (i.e., a reaction with water). In one embodiment, the cleavable moiety is cleaved by a substance that is naturally present or induced to be present in the subject. In an aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing.

As used herein, the terms "electrophile" and "electrophilic group" refer to an ion, atom or collection of atoms that may be ionic, having an electrophilic center, i.e., a center that is electron seeking, capable of reacting with a nucleophile.

As used herein, the phrase "inhibits the formation of the compact conformation" when referring to a POZ conjugate does not mean that the water soluble POZ polymer portion of the POZ conjugate is prevented completely from folding around the agent and/or the core, but means that the water soluble POZ polymer portion of the POZ conjugate folds to a lesser extent around the agent and/or the core (i.e., form a looser shell), for example as compared to a Reference POZ Conjugate or a POZ conjugate containing a different modification (for example, a less hydrophobic pendent moiety).

As used herein, the term "link", "linked" "linkage" or "linker" when used with respect to a POZ polymer, POZ conjugate, an agent, or compound described herein, or components thereof, refers to bonds that normally are formed as the result of a chemical reaction and typically are covalent linkages.

As used herein, the term "hydrophilic", for example with reference to a hydrophilic portion, refers to a compound or molecule, or a portion thereof, where the interaction with water is thermodynamically more favorable than interaction with oil or other hydrophobic solvents. A hydrophilic compound is able to dissolve in, or be dispersed in, water. Typically, a hydrophilic compound contains one or more oxygen, nitrogen, sulfur, and/or phosphorous atoms and/or one or more polar covalent bonds (such as, but not limited to, $C=O$, $C-N$, $C\equiv N$, $O-H$, and/or C-halogen bonds). Such polar covalent bonds may be arranged asymmetrically.

As used herein, the term "hydrophobic", for example with reference to a hydrophobic portion, refers to a compound or molecule, or a portion thereof, where the interaction with water is thermodynamically less favorable than interaction with oil or other hydrophobic solvents. A hydrophobic compound is able to dissolve in, or be dispersed in, oil or other hydrophobic solvents.

As used herein, the term "inert" or "non-reactive" when used in conjunction with a particular functional group refers to a functional group that does not react readily with an electrophile or a nucleophile on another molecule and require catalysts or impractical reaction conditions in order to react.

As used herein, the terms "nucleophile" and "nucleophilic group" refers to an ion, atom or collection of atoms that may be ionic having a nucleophilic center, i.e., a center that is capable of donating electrons and reacting with an electrophile.

As used herein, the term "pendent group" refers to a part of the POZ polymer portion that is formed during the polymerization of the POZ polymer portion; a pendent group is exemplified by X of formula I as described herein.

As used herein, the term "pendent moiety" refers to a substituent that is linked to the POZ polymer portion via a linking group; a pendent moiety is exemplified by $R_1$ of formula I as described herein.

As used herein, the term "pharmaceutically acceptable" refers to a compound that is compatible with the other ingredients of a composition and not deleterious to the subject receiving the compound or composition. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "pharmaceutically acceptable form" is meant to include known forms of a compound or POZ conjugate that may be administered to a subject, including, but not limited to, solvates, hydrates, prodrugs, isomorphs, polymorphs, pseudomorphs, neutral forms and salt forms of a compound. In certain embodiments, the pharmaceutically acceptable form excludes prodrugs, isomorphs and/or pseudomorphs. In certain embodiments, the pharmaceutically acceptable form is limited to pharmaceutically acceptable salts, neutral forms, solvates and hydrates. In certain embodiments, the pharmaceutically acceptable form is limited to pharmaceutically acceptable salts and neutral forms. In certain embodiments, the pharmaceutically acceptable form is limited to pharmaceutically acceptable salts.

As used herein, the term "polar covalent bond" is a covalent bond in which one of the atoms has a higher affinity for electrons (i.e., is more electronegative) than the other atom.

As used herein, the term "reference POZ conjugate" means a POZ conjugate that has not been modified (i.e., by altering a POZ polymer characteristic, an agent characteristic, and/or a loading characteristic) to inhibit or stimulate the formation of the compact conformation but is identical to or similar to a POZ polymer of the present disclosure to which it is being compared (a "comparator POZ conjugate") in all other respects. In one embodiment, the reference POZ conjugate is a conjugate of Structure 1 above where R* is H, R** is —$CH_2CH_3$, a is random, n is 190, o is 3-5 and p is the same between the reference and comparator POZ conjugates. In another embodiment, the reference POZ conjugate is a conjugate of Structure 1 above where R*, a, n, p, o, and the agent are each selected to be the same on the reference and comparator POZ conjugates. In another embodiment, the reference POZ conjugate is a conjugate of Structure 1 above where R*, a, p, o, and the agent are each selected to be the same on the reference and comparator POZ conjugates. In another embodiment, the reference POZ conjugate is a conjugate of Structure 1 above where R*, a, n, p, and the agent are each selected to be the same on the reference and comparator POZ conjugates. In another embodiment, the reference POZ conjugate is a conjugate of Structure 1 above where R*, a, n, o, and p are each selected to be the same on the reference and comparator POZ conjugates. In another embodiment, the reference POZ conjugate is a conjugate of Structure 2 above where R*, a, n, p, and the agent are each selected to be the same on the reference and comparator POZ conjugates.

As used herein the term "substantially all" with reference to a time period herein means 80% or more of that time period, such as 90% or 95% of that time period.

As used herein, the phrase "stimulates the formation of the compact conformation" when referring to a POZ conjugate does not mean that the water soluble POZ polymer portion of the POZ conjugate completely folds around the agent and/or the core, but means that the water soluble POZ polymer portion of the POZ conjugate folds to a greater extent around the agent and/or the core (i.e., form a tighter shell), for example as compared to a Reference POZ Conjugate or a POZ conjugate containing a different modification (for example, a more hydrophilic pendent moiety).

As used herein, the term "sustained release profile" as used in reference to a POZ conjugate of the present disclosure means the agent is released from the POZ conjugate such that the concentration of the agent in the body (for example, the plasma concentration) is maintained at a higher level over a period of 12 hours to 4 weeks.

As used herein, the term "water soluble" with reference to a water soluble polymer, refers to a polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

As used herein, the term "water soluble" with reference to a water soluble agent, refers to an agent with a log P value equal to or >0.5.

As used herein, the term "alkyl", whether used alone or as part of a substituent group, is a term of art and refers to saturated aliphatic groups that optionally contain one or more heteroatoms (such as O, S or N) which may be optionally substituted, including straight-chain alkyl groups, branched-chain alkyl groups, cycloalkyl groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ straight-chain alkyl group or a $C_1$-$C_3$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl. In certain embodiments, the term "alkyl" refers to a $C_1$-$C_{10}$ straight-chain alkyl group that contains one or more heteroatoms in place of a carbon atom (such as O, S or N), wherein the heteroatom may be optionally substituted. In certain embodiments, the term "alkyl" refers to a $C_1$-$C_{10}$ straight-chain alkyl group that is substituted with up to 5 groups selected from the group consisting of OH, $NH_2$ and =O.

As used herein, the term "alkenyl", whether used alone or as part of a substituent group, is a term of art and refers to unsaturated aliphatic groups that optionally contain one or more heteroatoms (such as O, S or N) which may be optionally substituted, including, a straight or branched chain hydrocarbon radical containing from 2 to 30 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

As used herein, the term "alkynyl", whether used alone or as part of a substituent group, is a term of art and refers to unsaturated aliphatic groups that optionally contain one or more heteroatoms (such as O, S or N) which may be optionally substituted, including, straight or branched chain hydrocarbon radical containing from 2 to 30 carbon atoms and containing at least one carbon-carbon triple bond. Representative examples of alkynyl include, but are not limited, to acetylenyl, 1-propynyl, 2-propynyl, 3-butynyl, 2-pentynyl, 4-pentynyl, and 1-butynyl.

As used herein, the term "substituted alkyl", "substituted alkenyl", and "substituted alkynyl" refers to alkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, heterocyclyloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, heterocyclylamine, (alkyl)(heterocyclyl)-amine, (aryl)(heterocyclyl)amine, diheterocyclylamine, and nitriles; a silicon atom in groups such as in trialkylsilyl groups, dialkylarylsilyl groups, alkyldiarylsilyl groups, and triarylsilyl groups; and other heteroatoms in various other groups. In a specific embodiment, a "polar alkyl", "polar alkenyl", and "polar alkynyl", refers to alkyl, alkenyl, and alkynyl groups substituted with an atom that results in a polar covalent bond. In another specific embodiment, a "polar alkyl", "polar alkenyl", and "polar alkynyl" refers to C1 to C5 alkyl, alkenyl, and alkynyl, groups substituted with an atom that results in a polar covalent bond. In a specific embodiment, a "polar alkyl", "polar alkenyl", and "polar alkynyl", refers to alkyl, alkenyl, alkynyl groups, such as C1 to C5 alkyl, alkenyl, and alkynyl groups, substituted with an —OH group and/or a —C(O)—OH group.

As used herein, the term "halo" or "halogen" whether used alone or as part of a substituent group, is a term of art and refers to —F, —Cl, —Br, or —I.

As used herein, the term "alkoxy", whether used alone or as part of a substituent group, is a term of art and refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "aralkyl" or "arylalkyl", whether used alone or as part of a substituent group, is a term of art and refers to an alkyl group substituted with an aryl group, wherein the moiety is appended to the parent molecule through the alkyl group. An arylalkyl group may be optionally substituted. A "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "heteroaralkyl" or "heteroarylalkyl", whether used alone or as part of a substituent group, is a term of art and refers to an alkyl group substituted with a heteroaryl group, wherein the moiety is appended to the parent molecular moiety through the alkyl group. A heteroarylalkyl may be optionally substituted. The term "substituted heteroarylalkyl" has the same meaning with respect to unsubstituted heteroarylalkyl groups that substituted aryl groups had with respect to unsubstituted aryl groups.

As used herein, the term "heterocyclylalkyl", whether used alone or as part of a substituent group, is a term of art and refers to unsubstituted or substituted alkyl, alkenyl or alkynyl groups in which a hydrogen or carbon bond of the unsubstituted or substituted alkyl, alkenyl or alkynyl group is replaced with a bond to a heterocyclyl group. A heterocyclylalkyl may be optionally substituted. The term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

As used herein, the term "aryl", whether used alone or as part of a substituent group, is a term of art and refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group. The aryl group may be optionally substituted.

As used herein, the term "cycloalkyl", whether used alone or as part of a substituent group, is a term of art and refers to a saturated carbocyclic group containing from three to six ring carbon atoms, wherein such ring may optionally be substituted with a substituted or unsubstituted alkyl group or a substituent as described for a substituted alkyl group. Exemplary cycloalkyl groups include, but are not limited to, cyclopropyl, cyclobutyl, cyclopentyl, cyclohexyl, 2-methylcyclobutyl and 4-ethylcyclohexyl.

As used herein, the term "heteroaryl", whether used alone or as part of a substituent group, is a term of art and refers to a monocyclic, bicyclic, and polycyclic aromatic group having 3 to 30 total atoms including one or more heteroatoms such as nitrogen, oxygen, or sulfur in the ring structure. Exemplary heteroaryl groups include azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

As used herein, the term "heterocyclyl", whether used alone or as part of a substituent group, is a term of art and refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 15 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like.

As used herein, the terms "treatment", "treat", and "treating" refers a course of action (such as administering a conjugate as described herein or pharmaceutical composition comprising a conjugate as described herein) so as to prevent, eliminate, or reduce a symptom, aspect, or characteristics of a disease or condition. Such treating need not be absolute to be useful. In one embodiment, treatment includes a course of action that is initiated concurrently with or after the onset of a symptom, aspect, or characteristics of a disease or condition. In another embodiment, treatment includes a course of action that is initiated before the onset of a symptom, aspect, or characteristics of a disease or condition.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the terms "individual", "subject", or "patient" refers to any animal, including mammals, such as mice, rats, other rodents, rabbits, dogs, cats, swine, cattle, sheep, horses, or primates, and humans. The terms may specify male or female or both, or exclude male or female. In a preferred embodiment, the terms "individual", "subject", or "patient" refers to a human.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

Certain compounds contained in the POZ conjugates of the present disclosure may exist in particular geometric or stereoisomeric forms. In addition, compounds contained in the POZ conjugates of the present disclosure may also be optically active. The present disclosure contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

It will be understood that when a group is specified as a part of a compound, the substitution of the group may be adjusted to accommodate the particular bonds. For example, when an alkyl group is joined to two other groups, the alkyl group is considered an alkylene group.

The term "substituted" is also contemplated to include all permissible substituents of organic compounds. In a broad aspect, the permissible substituents include acyclic and cyclic, branched and unbranched substituents, carbocyclic and heterocyclyl, aromatic and nonaromatic substituents of organic compounds. Illustrative substituents include, for example, those described herein above. For purposes of this disclosure, the heteroatoms, such as oxygen or nitrogen, may have hydrogen substituents and/or any permissible substituents of organic compounds described herein which satisfy the valences of the heteroatoms. Exemplary substitutions include, but are not limited to, hydroxy, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. This invention is not intended to be limited in any manner by the permissible substituents of organic compounds.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of conjugate. As another example, the salt may comprise less than one inorganic or organic acid molecule per molecule of base, such as two molecules of conjugate per inorganic or organic acid molecule.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Science and Practice of Pharmacy* (23$^{rd}$ edition, ISBN 9780128200070) and *Handbook of Pharmaceutical Excipients* (8th edition, 9780-85-711271-2), each herein incorporated by reference in their entirety.

Compositions and Methods for Controlling the Conformation of a POZ Conjugate and Modulating the Release Rate of an Agent from a POZ Conjugate The present disclosure provides a method of controlling the conformation of a POZ conjugate, the cleavage of the agent from the POZ conjugate, the release rate of an agent a POZ conjugate, selecting a release profile of the agent from the POZ conjugate, or combinations of the foregoing. In a general embodiment, such method comprises providing a POZ conjugate comprising a water-soluble POZ polymer and an agent linked to the water-soluble POZ polymer by a physiologically degradable linkage, or a pharmaceutically acceptable form thereof, wherein the conformation of the POZ conjugate, the cleavage of the agent from the POZ conjugate, the release of the agent from the POZ, and/or selection of a release profile of the agent from the POZ conjugate is controlled by selecting a POZ polymer characteristic, an agent characteristic, a loading characteristic, or a combination of the foregoing.

In one embodiment, the method of controlling the conformation of a POZ conjugate, controlling the cleavage of the agent from the POZ conjugate, controlling the release of the agent from the POZ, and/or selecting of a release profile of the agent from the POZ conjugate, comprises selecting a POZ conjugate characteristic to either stimulate the formation of the compact conformation of the POZ conjugate (i.e., to decrease the release rate of the agent from the POZ conjugate) or inhibit the formation of the compact conformation of the POZ conjugate (i.e., to increase the release rate of the agent from the POZ conjugate). As such, the release rate of the agent from the POZ conjugate can be controlled by selecting one or more characteristics of the POZ conjugate. Such characteristics include, but are not limited to, a POZ polymer characteristic, an agent characteristic, and a loading characteristic.

In one embodiment, the method of controlling the conformation of a POZ conjugate, controlling the cleavage of the agent from the POZ conjugate, controlling the release of the agent from the POZ, and/or selecting of a release profile of the agent from the POZ conjugate, comprises selecting a POZ polymer characteristic to inhibit the formation of the compact conformation of the POZ conjugate or to stimulate the formation of the compact conformation of the POZ conjugate. Suitable POZ polymer characteristics include, but are not limited to, the presence of a hydrophilic or hydrophobic pendent moiety on the POZ polymer portion, the hydrophobic character of the pendant groups on the POZ polymer portion (particularly when the POZ polymer portion lacks a hydrophilic or hydrophobic pendent moiety), and the molecular weight of the POZ polymer.

In one aspect of this embodiment, the method comprises including one or more hydrophilic pendent moieties on the POZ polymer portion. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising including a hydrophilic pendant group in the POZ polymer portion of the POZ conjugate. As discussed above, when the POZ polymer portion contains a hydrophilic pendant group, the formation of the compact conformation of the POZ conjugate is inhibited (as compared to a reference POZ conjugate lacking the hydrophilic pendent moieties). While not being bound by any particular theory, the inclusion of one or more hydrophilic pendant groups inhibits the POZ polymer portion from interacting with the linked agent and/or core and thereby inhibits the formation of the compact conformation of the POZ conjugate. Furthermore, altering the number of hydrophilic pendant groups allows the extent to which the formation of the compact conformation of the POZ conjugate is inhibited to be controlled.

A POZ conjugate that contains a hydrophilic pendant group will exhibit a release rate of the agent from the POZ conjugate that is increased (shorter $t_{1/2}$) as compared to the release rate of the agent from a reference POZ conjugate that does not contain such a modification. As such, the present disclosure provides a method of inhibiting the formation of the compact conformation of a POZ conjugate, the method comprising including a hydrophilic pendant group in the POZ polymer portion of the POZ conjugate. Furthermore, the present disclosure provides a method of increasing the release rate of an agent from a POZ conjugate, the method comprising including a hydrophilic pendant group in the POZ polymer portion of the POZ conjugate. Still further, the present disclosure provides a method of selecting a release profile, for example a release profile with a shorter $t_{1/2}$, of an agent from a POZ conjugate, the method comprising including a hydrophilic pendant group in the POZ polymer portion of the POZ conjugate.

In another aspect of this embodiment, the method comprises including a hydrophobic pendant group in the POZ polymer portion of the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising including a hydrophobic pendant group in the POZ polymer portion of the POZ conjugate. While not being bound by any particular theory, the inclusion of one or more hydrophobic pendant groups stimulates the POZ polymer portion to interact with the linked agent and/or core and thereby stimulates the formation of the compact conformation of the POZ conjugate (as compared to a reference POZ conjugate not containing the hydrophobic pendent). Furthermore, altering the number of hydrophobic pendant groups allows the extent to which the formation of the compact conformation is stimulated to be controlled.

A POZ conjugate that contains a hydrophobic pendant group, will exhibit a release rate of the agent from the POZ conjugate that is decreased (longer $t_{1/2}$) as compared to the release rate of the agent from a reference POZ conjugate that does not contain such a modification. As such, the present disclosure provides a method of stimulating the formation of the compact conformation of a POZ conjugate, the method comprising including a hydrophobic pendant group in the POZ polymer portion of the POZ conjugate. Furthermore, the present disclosure provides a method of decreasing the release rate of an agent from a POZ conjugate, the method comprising including a hydrophobic pendant group in the POZ polymer portion of the POZ conjugate. Still further, the present disclosure provides a method of selecting a release profile, for example a release profile with a longer $t_{1/2}$, of an agent from a POZ conjugate, the method comprising including a hydrophobic pendant group in the POZ polymer portion of the POZ conjugate.

In another aspect of this embodiment, the method comprises excluding a hydrophobic pendant group in the POZ polymer portion of the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising excluding a hydrophobic pendant group in the POZ polymer portion of the POZ conjugate. When the POZ polymer portion does not contain a hydrophobic pendant group, the formation of the compact conformation of the POZ conjugate is not stimulated (as compared to a reference POZ conjugate containing a hydrophobic pendent moieties).

As such, a POZ conjugate that lacks a hydrophobic pendant group will exhibit a release rate of the agent from the POZ conjugate that is increased (shorter $t_{1/2}$) as compared to the release rate of the agent from a reference POZ conjugate that contains a hydrophobic pendant. As such, the present disclosure provides a method of inhibiting the formation of the compact conformation of a POZ conjugate, the method comprising excluding a hydrophobic pendant group in the POZ polymer portion of the POZ conjugate. Furthermore, the present disclosure provides a method of decreasing the release rate of an agent from a POZ conjugate, the method comprising excluding a hydrophobic pendant group in the POZ polymer portion of the POZ conjugate. Still further, the present disclosure provides a method of a release profile, for example a release profile with a shorter $t_{1/2}$, of an agent from a POZ conjugate, the method comprising excluding a hydrophobic pendant group in the POZ polymer portion of the POZ conjugate.

In another aspect of this embodiment, the method comprises excluding a hydrophilic pendant group in the POZ polymer portion of the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising excluding a hydrophilic pendant group in the POZ polymer portion of the POZ conjugate. When the POZ polymer portion does not contain a hydrophilic pendant group, the formation of the compact conformation of the POZ conjugate is not inhibited (as compared to a reference polypeptide containing a hydrophilic pendent moieties).

As such, a POZ conjugate that lacks a hydrophilic pendant group will exhibit a release rate of the agent from the POZ conjugate that is decreased (longer $t_{1/2}$) as compared to the release rate of the agent from a reference POZ conjugate that contains a hydrophilic pendant. As such, the present disclosure provides a method of stimulating the formation of the compact conformation of a POZ conjugate, the method comprising excluding a hydrophilic pendant group in the POZ polymer portion of the POZ conjugate. Furthermore, the present disclosure provides a method of increasing the release rate of an agent from a POZ conjugate, the method comprising excluding a hydrophilic pendant group in the POZ polymer portion of the POZ conjugate. Still further, the present disclosure provides a method of a release profile, for example a release profile with a longer $t_{1/2}$, of an agent from a POZ conjugate, the method comprising excluding a hydrophilic pendant group in the POZ polymer portion of the POZ conjugate.

In the foregoing discussion, the impact of the hydrophilic and hydrophobic pendent moieties of the POZ polymer portion is determined in relation to a POZ conjugate of substantially the same properties except for presence/absence of the pendent moieties (for example, if the effect of a hydrophilic pendent moieties on a POZ-CBD conjugate is being determined, the effect of the hydrophilic pendent moiety is determined on a POZ-CBD conjugate having the same structure and substantially the same properties, for example loading percentage and molecular weight, but lacking the hydrophilic pendent moieties). In one embodiment, the impact of adding or deleting hydrophilic or hydrophobic pendent moieties is specific for a particular POZ conjugate and the impact of adding or deleting hydrophilic or hydrophobic pendent moieties may be different, either qualitatively or quantitatively, for another POZ conjugate. Furthermore, in another embodiment the impact of adding or deleting hydrophilic or hydrophobic pendent moieties may also be influenced by other POZ conjugate characteristics as discussed herein, such as, but not limited to, the nature of the agent. For example, in general an agent that display a low water solubility (for example, an agent with a Log P value of 6.1) will exhibit a greater interaction with a POZ polymer portion despite the presence of hydrophilic pendent moieties and stimulate the formation of the compact conformation and/or display a decreased release rate as compared to an agent in the same POZ conjugate that has a lower Log P (for example, a Log P of 4.8).

In another aspect of this embodiment, the method comprises controlling the molecular weight of the POZ polymer portion of the POZ conjugate. In general, as the molecular weight of the POZ polymer portion increases, the formation of the compact conformation of the POZ conjugate is stimulated and the release rate of an agent from the POZ conjugate decreases (longer $t_{1/2}$) (each of the foregoing as compared to reference POZ conjugate having a POZ polymer portion of lower molecular weight). In one embodiment, the method of controlling the conformation of a POZ conjugate, controlling the cleavage of the agent from the POZ conjugate, controlling the release of the agent from the POZ, and/or selecting of a release profile of the agent from the POZ conjugate, comprises selecting a molecular weight for POZ polymer portion that stimulates or inhibits the formation of the compact conformation of the POZ conjugate. In one aspect of this embodiment, a molecular weight ≥20 kDa (for example, 25 kDa, 30 kDa, 35 kDa, 40 kDa, 45 kDa, 50 kDa, 75 kDa, 100 kDa, or 150 kDa but less than 1000 kDa) stimulates the formation of the compact conformation and a molecular weight <20 kDa (for example, 17.5 kDa, 15, kDa, 12.5 kDa, 10.0 kDa, 8 kDa, 6 kDa, 4 kDa, or 2 kDa but greater than 1 kDa) inhibits the formation of the compact conformation. In another aspect of this embodiment, a molecular weight ≥30 kDa stimulates the formation of the compact conformation and a molecular weight <15 kDa inhibits the formation of the compact conformation.

In one aspect of this embodiment, the present disclosure provides a method of stimulating the formation of the compact conformation of a POZ conjugate, the method comprising providing a POZ conjugate comprising a POZ polymer portion of ≥20 kDa. Furthermore, the present disclosure provides a method of decreasing the release rate of an agent from a POZ conjugate, the method comprising providing a POZ conjugate comprising a POZ polymer portion of ≥20 kDa. Still further, the present disclosure provides a method of selecting a release profile, for example a release profile with a longer $t_{1/2}$, of an agent from a POZ conjugate, the method comprising providing a POZ conjugate comprising a POZ polymer portion of ≥20 kDa. In certain embodiments of this aspect, the molecular weight of the POZ polymer portion is 25 kDa, 30 kDa, 35 kDa, 40 kDa, 45 kDa, 50 kDa, 75 kDa, 100 kDa, or 150 kDa and less than 1000 kDa. In certain embodiments of this aspect, the molecular weight of the POZ polymer portion is ≥20 kDa and ≤100 kDa. In certain embodiments of this aspect, the molecular weight of the POZ polymer portion is ≥50 kDa and ≤150 kDa.

Furthermore, generally as the molecular weight of the POZ polymer portion decreases, the formation of the compact conformation of the POZ conjugate is inhibited and the release rate of an agent from the POZ conjugate increases (shorter $t_{1/2}$) (each of the foregoing as compared to POZ polymer portions of higher molecular weight).

In one aspect of this embodiment, the present disclosure provides a method of inhibiting the formation of the compact conformation of a POZ conjugate, the method comprising providing a POZ conjugate comprising a POZ polymer portion of <20 kDa. Furthermore, the present disclosure provides a method of increasing the release rate of an agent from a POZ conjugate, the method comprising providing a POZ conjugate comprising a POZ polymer portion of <20 kDa or less in the POZ polymer portion of the POZ conjugate. Still further, the present disclosure provides a method of selecting a release profile, for example a release profile with a longer $t_{1/2}$, of an agent from a POZ conjugate, the method comprising providing a POZ conjugate comprising a POZ polymer portion of <20 kDa. In certain embodiments of this aspect, the molecular weight of the POZ polymer portion is 17.5 kDa, 15, kDa, 12.5 kDa, 10.0 kDa, 8 kDa, 6 kDa, 4 kDa, or 2 kDa and greater than 1 kDa. In certain embodiments of this aspect, the molecular weight of the POZ polymer portion is ≥2 kDa and <20 kDa. In certain embodiments of this aspect, the molecular weight of the POZ polymer portion is ≥10 kDa and <20 kDa.

In the foregoing discussion, the impact of the molecular weight of the POZ polymer portion is determined in relation to a POZ conjugate of substantially the same properties except for a difference in molecular weight of the POZ polymer portion (for example, if the effect of a 60 kDa POZ polymer portion on a POZ-CBD conjugate is being determined, the effect of the POZ polymer portion is determined on a POZ-CBD conjugate having the same structure and substantially the same properties, for example loading percentage, but having a different molecular weight). In one embodiment, the impact of increasing or decreasing the molecular weight of the POZ polymer portion is specific for a particular POZ conjugate and the impact of increasing or decreasing the molecular weight of the POZ polymer portion may be different, either qualitatively or quantitatively, for another POZ conjugate. Furthermore, in another embodiment the impact of increasing or decreasing the molecular weight of the POZ polymer portion may also be influenced by other POZ conjugate characteristics as discussed herein, such as, but not limited to, the nature of the agent. For example, in general an agent that display a low water solubility (for example, an agent with a Log P value of 6.1) will exhibit a greater interaction with a POZ polymer portion with a 60 kDa POZ polymer portion and stimulate the formation of the compact conformation and/or display a decreased release rate as compared to an agent in the same POZ conjugate that has a lower Log P (for example, a Log P of 4.8).

In one aspect of this embodiment, the method comprises changing the hydrophobic character of the pendent groups on the POZ polymer portion, particularly when the POZ conjugate is of Structure 1 above and lacks a hydrophilic or hydrophobic pendent moiety. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising altering the hydrophobic character of the pendent groups on the POZ polymer portion of the POZ conjugate. As discussed above, when the POZ polymer portion contains pendant groups that provide a more hydrophobic character, the formation of the compact conformation of the POZ conjugate is stimulated (as compared to a reference POZ conjugate pendent groups of a less hydrophobic character). For example, a POZ conjugate with propyl pendent groups on the POZ polymer portion will have a more hydrophobic character than a POZ conjugate with methyl pendent groups on the POZ polymer portion. As another example, a POZ conjugate with propyl pendent groups on the POZ polymer portion will have a more hydrophobic character than a POZ conjugate with 50% ethyl and 50% methyl pendent groups on the POZ polymer portion. While not being bound by any particular theory, the hydrophobic nature of the pendant groups stimulates the interaction of the POZ polymer portion with the linked agent and/or core and thereby stimulates the formation of the compact conformation of the POZ conjugate. Furthermore, altering the number of hydrophobic pendant groups allows the extent to which the formation of the compact conformation of the POZ conjugate is stimulated to be controlled.

A POZ conjugate that contains pendant group with a greater hydrophobic character will exhibit a release rate of the agent from the POZ conjugate that is decreased (longer $t_{1/2}$) as compared to the release rate of the agent from a reference POZ conjugate that contains pendent groups with a less hydrophobic character. As such, the present disclosure provides a method of stimulating the formation of the compact conformation of a POZ conjugate, the method comprising including pendant group with a hydrophobic character in the POZ polymer portion of the POZ conjugate. Furthermore, the present disclosure provides a method of decreasing the release rate of an agent from a POZ conjugate, the method comprising including pendant group with a hydrophobic character in the POZ polymer portion of the POZ conjugate. In certain embodiments of the methods described herein, the comparison is made to a POZ polymer of substantially the same properties but with methyl pendent groups.

In the foregoing discussion, the impact of pendent groups with a hydrophobic character on the POZ polymer portion is determined in relation to a POZ conjugate of substantially the same properties except for hydrophobic character of the pendent groups (for example, if the effect of a propyl pendent groups on a POZ-CBD conjugate is being determined, the effect of the propyl pendent group is determined on a POZ-CBD conjugate having the same structure and substantially the same properties, for example loading percentage and molecular weight, but containing less hydrophobic pendent groups, such as methyl pendent groups). In one embodiment, the impact of pendent groups with a hydrophobic character on the POZ polymer portion is specific for a particular POZ conjugate and the impact of pendent groups with a hydrophobic character on the POZ polymer portion may be different, either qualitatively or quantitatively, for another POZ conjugate. Furthermore, in another embodiment the impact of pendent groups with a hydrophobic character on the POZ polymer portion may also be influenced by other POZ conjugate characteristics as discussed herein, such as, but not limited to, the nature of the agent. For example, in general an agent that display a low water solubility (for example, an agent with a Log P value of 6.1) will exhibit a greater interaction with a POZ polymer portion containing pendent groups with a hydrophobic character and stimulate the formation of the compact conformation and/or display a decreased release rate as compared to an agent in the same POZ conjugate that has a lower Log P (for example, a Log P of 4.8).

The conformation of the POZ conjugate may also be controlled by selecting an agent characteristic. The present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting an agent characteristic of the POZ conjugate. Suitable agent characteristics include, but are not limited to, the solubility of the agent, the molecular volume of the agent, the total polar surface area (TPSA) of the agent, or a combination of the foregoing.

In one aspect of this embodiment, the method for controlling the conformation of a POZ conjugate, controlling the cleavage of the agent from the POZ conjugate, controlling the release of the agent from the POZ, and/or selecting of a release profile of the agent from the POZ conjugate comprises selecting an agent with a low solubility in water for inclusion in the POZ conjugate. Therefore, the present disclosure provides a method of controlling the conformation of the POZ conjugate, the method comprising selecting an agent with a low solubility in water for inclusion in the POZ conjugate. Agents with low solubility in water stimulate the formation of the compact conformation of the POZ conjugate (as compared to a reference POZ conjugate having an agent with a higher solubility in water). A POZ conjugate that contains an agent with a low solubility in water, will exhibit a release rate of the agent from the POZ conjugate that is decreased (longer $t_{1/2}$) as compared to the release rate of the agent from a reference POZ conjugate that contains an agent with a higher solubility in water.

As such, the present disclosure provides a method of stimulating the formation of the compact conformation of a POZ conjugate, the method comprising selecting an agent with a low solubility in water for inclusion in the POZ conjugate. Furthermore, the present disclosure provides a method of decreasing the release rate of an agent from a POZ conjugate, the method comprising selecting an agent with a low solubility in water for inclusion in the POZ conjugate. Still further, the present disclosure provides a method of selecting a release profile, for example a release profile with a longer $t_{1/2}$, of an agent from a POZ conjugate, the method comprising selecting an agent with a low solubility in water for inclusion in the POZ conjugate.

In certain embodiments of this aspect, the water solubility of the agent is determined by the Log P value of the agent. Unless specified otherwise, in the present disclosure a Log P value means that the value is determined by the partitioning of the agent in a biphasic system of n-octanol and water as described in Dearden et al. (Molecular Informatics, Vol 7(3), page 133-134, 1988). In certain embodiments, an agent with a low water solubility has a Log P value of ≥0.5. In certain embodiments, an agent with a low water solubility has a Log P value of ≥1.0. In certain embodiments, an agent with a low water solubility has a Log P value of ≥1.5. In certain embodiments, an agent with a low water solubility has a Log P value of ≥2.0. In certain embodiments, an agent with a low water solubility has a Log P value of ≥2.5. In certain embodiments, an agent with a low water solubility has a Log P value of ≥3.0. In certain embodiments, an agent with a low water solubility has a Log P value of ≥3.5. In certain embodiments, an agent with a low water solubility has a Log P value of ≥4.0. In certain embodiments, an agent with a low water solubility has a Log P value of ≥4.5. In certain embodiments, an agent with a low water solubility has a Log P value of ≥5.0. In certain embodiments, an agent with a low water solubility has a Log P value of ≥5.5. In certain embodiments, an agent with a low water solubility has a Log P value of ≥6.0. In certain embodiments, an agent with a low water solubility has a Log P value of ≥6.5. In certain embodiments, an agent with a low water solubility has a Log P value of ≥7.0. In certain embodiments, an agent with a low water solubility has a Log P value of ≥7.5. In certain embodiments, an agent with a low water solubility has a Log P value of ≥8.0. In certain embodiments of the foregoing, the agent has a Log P value of ≤10. In certain embodiments of the foregoing, the agent has a Log P value of ≤0.5 and ≤10.

In one aspect of this embodiment, the method for controlling the conformation of a POZ conjugate, controlling the cleavage of the agent from the POZ conjugate, controlling the release of the agent from the POZ, and/or selecting of a release profile of the agent from the POZ conjugate comprises selecting an agent with a high solubility in water for inclusion in the POZ conjugate. Therefore, the present disclosure provides a method of controlling the conformation of the POZ conjugate, the method comprising selecting an agent with a high solubility in water for inclusion in the POZ conjugate. Agents with high solubility in water inhibit the formation of the compact conformation of the POZ conjugate (as compared to a reference POZ conjugate having an agent with a lower solubility in water). A POZ conjugate that contains an agent with a high solubility in water, will exhibit a release rate of the agent from the POZ conjugate that is increased (shorter $t_{1/2}$) as compared to the release rate of the agent from a reference POZ conjugate that contains an agent with a lower solubility in water.

As such, the present disclosure provides a method of inhibiting the formation of the compact conformation of a POZ conjugate, the method comprising selecting an agent with a high solubility in water for inclusion in the POZ conjugate. Furthermore, the present disclosure provides a method of increasing the release rate of an agent from a POZ conjugate, the method comprising selecting an agent with a high solubility in water for inclusion in the POZ conjugate. Still further, the present disclosure provides a method of selecting a release profile, for example a release profile with a shorter $t_{1/2}$, of an agent from a POZ conjugate, the method comprising selecting an agent with a high solubility in water for inclusion in the POZ conjugate.

In certain embodiments, an agent with a high water solubility has a Log P value of <0.5.

In another aspect of this embodiment, the method comprises selecting an agent with a large molecular volume for inclusion in the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting an agent with a large molecular volume for inclusion in the POZ conjugate. Agents with a large molecular volume inhibit the formation of the compact conformation of the POZ conjugate (such as through steric hindrance). A POZ conjugate that contains an agent with a large molecular volume, will exhibit a release rate of the agent from the POZ conjugate that is increased (shorter $t_{1/2}$) as compared to the release rate of the agent from a POZ conjugate that contains an agent with a smaller molecular volume.

As such, the present disclosure provides a method of inhibiting the formation of the compact conformation of a POZ conjugate, the method comprising selecting an agent with a large molecular volume for inclusion in the POZ conjugate. Furthermore, the present disclosure provides a method of increasing the release rate of an agent from a POZ conjugate, the method comprising selecting an agent with a large molecular volume for inclusion in the POZ conjugate. Still further, the present disclosure provides a method of selecting a release profile, for example a release profile with a shorter $t_{1/2}$, of an agent from a POZ conjugate, the method comprising selecting an agent with a large molecular volume for inclusion in the POZ conjugate.

In certain embodiments of this aspect, the molecular volume is determined based on group contributions obtained by fitting sum of fragment contributions to real 3D volume to produce a training set (for example, about 12,000) drug like molecules. 3D molecular geometries for the training set were fully optimized by the semiempirical AM1 method (Molinspiration chemoinformatics). In certain embodiments, an agent with a large molecular volume has molecular volume of ≥300. In certain embodiments, an agent with a large molecular volume has molecular volume of ≥350. In certain embodiments, an agent with a large molecular volume has molecular volume of ≥400. In certain embodiments, an agent with a large molecular volume has molecular volume of ≥450. In certain embodiments, an agent with a large molecular volume has molecular volume of ≥500. In certain embodiments, an agent with a large molecular volume has molecular volume of ≥300 and ≤500. In certain embodiments, an agent with a large molecular volume has molecular volume of ≥300 and ≤400.

In another aspect of this embodiment, the method comprises selecting an agent with a small molecular volume for inclusion in the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting an agent with a small molecular volume for inclusion in the POZ conjugate. Agents with a small molecular volume stimulate or do not inhibit the formation of the compact conformation of the POZ conjugate. As such, a POZ conjugate that contains an agent with a small molecular volume, will exhibit a release rate of the agent from the POZ conjugate that is increased (longer $t_{1/2}$) as compared to the release rate of the agent from a POZ conjugate that contains an agent with a larger molecular volume.

As such, the present disclosure provides a method of stimulating the formation of the compact conformation of a POZ conjugate, the method comprising selecting an agent with a small molecular volume for inclusion in the POZ conjugate. Furthermore, the present disclosure provides a method of decreasing the release rate of an agent from a POZ conjugate, the method comprising selecting an agent with a small molecular volume for inclusion in the POZ conjugate. Still further, the present disclosure provides a method of selecting a release profile, for example a release profile with a longer $t_{1/2}$, of an agent from a POZ conjugate, the method comprising selecting an agent with a small molecular volume for inclusion in the POZ conjugate.

In certain embodiments of this aspect, the molecular volume is determined as described above. In certain embodiments, an agent with a small molecular volume has molecular volume of ≤300. In certain embodiments, an agent with a small molecular volume has molecular volume of ≤275. In certain embodiments, an agent with a small molecular volume has molecular volume of ≤250. In certain embodiments, an agent with a small molecular volume has molecular volume of ≤200. In certain embodiments, an agent with a small molecular volume has molecular volume of ≤100. In certain embodiments, an agent with a small molecular volume has molecular volume of ≤50. In certain embodiments, an agent with a small molecular volume has molecular volume of ≤50<300. In certain embodiments, an agent with a small molecular volume has molecular volume of ≥100<300.

In another aspect of this embodiment, the method comprises selecting an agent with a high TPSA for inclusion in the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting an agent with a high TPSA for inclusion in the POZ conjugate. Agents with a high TPSA inhibit the formation of the compact conformation of the POZ conjugate. A POZ conjugate that contains an agent with a high TPSA, will exhibit a release rate of the agent from the POZ conjugate that is increased (shorter $t_{1/2}$) as compared to the release rate of the agent from a POZ conjugate that contains an agent with a smaller TPSA.

As such, the present disclosure provides a method of inhibiting the formation of the compact conformation of a POZ conjugate, the method comprising selecting an agent with a high TPSA for inclusion in the POZ conjugate. Furthermore, the present disclosure provides a method of increasing the release rate of an agent from a POZ conjugate, the method comprising selecting an agent with a low TPSA for inclusion in the POZ conjugate. Still further, the present disclosure provides a method of selecting a release profile, for example a release profile with a shorter $t_{1/2}$, of an agent from a POZ conjugate, the method comprising selecting an agent with a high TPSA for inclusion in the POZ conjugate.

In certain embodiments of this aspect, the TPSA is determined based on the methodology published by Ertl, et al. (J. Med. Chem., 43, 3714-3717, 2000) as the sum of fragment contributions O- and N-centered polar fragments. In certain embodiments, an agent with a high TPSA has a TPSA ≥35. In certain embodiments, an agent with a high TPSA has a TPSA of ≥40. In certain embodiments, an agent with a high TPSA has a TPSA of ≥45. In certain embodiments, an agent with a high TPSA has a TPSA of ≥50. In certain embodiments, an agent with a high TPSA has a TPSA of ≥55. In certain embodiments, an agent with a high TPSA has a TPSA of ≥60. In certain embodiments, an agent with a high TPSA has a TPSA of ≥65. In certain embodiments, an agent with a high TPSA has a TPSA of ≥35 and ≤75. In certain embodiments, an agent with a high TPSA has a TPSA of ≥40 and ≤60.

In another aspect of this embodiment, the method comprises selecting an agent with a low TPSA for inclusion in the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting an agent with a low TPSA for inclusion in the POZ conjugate. Agents with a low TPSA stimulate or do not inhibit the formation of the compact conformation of the POZ conjugate. A POZ conjugate that contains an agent with a low TPSA, will exhibit a release rate of the agent from the POZ conjugate that is decreased (longer $t_{1/2}$) as compared to the release rate of the agent from a POZ conjugate that contains an agent with a larger TPSA.

As such, the present disclosure provides a method of stimulating the formation of the compact conformation of a POZ conjugate, the method comprising selecting an agent with a low TPSA for inclusion in the POZ conjugate. Furthermore, the present disclosure provides a method of decreasing the release rate of an agent from a POZ conjugate, the method comprising selecting an agent with a low TPSA for inclusion in the POZ conjugate. Still further, the present disclosure provides a method of selecting a release profile, for example a release profile with a longer $t_{1/2}$, of an agent from a POZ conjugate, the method comprising selecting an agent with a low TPSA for inclusion in the POZ conjugate.

In certain embodiments of this aspect, the TPSA is determined as described above. In certain embodiments, an agent with a low TPSA has a TPSA <35. In certain embodiments, an agent with a low TPSA has a TPSA of ≤30. In certain embodiments, an agent with a low TPSA has a TPSA of ≤25. In certain embodiments, an agent with a low TPSA has a TPSA of ≤20. In certain embodiments, an agent with a low TPSA has a TPSA of ≤15. In certain embodiments, an agent with a low TPSA has a TPSA of <35 and >15.

In the foregoing discussion, the impact of the agent characteristic is determined in relation to a POZ conjugate of substantially the same properties except for a difference in the agent characteristic(s) being studied (for example, if the effect of an agent with a high TPSA is being determined on a POZ-CBD conjugate of 20 kDa, the effect of the high TPSA is determined on a POZ-CBD conjugate having the same structure and substantially the same properties, for example loading percentage and molecular weight, but with an agent having a lower TPSA). In one embodiment, the impact of an agent characteristic is specific for a particular POZ conjugate and the impact of an agent characteristic may be different, either qualitatively or quantitatively, for another POZ conjugate. Furthermore, in another embodiment the impact of an agent characteristic may also be influenced by other POZ conjugate characteristics as discussed herein, such as, but not limited to, the loading percentage. For example, in general a POZ conjugate comprising an agent with a high TPSA (for example, TPSA of 62.2) at a 10% loading percentage will inhibit the formation of the compact confirmation of the POZ conjugate to a greater degree and/or display an increased release rate as compared the same POZ conjugate that has a lower loading percentage (for example 4%).

The conformation of the POZ conjugate may also be controlled by selecting a loading characteristic. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting a loading characteristic of the POZ conjugate.

In one aspect of this embodiment, the method comprises selecting a high loading percentage for the agent in the POZ conjugate. Therefore, the present disclosure provides a method of controlling the conformation of the POZ conjugate, the method comprising selecting a high loading percentage for the agent in the POZ conjugate. POZ conjugates with a higher loading percentage will stimulate the formation of the compact conformation to a higher degree as compared to a reference POZ conjugate that contains a lower loading percentage for the agent in the POZ conjugate. A POZ conjugate that contains a high loading percentage for the agent in the POZ conjugate, will exhibit a release rate of the agent from the POZ conjugate that is decreased (longer $t_{1/2}$) as compared to the release rate of the agent from a reference POZ conjugate that contains a lower loading percentage for the agent in the POZ conjugate.

As such, the present disclosure provides a method of stimulating the formation of the compact conformation of a POZ conjugate, the method comprising selecting a high loading percentage for the agent in the POZ conjugate. Furthermore, the present disclosure provides a method of decreasing the release rate of an agent from a POZ conjugate, the method comprising selecting a high loading percentage for the agent in the POZ conjugate. Still further, the present disclosure provides a method of selecting a release profile, for example a release profile with a longer $t_{1/2}$, of an agent from a POZ conjugate, the method comprising selecting a high loading percentage for the agent in the POZ conjugate.

In any of the foregoing methods utilizing a high loading percentage, the agent may have a log P value of <0.5, a molecular volume <300, a TPSA of <35. In any of the foregoing methods utilizing a high loading percentage, the agent may have a log P value of ≥0.5, a molecular volume >300, a TPSA of >35.

In certain embodiments, a high loading percentage for the agent is a loading percentage ≥4.0%. In certain embodiments, a high loading percentage for the agent is a loading percentage ≥5.0%. In certain embodiments, a high loading percentage for the agent is a loading percentage ≥6.0%. In certain embodiments, a high loading percentage for the agent is a loading percentage ≥7.0%. In certain embodiments, a high loading percentage for the agent is a loading percentage ≥8.0%. In certain embodiments, a high loading percentage for the agent is a loading percentage ≥9.0%. In certain embodiments, a high loading percentage for the agent is a loading percentage ≥10.0%. In certain embodiments, a high loading percentage for the agent is a loading percentage ≥11.0%. In certain embodiments, a high loading percentage for the agent is a loading percentage ≥12.0%. In certain embodiments, a high loading percentage for the agent is a loading percentage ≥13.0%. In certain embodiments, a high loading percentage for the agent is a loading percentage ≥14.0%. In certain embodiments, a high loading percentage for the agent is a loading percentage ≥15.0%. In certain embodiments, a high loading percentage for the agent is a loading percentage ≥16.0%. In certain embodiments, a high loading percentage for the agent is a loading percentage ≥4.0% and ≤20.0%. In certain embodiments, a high loading percentage for the agent is a loading percentage ≥6.0% and ≤10.0%.

In one aspect of this embodiment, the method comprises selecting a low loading percentage for the agent in the POZ conjugate. Therefore, the present disclosure provides a method of controlling the conformation of a POZ conjugate, controlling the cleavage of the agent from the POZ conjugate, controlling the release of the agent from the POZ, and/or selecting of a release profile of the agent from the POZ conjugate, the method comprising selecting a low loading percentage for the agent in the POZ conjugate. POZ conjugates with a lower loading percentage will stimulate the formation of the compact conformation to a lower degree as compared to a reference POZ conjugate that contains a higher loading percentage for the agent in the POZ conjugate. A POZ conjugate that contains a low loading percentage for the agent in the POZ conjugate, will exhibit a release rate of the agent from the POZ conjugate that is increased (shorter $t_{1/2}$) as compared to the release rate of the agent from a reference POZ conjugate that contains a higher loading percentage for the agent in the POZ conjugate.

As such, the present disclosure provides a method of inhibiting the formation of the compact conformation of a POZ conjugate, the method comprising selecting a low loading percentage for the agent in the POZ conjugate. Furthermore, the present disclosure provides a method of increasing the release rate of an agent from a POZ conjugate, the method comprising selecting a low loading percentage for the agent in the POZ conjugate. Still further, the present disclosure provides a method of selecting a release profile, for example a release profile with a shorter $t_{1/2}$, of an agent from a POZ conjugate, the method comprising selecting a low loading percentage for the agent in the POZ conjugate.

In any of the foregoing methods utilizing a low loading percentage, the agent may have a log P value of <0.5, a molecular volume <300, a TPSA of <35. In any of the foregoing methods utilizing a low loading percentage, the agent may have a log P value of ≥0.5, a molecular volume >300, a TPSA of >35.

In certain embodiments, a low loading percentage for the agent is a loading percentage ≤4.0%. In certain embodiments, a low loading percentage for the agent is a loading percentage ≤3.5%. In certain embodiments, a low loading percentage for the agent is a loading percentage ≤3.0%. In certain embodiments, a low loading percentage for the agent is a loading percentage ≤2.5%. In certain embodiments, a low loading percentage for the agent is a loading percentage ≤2.0%. In certain embodiments, a low loading percentage for the agent is a loading percentage ≤1.0%. In certain embodiments, a low loading percentage for the agent is a loading percentage <4.0% and ≥1.0%.

In the foregoing discussion, the impact of the loading percentage of the POZ polymer portion is determined in relation to a POZ conjugate of the same properties except for the loading percentage (for example, if the effect of a high loading percentage on a POZ-CBD conjugate is being determined, the effect of the high loading percentage is determined on a POZ-CBD conjugate having the same structure and substantially the same properties, for example molecular weight, but having a lower loading percentage). In one embodiment, the impact of altering the loading percentage is specific for a particular POZ conjugate and the impact of altering the loading percentage may be different, either qualitatively or quantitatively, for another POZ conjugate. Furthermore, in another embodiment the impact of increasing or decreasing the loading percentage may also be influenced by other POZ conjugate characteristics as discussed herein, such as, but not limited to, the nature of the agent. For example, in general an agent that display a low water solubility (for example, an agent with a Log P value of 6.1) will exhibit a greater interaction at a high loading percentage (for example 8.5%) with a POZ polymer portion and stimulate the formation of the compact conformation to a greater degree and/or display a decreased release rate as compared to an agent in the same POZ conjugate that has a lower Log P (for example, a Log P of 4.8).

The present disclosure also provides a method of modulating (i.e., selecting or tuning) a release rate of an agent from a POZ conjugate. By modulating the release rate of the agent, a specific release profile for the release of the gent from the POZ conjugate may be selected. The release rate of an agent from a POZ conjugate may be controlled in several ways as described herein. For example, the release rate of an agent from a POZ conjugate may be controlled through the selection of a POZ polymer characteristic, through the selection of an agent characteristic, through the selection of a loading characteristic, or combinations of the foregoing. The release rate may be monitored through determination of the half-life of the agent in vitro or in vivo after administration to a subject, with a faster release rate being correlated with a decreased half-life of the agent using the methods described in the Methods section herein.

A release profile of the agent from the POZ polymer may be selected using one of the methods above or through a combination of one or more of the methods above. For example, when a sustained release profile of the agent from the POZ conjugate is desired or it is desired to decrease the release rate of the agent from the POZ conjugate, one or more of the methods above that stimulate the formation of the compact conformation of the POZ conjugate and/or decrease the release rate of the agent from the POZ conjugate may be selected. Additionally, when a sustained release profile of the agent from the POZ conjugate is not desired or it is desired to increase the release rate of the agent from the POZ conjugate, one or more of the methods above that inhibit the formation of the compact conformation of the POZ conjugate and/or increase the release rate of the agent from the POZ conjugate may be selected.

The present disclosure also provides a POZ conjugate compositions for controlling the conformation of a POZ conjugate, controlling the cleavage of the agent from the POZ conjugate, controlling the release rate of an agent a POZ conjugate, selecting a release profile of the agent from the POZ conjugate, or combinations of the foregoing. In a general embodiment, such POZ conjugate compositions comprise a water-soluble POZ polymer and an agent linked to the water-soluble POZ polymer by a physiologically degradable linkage, or a pharmaceutically acceptable form thereof, wherein the POZ conjugate comprises one or more of the following characteristics: a hydrophilic or a hydrophobic pendentmoiety, pendant groups on the POZ polymer portion with a hydrophobic character, wherein the hydrophobic character is determined with respect to a POZ conjugate containing methyl pendent groups (particularly when the POZ polymer portion lacks a hydrophilic or hydrophobic pendent moiety), a selected (i.e., high or low) molecular weight for the POZ polymer portion, an agent with a selected (i.e., high or low) solubility in water, an agent with a selected (i.e., large or small) molecular volume, an agent with a selected (i.e., high or low) TPSA, a selected (i.e., high or low) loading percentage of the agent, or a combination of the foregoing. Such POZ conjugates may be used in any of the methods described herein.

In one embodiment, the present disclosure provides a POZ conjugate comprising a hydrophilic or hydrophobic pendent moiety. In one embodiment, the present disclosure provides a POZ conjugate comprising pendent groups with an increased hydrophobic character (for example, increased as compared to methyl pendent groups). In one embodiment, the present disclosure provides a POZ conjugate comprising a high or low loading percentage for the agent. In one embodiment, the present disclosure provides a POZ conjugate comprising an agent with low or high solubility in water. In one embodiment, the present disclosure provides a POZ conjugate comprising an agent with a log P value ≥0.5 or an agent with a log P value <0.5. In one embodiment, the present disclosure provides a POZ conjugate comprising an agent with a large or small molecular volume. In one embodiment, the present disclosure provides a POZ conjugate comprising an agent with a high or low TPSA.

The present disclosure also provides for compositions, including pharmaceutical compositions comprising a POZ conjugate of the present disclosure. Such a composition may contain any POZ conjugate described in the foregoing methods.

The present disclosure also provides for methods of treatment utilizing any on the methods, POZ conjugates, and pharmaceutical compositions described herein.

POZ Conjugate Compositions

The POZ conjugates of the present disclosure comprise a POZ polymer portion and an agent. The agent is linked to the POZ polymer through a physiologically degradable linkage. As discussed above, the present disclosure demonstrates that the release rate of an agent from the POZ conjugate and the release profile of the agent from the POZ conjugate can be controlled by altering the conformation of the POZ conjugate.

In one embodiment, a POZ conjugate of the present disclosure has the general formula I as described below. The conformation of the POZ conjugate of formula I is controlled, at least in part, by the selection of one or more of a POZ polymer characteristic, an agent characteristic, and a loading characteristic.

In one embodiment, the conformation of a POZ conjugate, the cleavage of the agent from the POZ conjugate, the release of the agent from the POZ, and/or selection of a release profile of the agent from the POZ conjugate is controlled, at least in part, by the selection of a POZ polymer characteristic.

In one aspect of this embodiment, the conformation of a POZ conjugate, the cleavage of the agent from the POZ conjugate, the release of the agent from the POZ, and/or selection of a release profile of the agent from the POZ conjugate is controlled, at least in part, by the selection of one or more pendant moieties on the POZ polymer portion (for example, selection of $R_1$) and/or the number of pendent moieties (for example, the selection of m). The present disclosure demonstrates that the inclusion of one or more hydrophilic or hydrophobic pendant groups modulates the conformation of the POZ conjugate and/or the release rate of an agent from the POZ conjugate, allowing the selection of a release profile for the agent.

In another aspect of this embodiment, the conformation of a POZ conjugate, the cleavage of the agent from the POZ conjugate, the release of the agent from the POZ, and/or selection of a release profile of the agent from the POZ conjugate is controlled, at least in part, by the selection of the molecular weight (for example, selection of n or n and optionally m and o). The present disclosure demonstrates that the varying the molecular weight of the POZ conjugate (in one embodiment, varying the molecular weight of the POZ polymer portion) modulates the conformation of the POZ conjugate and/or the release rate of an agent from the POZ conjugate, allowing the selection of a release profile for the agent.

In one embodiment, the conformation of a POZ conjugate, the cleavage of the agent from the POZ conjugate, the release of the agent from the POZ, and/or selection of a release profile of the agent from the POZ conjugate is controlled, at least in part, by the selection of an agent characteristic. In one aspect of this embodiment, the conformation of the POZ conjugate is controlled, at least in part, by the selection of an agent with a low solubility in water (for example, a log P value ≥0.5) or an agent that is soluble in water (for example, a log P <0.5). The present disclosure demonstrates that varying the water solubility of the agent modulates the conformation of the POZ conjugate and/or the release rate of an agent from the POZ conjugate, allowing the selection of a release profile for the agent.

In another aspect of this embodiment, the conformation of a POZ conjugate, the cleavage of the agent from the POZ conjugate, the release of the agent from the POZ, and/or selection of a release profile of the agent from the POZ conjugate is controlled, at least in part, by the selection of an agent with a large molecular volume (for example, a molecular volume ≥300) or an agent with a small molecular volume (for example, a molecular volume <300). The present disclosure demonstrates that varying the molecular volume of the agent modulates the conformation of the POZ conjugate and/or the release rate of an agent from the POZ conjugate, allowing the selection of a release profile for the agent.

In another aspect of this embodiment, the conformation of a POZ conjugate, the cleavage of the agent from the POZ conjugate, the release of the agent from the POZ, and/or selection of a release profile of the agent from the POZ conjugate is controlled, at least in part, by the selection of an agent with a high TPSA (for example, a TPSA ≥35) or an agent with a low TPSA (for example, a TPSA <35). The present disclosure demonstrates that varying the TPSA of the agent modulates the conformation of the POZ conjugate and/or the release rate of an agent from the POZ conjugate, allowing the selection of a release profile for the agent.

In one embodiment, the conformation of a POZ conjugate, the cleavage of the agent from the POZ conjugate, the release of the agent from the POZ, and/or selection of a release profile of the agent from the POZ conjugate is controlled, at least in part, by the selection of a loading characteristic (i.e., loading percentage). The loading percentage may be determined by varying the "o" parameter versus the total molecular weight of the POZ conjugate. In one aspect of this embodiment, the conformation of the POZ conjugate is controlled, at least in part, by selection of a high loading percentage of the agent (for example, a loading percentage ≥4% and ≤20%) or selection of a low loading percentage (for example, a loading percentage <4%). The present disclosure demonstrates that varying the loading percentage of the agent modulates the conformation of the POZ conjugate and/or the release rate of an agent from the POZ conjugate, allowing the selection of a release profile for the agent.

Any of the parameters described in the preceding section may be used above.

In one embodiment, a POZ conjugate of the present disclosure has the general formula I, or a pharmaceutically acceptable form thereof:

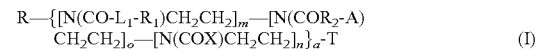

wherein

R is an initiating group;

$R_1$ is a hydrophilic or hydrophobic pendent moiety of a pendent moiety containing a hydrophilic or hydrophobic portion;

$L_1$ is a linking group linking $R_1$ to the POZ polymer or is absent;

$R_2$ is a direct bond of linking group linking the POZ polymer and A;

X is a pendent group;

A is an agent;

a is ran which indicates a random copolymer or block which indicates a block copolymer;

m is an integer from 0 to 100;

n is an integer from 0 to 1000, provided that if m is 0, then is an integer from 1 to 1000;

is an integer from 1 to 50; and

T is a terminating group.

In one embodiment, m is 0. In one embodiment, m is an integer from 1 to 50 or from 1 to 10.

In one embodiment, o is an integer from 1 to 20 or from 1 to 10.

In one embodiment, n is an integer from 0 to 500, from 0 to 250, 50 to 500, from 50 to 250, or from 100 to 200.

In one embodiment, m is an integer from 1 to 50 and o is an integer from 1 to 20 or from 1 to 10. In one aspect of such an embodiment, n is an integer from 0 to 500, from 0 to 250, 50 to 500, from 50 to 250, or from 100 to 200. In one embodiment, m is an integer from 1 to 10 and o is an integer from 1 to 20 or from 1 to 10. In one aspect of such an embodiment, n is an integer from 0 to 500, from 0 to 250, 50 to 500, from 50 to 250, or from 100 to 200.

R is the initiating group and is derived from the cationic initiator that is used to initiate the POZ polymer living cationic polymerization. Therefore, the identity of the R group is dependent on the selection of the cationic initiator. Exemplary R groups include, but are not limited to, hydrogen, unsubstituted alkyl and substituted alkyl. In one embodiment, the initiating group is an alkyl group, such as a $C_1$ to $C_4$ alkyl group. In a specific embodiment of the foregoing, the initiating group is a methyl group. In another embodiment, the initiating group is H. In yet another embodiment, the initiating group is selected to lack a functional group. Additional exemplary initiating groups are disclosed in U.S. Pat. Nos. 7,943,141, 8,088,884, 8,110,651 and 8,101,706, each of which is incorporated herein by reference for such teachings.

$R_1$, when present, is selected to modulate the release rate of an agent from the POZ conjugate. As discussed above, $R_1$ is a pendent moiety containing a hydrophilic or hydrophobic portion. In certain embodiments, $R_1$ may contain a single hydrophilic or hydrophobic portion or more than 1 hydrophilic or hydrophobic portion. When $R_1$ contains more than 1 hydrophilic or hydrophobic portions, the number may be from 2 to 8.

In a particular embodiment, $R_1$ is $L_1$-$R_1$, wherein $L_1$ is a linking group linking the POZ conjugate and $R_1$. In certain embodiments, $L_1$ may contain one or more hydrophilic or hydrophobic portions, such as from 2 to 7 hydrophilic portions. In certain embodiments, $L_1$ contains at least one or at least 2 hydrophilic or hydrophobic portions. In certain embodiments, $L_1$ does not contain a hydrophilic or hydrophobic portions. In certain embodiments, $L_1$ comprises a physiologically degradable linkage. In certain embodiments, $L_1$ does not contain a physiologically degradable linkage.

A variety of hydrophilic groups or compounds may be used. Such hydrophilic groups may be introduced after the POZ polymer is synthesized. In one embodiment, $R_1$ is independently selected for each repeating unit from a water soluble polymer, a substituted alkyl, a substituted alkenyl, a substituted alkynyl, a substituted aralkyl or a substituted heterocyclylalkyl group. In another embodiment, R1 is independently selected for each repeating unit from a $C_1$ to $C_5$ substituted alkyl, substituted alkenyl, or substituted alkynyl. In another embodiment, R1 is independently selected for each repeating unit from a polar alkyl, polar alkenyl, or polar alkynyl, particularly a $C_1$ to $C_5$ polar alkyl, polar alkenyl, or polar alkynyl. In another embodiment, R1 is independently selected for each repeating unit from a water soluble polymer, a substituted alkyl and a polar alkyl, particularly a $C_1$ to $C_5$ substituted alkyl or polar alkyl. In another embodiment of the POZ conjugate of formula I, R1 is independently selected for each POZ repeating unit from a $C_1$ to $C_5$ alcohol. In another embodiment of the POZ conjugate of formula I, R1 is independently selected for each POZ repeating unit from a $C_2$ to $C_4$ alcohol. In another embodiment of the POZ conjugate of formula I, $R_1$ is independently selected for each POZ repeating unit from a $C_1$ to $C_5$ carboxylic acid. In another embodiment of the POZ conjugate of formula I, R1 is independently selected for each POZ repeating unit from a $C_2$ to $C_4$ carboxylic acid. In one embodiment, when $R_1$ is substituted alkyl, substituted alkenyl, substituted alkynyl, substituted aralkyl and/or substituted heterocyclylalkyl, $R_1$ contains one or more oxygen, nitrogen, sulfur and/or phosphorous atoms. In one embodiment, $R_1$ contains one or more polar covalent bonds (such as, but not limited to, a C=O, C—N, C≡N, O—H, and/or C-halogen bonds).

A variety of hydrophobic groups or compounds may be used. Such hydrophobic groups may be introduced via the POZ polymer polymerization process (i.e., as a substituent on the 2-oxazoline monomers) or may be introduced after the POZ polymer is synthesized, or by a combination of the foregoing. In one embodiment, R1 is independently selected for each repeating unit from a C5 to C20 substituted alkyl, substituted alkenyl, substituted alkynyl, substituted aralkyl or substituted heterocyclylalkyl group. In another embodiment, R1 is independently selected for each repeating unit from a C5 to C20 substituted alkyl, substituted aralkyl or substituted heterocyclylalkyl group. In another embodiment, R1 is independently selected for each repeating unit from a C5 to C20 unsubstituted alkyl, unsubstituted alkenyl, unsubstituted alkynyl, unsubstituted aralkyl or unsubstituted heterocyclylalkyl group. In another embodiment, R1 is independently selected for each repeating unit from a C5 to C20 unsubstituted alkyl, unsubstituted aralkyl or unsubstituted heterocyclylalkyl group. Preferably, the hydrophobic group or compound is not a polar alkyl, polar alkenyl, or polar alkynyl.

When R1 is a water soluble polymer, any water soluble polymer may be used. Suitable water soluble polymers include, but are not limited to, POZ, a poly(alkylene glycol), a copolymer of poly(alkylene glycol), a poly(oxyethylated polyol), a poly(olefinic alcohol), a poly(vinylpyrrolidone), a poly(hydroxyalkylmethacrylamide), a poly(hydroxyalkylmethacrylate), a poly(saccharides), a poly(a-hydroxy acid), a poly(vinyl alcohol), a polyphosphazene, a polyoxazoline, a poly(N-acryloylmorpholine), or a combination of any of the foregoing. In a particular embodiment, the water soluble polymer is selected from the group consisting of: polyethylene glycol, poly(propylene glycol), copolymers of ethylene glycol and propylene glycol, and POZ. In one embodiment of any of the foregoing, the water soluble polymer contains from 1 to 30 repeating units, such as from 1 to 20, 1 to 15, 1 to 10, 1 to 9, 1 to 8, 1 to 7, 1 to 6, 1 to 5, 1 to 4, 1 to 3, or 1 to 2.

In certain embodiments, at least one hydrophilic or hydrophobic portion of $R_1$ is located within 50 angstroms from the N group to which $R_1$ is linked. In certain embodiments, when $R_1$ contains more than 1 hydrophilic or hydrophobic portion, at least 2 hydrophilic or hydrophobic portions of $R_1$ are located within 50 angstroms from the N group to which $R_1$ is linked. In certain embodiments, all of the hydrophilic or hydrophobic portions of $R_1$ is located within 50 angstroms from the N group to which $R_1$ is linked.

In certain embodiments, at least one hydrophilic or hydrophobic portion of $R_1$ is located within 30 angstroms from the N group to which $R_1$ is linked. In certain embodiments, when $R_1$ contains more than 1 hydrophilic or hydrophobic portion, at least 2 hydrophilic portions of $R_1$ are located within 30 angstroms from the N group to which $R_1$ is linked. In certain embodiments, all of the hydrophilic or hydrophobic portions of $R_1$ is located within 30 angstroms from the N group to which $R_1$ is linked.

In certain embodiments, at least one hydrophilic or hydrophobic portion of $R_1$ is located within 20 angstroms from the N group to which $R_1$ is linked. In certain embodiments, when $R_1$ contains more than 1 hydrophilic or hydrophobic portion, at least 2 hydrophilic portions of $R_1$ are located within 20 angstroms from the N group to which $R_1$ is linked. In certain embodiments, all of the hydrophilic or hydrophobic portions of $R_1$ is located within 20 angstroms from the N group to which $R_1$ is linked.

In certain embodiments, $R_1$ is an inert group.

X is a pendant group. In one embodiment, X is selected to be non-reactive (i.e., inert). In another embodiment, X is selected to be reactive (i.e., contain a reactive functional group). In one embodiment, X is independently selected for each repeating unit from an unsubstituted or substituted alkyl, an unsubstituted or substituted alkenyl, an unsubstituted or substituted aralkyl or an unsubstituted or substituted heterocyclylalkyl group. In one embodiment, X is independently selected for each repeating unit from an unsubstituted alkyl, an unsubstituted alkenyl, an unsubstituted aralkyl or an unsubstituted heterocyclylalkyl group. In another embodiment, X is an unsubstituted alkyl. In another embodiment, X is a C1 to C20 unsubstituted alkyl. In another embodiment, X is a C1 to C10 unsubstituted alkyl. In another embodiment, X is a C1 to C5 unsubstituted alkyl. In another embodiment, X is a C1 to C2 unsubstituted alkyl. In a particular embodiment, X is methyl, ethyl, propyl or butyl or X is methyl or ethyl.

In another embodiment, when m is 0, X is independently selected for each repeating unit from an unsubstituted or substituted alkyl, an unsubstituted or substituted alkenyl, an unsubstituted or substituted aralkyl or an unsubstituted or substituted heterocyclylalkyl group, preferably unsubstituted. In another embodiment, when m is 0, X is independently selected for each repeating unit from an unsubstituted or substituted alkyl, an unsubstituted or substituted aralkyl or an unsubstituted or substituted heterocyclylalkyl group, preferably unsubstituted.

In another embodiment, when m is 0, X is independently selected for each repeating unit from an unsubstituted or substituted alkyl, an unsubstituted or substituted aralkyl or an unsubstituted or substituted heterocyclylalkyl group, preferably unsubstituted, wherein up to 90% of the X groups (i.e., 90% of n) are C5 to C20 unsubstituted or substituted alkyl, unsubstituted or substituted aralkyl or unsubstituted or substituted heterocyclylalkyl group (preferably unsubstituted) and the remainder of the X groups (i.e., 50% of n) are C1 to C4 unsubstituted or substituted alkyl, unsubstituted or substituted aralkyl or unsubstituted or substituted heterocyclylalkyl group (preferably unsubstituted).

In another embodiment, when m is 0, X is independently selected for each repeating unit from an unsubstituted or substituted alkyl, an unsubstituted or substituted aralkyl or an unsubstituted or substituted heterocyclylalkyl group, preferably unsubstituted, wherein up to 50% (for example, 5%, 10%, 15%, 20%, or 25%) of the X groups are C5 to C20 unsubstituted or substituted alkyl, unsubstituted or substituted aralkyl or unsubstituted or substituted heterocyclylalkyl group (preferably unsubstituted) and the remainder of the X groups (i.e., 50% of n) are C1 to C4 unsubstituted or substituted alkyl, unsubstituted or substituted aralkyl or unsubstituted or substituted heterocyclylalkyl group (preferably unsubstituted).

The terminating group may be any nucleophilic group that is capable of terminating the POZ polymer living cationic polymerization. In one embodiment, T is a thioalkyl carboxylic acid, a thiocarboxylic ester, or a hydroxyl.

In one embodiment, T is Z-B-Q, wherein Z is S, O, or N; B is an optional linking group; and Q is a terminating nucleophile or a terminating portion of a nucleophile. In certain embodiments, Q is inert (i.e., does not contain a functional group); in other embodiments, Q contains a functional group.

Exemplary B groups include, but are not limited to, alkylene groups. In a particular embodiment, B is $-(CH_2)_y-$ where y is an integer selected from 1 to 16. In certain embodiments, y is an integer selected from 1 to 10, 1 to 8, 1 to 6, or 1 to 4. In certain embodiments, y is 2. In a particular embodiment, Z is S. POZ conjugates containing a sulfur group as described herein may be prepared by terminating the cation at the end of the poly oxazoline polymer with a mercaptide reagent, such as, but not limited to, a mercapto-ester (for example, $-S-CH_2CH_2-CO_2CH_3$ or $-S-CH_2CH_2-CO_2H$), an amine (for example, $-S-CH_2CH_2-NH_2$) or mercapto-protected amine (for example, $-S-CH_2CH_2-NH-tBoc$). Such POZ conjugates provide for effective, large-scale purification by ion-exchange chromatography (to remove secondary amines), as well as allowing for control of polydispersity values (with polydispersity values of 1.10 or less) and for the creating POZ conjugates with higher molecular weight POZ polymers. In another embodiment, Z is N. In a further embodiment, Z is O.

As stated above, Q may be inert or may contain a functional group. When Q contains a functional group, exemplary functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). When Q contains a functional group, the functional group may be chemically orthogonal to one or more or all other functional groups present on the conjugate. When Q is a non-reactive group, any non-reactive group may be used, including, but not limited to unsubstituted alkyl and $-C_6H_5$.

The nature of the agents is described in more detail herein. In one embodiment A is a compound comprising a phenolic group. The agent may be any compound useful in the treatment of a disease or condition or the diagnosis of a disease or condition. In certain embodiments, the agent is a diagnostic agent or a therapeutic agent. In certain embodiments, the therapeutic agent is an organic small molecule or a polypeptide.

In one embodiment, the agent is a compound useful in the treatment of PD or other diseases or conditions related to dopamine insufficiency in the peripheral or central nervous system.

In one embodiment, the agent is a compound useful in the treatment of a disorder benefiting from agonism or antagonism of a CB1 receptor, CB2 receptor, 5H1-a receptor, 5H2-a receptor, TRP-V1 receptor, TRP-V2 receptor, TRP-V3 receptor, adenosine A2A receptor, GPR55 receptor, GPR18 receptor, PPAR-α, PPAR-γ receptor, or a combination of the foregoing.

In one embodiment, the agent is a compound useful in the treatment of a disease or condition is selected from the group consisting of: pain, acute pain, chronic pain, neuropathic pain, cancer pain, neurodegenerative disease, post-traumatic stress disorder, agitation associated with dementia, insomnia, REM sleep behavior disorder, excessive daytime sleepiness, nightmares associated with posttraumatic stress disorder, obstructive sleep apnea, essential tremor, Tourette syndrome, depression, fibromyalgia, ischemic disease, stroke, cardiac ischemia, coronary artery disease, thromboembolism, myocardial infarction, brain injury, traumatic brain injury, diffuse axonal injury, concussion, contusion, anoxic brain injury, hypoxic brain injury, age related inflammatory disease, age related autoimmune disease, cachexia, AIDS wasting disease, weight loss associated with cancer, weight loss associated with chronic obstructive pulmonary disease, weight loss associated with infectious disease, nausea, vomiting, glaucoma, movement disorders, rheumatoid arthritis, asthma, allergy, psoriasis, Crohn's disease, systemic lupus erythematosus, diabetes, cancer, osteoporosis, renal ischemia, and nephritis.

In one embodiment, the agent is a compound useful in the treatment of a neurodegenerative disease is selected from the group consisting of: Alzheimer's disease, Parkinson's disease, amyotrophic lateral sclerosis, Huntington's disease, multiple sclerosis, multiple sclerosis ataxia/spasticity syndrome, dystonia associated with Parkinson's disease, dystonia associated with Huntington's disease, frontotemporal dementia, prion disease, Lewy body dementia, motor neuron disease, spinomuscular atrophy, spinocerebellar ataxia, progressive supranuclear palsy, Fragile X-associated tremor/ataxia syndrome, Fragile X-associated behavioral abnormalities, autism spectrum disorder, vascular dementia, normal pressure hydrocephalus, traumatic spinal cord injury, HIV dementia, alcohol induced neurotoxicity, Down's syndrome, epilepsy, partial seizures, generalized seizures, tonic-clonic seizures, absence seizures, atonic seizures, treatment-resistant epilepsy, Lennox-Gastaut syndrome, Dravet syndrome, Ohtahara syndrome, West syndrome, Doose syndrome, CDKL5 encephalopathy, Landau-Kleffner syndrome, hypoxic-ischemic encephalopathy, early myoclonic epilepsy, Rhett's syndrome, and febrile infection related epilepsy syndrome.

In certain embodiments, $R_2$ is a direct bond between the agent and a functional group (for example, those functional groups described herein) on the POZ polymer portion such that a physiologically degradable linkage is produced. In certain embodiments, $R_2$ is a linking group $L_2$ that links the agent to the POZ polymer portion, wherein $L_2$ contains a physiologically degradable linkage (which includes formation of the physiologically degradable linkage through the linkage of the agent to $L_2$). In certain preferred embodiments, the agent is linked to the POZ polymer portion through $L_2$.

In one embodiment, $R_1$ is $R_1$-$L_1$ and $L_1$ optionally contains a physiologically degradable linkage, $R_2$ is $L_2$ and $L_2$ contains a physiologically degradable linkage.

In one embodiment, $R_1$ is $R_1$-$L_1$ and $L_1$ optionally contains a physiologically degradable linkage, $R_2$ is $L_2$ and $L_2$ contains a physiologically degradable linkage, and:
Z is S, B is —$(CH_2)_3$,- and Q is —COOH; Z is O, B is —$(CH_2)_y$— and Q is —COOH; or Z is N, B is —$(CH_2)_y$— and Q is —COOH; Z is S, B is —$(CH_2)_y$— and Q is —$COOCH_3$; Z is O, B is —$(CH_2)_y$— and Q is —$COOCH_3$; or Z is N, B is —$(CH_2)_y$— and Q is —$COOCH_3$; or
Z is S, B is —$(CH_2)_y$— and Q is —$NH_2$; Z is O, B is —$(CH_2)_y$— and Q is —$NH_2$; or Z is N, B is —$(CH_2)_y$— and Q is —$NH_2$.

In any of the foregoing embodiments, the cleavable moiety of the physiologically degradable linkage may be an ester group. In any of the foregoing, y is 1-3.

In any the foregoing embodiments, $L_1$ and $L_2$, when present, may include components of a group that was originally present on the POZ polymer and/or $R_1$ or the agent, respectively. Suitable parameters for $L_1$ and $L_2$ are described herein. In any the foregoing embodiments, $L_1$ contains a physiologically degradable linkage. In any the foregoing embodiments, $L_1$ does not contain a physiologically degradable linkage. In any the foregoing embodiments, $L_2$ contains a physiologically degradable linkage.

In any of the foregoing embodiments, control of the release rate of the agent from the POZ conjugate provides the ability to select a release profile for the agent. As discussed above, in certain embodiments, the release rate of the agent from the POZ conjugate is controlled by the selection of $R_1$, the hydrophobic character of the pendent groups (particularly when m is 0), the selection of the agent, the selection of m (i.e., the loading percentage), the selection of n and optionally m and/or o (i.e., the molecular weight of the POZ polymer portion), or a combination of the foregoing.

In any of the foregoing embodiments, the release profile is sustained over a period of 12 hours to 24 hours. In any of the foregoing embodiments, the release profile is sustained over a period of 12 hours to 48 hours. In any of the foregoing embodiments, the release profile is sustained over a period of 12 hours to 72 hours. In any of the foregoing embodiments, the release profile is sustained over a period of 12 hours to 96 hours. In any of the foregoing embodiments, the release profile is sustained over a period of 12 hours to 120 hours. In any of the foregoing embodiments, the release profile is sustained over a period of 12 hours to 144 hours. In any of the foregoing embodiments, the release profile is sustained over a period of 12 hours to 168 hours.

In any of the foregoing embodiments, the release profile is sustained over a period of one week or more. In any of the foregoing embodiments, the release profile is sustained over a period of one to two weeks. In any of the foregoing embodiments, the release profile is sustained over a period of one to three weeks. In any of the foregoing embodiments, the release profile is sustained over a period of one to four weeks.

In any of the foregoing, the release profile over any of the foregoing periods of time exhibits zero-order release kinetics.

L Groups

In certain embodiments described above, the agent and/or $R_1$ are linked to the POZ polymer portion through a linkage $L_2$ and $L_1$, respectively, wherein $L_2$ contains a physiologically degradable linkage and $L_1$ optionally contains a physiologically degradable linkage. In certain embodiments, $L_2$ is the same for each repeating unit of the POZ polymer portion and/or $L_1$ is the same for each repeating unit of the POZ polymer portion. In certain embodiments, $L_1$ and $L_2$ are the same for each repeating unit of the POZ polymer portion. Exemplary cleavable moieties that may be contained in the physiologically degradable linkage include, but are not limited to, esters, carboxylate esters (—C(O)—O—), carbonate esters (—O—C(O)—O—), carbamates (—O—C(O)—NH—), amides (—C(O)—NH—), disulfides (S—S), and peptides (for example, peptides from 2 to 10 amino acids); other cleavable moieties are discussed herein. In a particular embodiment, the cleavable moiety is an ester group. In another particular embodiment, the cleavable moiety is a carboxylate ester.

In one embodiment, the $L_2$ is a di-substituted triazole that contains a first cleavable moiety in one of the $R_3$ or $R_4$ groups, preferably in the $R_4$ group.

In a specific embodiment, the di-substituted triazole has the structure:

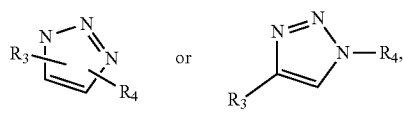

wherein:
$R_3$ is a linker linking the triazole moiety to the POZ polymer chain. $R_3$ may be defined in part by the functional group on the polymer chain; in other words, $R_3$ may contain a part of the functional group on the polymer chain. In one embodiment, $R_3$ is —C(O)—$R_5$—, wherein: (i) $R_5$ is absent; (ii) $R_5$ is an unsubstituted or substituted alkyl, an unsubstituted or substituted alkenyl, an unsubstituted or substituted aralkyl or an unsubstituted or substituted heterocyclylalkyl group; (iii) $R_5$ is an unsubstituted alkyl, an unsubstituted alkenyl, an unsubstituted aralkyl or an unsubstituted heterocyclylalkyl group; (iv) $R_5$ is an unsubstituted alkyl; (v) or $R_5$ is a straight chain unsubstituted alkyl. In any of the foregoing (i) to (v), the unsubstituted or substituted alkyl or unsubstituted or substituted alkenyl may be from 1 to 10 carbons in length or 1 to 5 carbons in length.

$R_4$ is a linker linking the triazole moiety to the agent. $R_4$ may be defined in part by the functional group on the agent; in other words, $R_4$ may contain a part of the group/functional group on the agent, such as, for example, an O atom of a phenolic hydroxyl group. In one embodiment, $R_4$ is —$R_6$—$R_7$—$R_8$—, where $R_6$ is a substituted or unsubstituted alkyl, substituted or unsubstituted aralkyl or a oligo(ethylene oxide) (for example, —(CH$_2$CH$_2$O)$_e$— where e is and integer from 1-10 or 1-4), $R_7$ is a group containing the cleavable moiety or a portion of the cleavable moiety and $R_5$ is absent or O. In certain embodiments, $R_7$ and $R_5$ may combine to form the cleavable moiety. In one embodiment, $R_7$ is —$R_a$—C(O)—$R_b$—, —$R_a$—O—C(O)—$R_b$—, —$R_a$—C(O)—O—$R_b$, —$R_a$—C(O)—NH-cyclic-O—C(O)—$R_b$— (where cyclic represents substituted or unsubstituted aryl, heterocylalkyl, heteroaryl, heterocyclyl or cycloalkyl), —$R_a$—C(O)—NH—(C$_6$H$_4$)—O—C(O)—$R_b$—, —$R_a$—O—C(O)—NR$_{10}$—$R_b$— (where $R_{10}$ is a is H or a substituted or unsubstituted C1-05 alkyl), —$R_a$—CH(OH)—O—$R_b$—, —$R_a$—S—S—$R_b$—, —$R_a$—O—P(O)(OR$_9$)—O—$R_b$— (where $R_9$ is H or a substituted or unsubstituted C1-05 alkyl), or —$R_a$—C(O)—NR$_{10}$—$R_b$— (where $R_{10}$ is a is H or a substituted or unsubstituted C1-05 alkyl), where $R_a$ and $R_b$ are each independently absent or substituted or unsubstituted alkyl. In another embodiment, $R_a$ and $R_b$ are each independently absent or a C1-C16 or C1-C6 substituted or unsubstituted alkyl.

In one embodiment of the foregoing, R6 is a straight chain substituted or unsubstituted C1-C10 alkyl or a branched substituted or unsubstituted C1-C10 alkyl, $R_7$ is —$R_a$—C(O)—$R_b$— and $R_8$ is —O—. In one embodiment of the foregoing, $R_6$ is a straight chain substituted or unsubstituted C1-C10 alkyl or a branched substituted or unsubstituted C1-C10 alkyl, $R_7$ is —$R_a$—C(O)—O—$R_b$— and $R_8$ is absent. In any of the foregoing Ra and Rb are absent.

In one embodiment of the foregoing, $R_6$ is a straight chain substituted or unsubstituted C1-C4 alkyl or a branched substituted or unsubstituted C1-C4 alkyl, $R_7$ is —$R_a$—C(O)—$R_b$— and $R_8$ is —O—. In one embodiment of the foregoing, $R_6$ is a straight chain substituted or unsubstituted C1-C4 alkyl or a branched substituted or unsubstituted C1-C4 alkyl, $R_7$ is —$R_a$—C(O)—O—$R_b$— and $R_8$ is absent. In any of the foregoing $R_a$ and $R_b$ are absent.

In a particular embodiment, $R_3$ is —C(O)—(CH$_2$)$_3$ and $R_4$ is —(CH$_2$)$_d$—C(O)—O—, —CH$_2$—C(O)—O—CH$_2$—CH$_2$—C(O)—O—, —CH$_2$—CH$_2$—CH$_2$—C(O)—O—, —CH$_2$(CH$_3$)—C(O)—O—, wherein d is an integer from 1 to 10, or a combination of the foregoing.

In a particular embodiment, $R_3$ is —C(O)—(CH$_2$)$_3$ and $R_4$ is —(CH$_2$)$_d$—C(O)—, —CH$_2$—C(O)—, —CH$_2$—CH$_2$—C(O)—, —CH$_2$—CH$_2$—CH$_2$—C(O)—, —CH$_2$(CH$_3$)—C(O)—, wherein d is an integer from 1 to 10, or a combination of the foregoing.

In one embodiment, the $L_1$ is a di-substituted triazole that optionally contains a first cleavable moiety in one of the $R_3$ or $R_4$ groups, preferably in the $R_4$ group when the cleavable moiety is present.

In a specific embodiment, the di-substituted triazole has the structure:

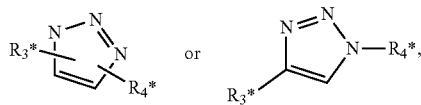

wherein:
$R_3$* is a linker linking the triazole moiety to the POZ polymer chain. $R_3$* may be defined in part by the functional group on the polymer chain; in other words, $R_3$* may contain a part of the functional group on the polymer chain. In one embodiment, $R_3$* is —C(O)—$R_5$*—, wherein $R_5$*: (i) is absent; (ii) is an unsubstituted or substituted alkyl, an unsubstituted or substituted alkenyl, an unsubstituted or substituted aralkyl or an unsubstituted or substituted heterocyclylalkyl group; (iii) is an unsubstituted alkyl, an unsubstituted alkenyl, an unsubstituted aralkyl or an unsubstituted heterocyclylalkyl group; (iv) is an unsubstituted alkyl; or (v) is a straight chain unsubstituted alkyl. In any of the foregoing (i) to (v), the unsubstituted or substituted alkyl or unsubstituted or substituted alkenyl may be from 1 to 10 carbons in length or 1 to 5 carbons in length.

$R_4$* is $R_1$ or a linker linking the triazole moiety to $R_1$. When $R_4$* is a linker linking the triazole moiety to $R_1$, $R_4$* may be as described for $R_4$ in $L_2$ above.

In a particular embodiment, $R_3$* is —C(O)—(CH$_2$)$_3$ and $R_1$ is a C1 to C5 alcohol, a C1 to C5 carboxylic acid, a C1 to C5 substituted or unsubstituted alkyl, alkenyl, or alkynyl, a C1 to C5 substituted or unsubstituted polar alkyl, polar alkenyl, or polar alkynyl, or a combination of the foregoing.

In a particular embodiment, $R_3$* is —C(O)—(CH$_2$)$_3$ and $R_1$ is a C1 to C5 alcohol, a C1 to C5 carboxylic acid, or a combination of the foregoing.

POZ Conjugate Properties

The POZ polymer characteristic, the agent characteristics, and the loading characteristics described in the section titled "Compositions and Methods for Controlling the Conformation of a POZ Conjugate and Modulating the Release Rate of an Agent From a POZ Conjugate" are applicable to the POZ conjugates described herein. Each may be applied individually or they may be applied in combination.

In one embodiment, when it is desired to inhibit the formation of the compact conformation and/or increase the rate of release of an agent from the POZ conjugate, the POZ conjugate has a loading percentage for the agent from 4% to 20%. In certain embodiments, the POZ conjugate has a loading percentage for the agent ≥4.0% and ≤16.0% or a loading percentage for the agent ≥6.0% and ≤10.0%. In certain embodiments, the POZ conjugate has a loading percentage ≥4.0%, ≥5.0%, ≥6.0%, ≥7.0%, ≥8.0%, ≥9.0%, ≥10.0%, ≥11.0%, ≥12.0%, ≥13.0%, ≥14.0%, ≥15.0%, or ≥16.0% (in each of the foregoing the loading percentage being ≤20.0%).

In one embodiment, when it is desired to inhibit the formation of the compact conformation and/or increase the rate of release of an agent from the POZ conjugate, the POZ conjugate has a loading percentage of the agent <4%. In one embodiment, when it is desired to inhibit the formation of the compact conformation and/or increase the rate of release of an agent from the POZ conjugate, the POZ conjugate has a loading percentage for the agent of less than 4%. In certain embodiments, the POZ conjugate has a loading percentage for the agent <4.0% or a loading percentage for the agent ≥1.0% and ≤4.0%.

In one embodiment, when it is desired to stimulate the formation of the compact conformation and/or decrease the rate of release of an agent from the POZ conjugate, the POZ polymer portion of the POZ conjugate has a molecular weight of ≥20 kDa. In one embodiment, the POZ polymer portion has a molecular weight of 25 kDa, 30 kDa, 35 kDa, 40 kDa, 45 kDa, 50 kDa, 75 kDa, 100 kDa, or 150 kDa. In another embodiment, the molecular weight of the POZ polymer portion is ≥20 kDa and ≤100 kDa. In another embodiment, the molecular weight of the POZ polymer portion is ≥50 kDa and ≤150 kDa.

In one embodiment, when it is desired to inhibit the formation of the compact conformation and/or increase the rate of release of an agent from the POZ conjugate, the POZ conjugate comprises a hydrophilic pendent moiety ($R_1$). $R_1$ may be as described above. In certain embodiments, $R_1$ is a C1 to C5 alcohol, a C1 to C5 carboxylic acid, a C1 to C5 substituted or unsubstituted alkyl, alkenyl, or alkynyl, a C1 to C5 substituted or unsubstituted polar alkyl, polar alkenyl, or polar alkynyl, or a combination of the foregoing. In certain embodiments, $R_1$ is a C1 to C5 alcohol, a C1 to C5 carboxylic acid, or a combination of the foregoing.

In one embodiment, when it is desired to stimulate the formation of the compact conformation and/or decrease the rate of release of an agent from the POZ conjugate, the POZ conjugate comprises pendent groups with a hydrophobic character (for example, pendent groups other than methyl). In another embodiment, particularly when m is 0, X is independently selected for each repeating unit from an unsubstituted or substituted alkyl, an unsubstituted or substituted aralkyl or an unsubstituted or substituted heterocyclylalkyl group, preferably unsubstituted, wherein up to 50% to 90% of the X groups are C5 to C20 unsubstituted or substituted alkyl, unsubstituted or substituted aralkyl or unsubstituted or substituted heterocyclylalkyl group (preferably unsubstituted) and the remainder of the X groups (i.e., 50% of n) are C1 to C4 unsubstituted or substituted alkyl, unsubstituted or substituted aralkyl or unsubstituted or substituted heterocyclylalkyl group (preferably unsubstituted).

In one embodiment, when it is desired to stimulate the formation of the compact conformation and/or decrease the rate of release of an agent from the POZ conjugate, the POZ conjugate comprises a hydrophobic pendent moiety ($R_1$). $R_1$ may be as described above. In one embodiment, $R_1$ is independently selected for each repeating unit from a C5 to C20 unsubstituted alkyl, unsubstituted aralkyl or unsubstituted heterocyclylalkyl group.

Agents

In one embodiment, the agent is a therapeutic agent.

In one embodiment, the agent is a dopamine agonist. Non-limiting examples of dopamine agonists include, but are not limited to, apomorphine, arbutamine, carbidopa, dobutamine, dopamine, entacapone, epinephrine, fenoldopam, isoetharine, isoproterenol, levopoda, levonordefrin, masaprocol, methyldopa, methyldopate, norepinephrine, protokylol, tolcapone, or (r)-(+)-fenoldopam, rotigotine, pramipexole, quinagolide, 5-OH-DPAT, ropinirole, pergolide, cabergoline, or bromocriptine. The foregoing are useful in treating a dopamine responsive condition.

In one embodiment, the agent is an anticholinergic (such as, but not limited to, trihexyphenidyl, biperidin and hyoscyamine), a monamine oxidase-B inhibitor (such as, but not limited to, seligiline and rasagiline), a catechol-O-methyl transferase (COMT) inhibitor (such as, but not limited to, tolcapone and entacapone) or an adenosine $A_{2A}$ receptor antagonist (such as, but not limited to, preladenant, theophylline and istradefylline). The foregoing are useful in treating a dopamine responsive condition.

In one, the agent is a GABA-uptake inhibitor. Non-limiting examples of GABA re-uptake inhibitors are tiagabine and nipecotic acid. The foregoing are useful in treatment of a disorder characterized by excessive GABA re-uptake or GABA re-uptake.

In one embodiment, the agent is a compound isolated from a plant of the *Cannabis* species. In another embodiment, the agent is a phytocannabinoid (a compound that originates from nature and can be found in a plant of the *Cannabis* species). In another embodiment, the agent is a compound listed in Table 1 of Brenneisen (Chapter 2, Forensic Science and Medicine: Marijuana and the Cannabinoids; M. A. ElSohly ed, Humana Press, Inc., Townsend NJ). In another embodiment, the agent is cannabidiol, cannabigerol, cannabigerolic acid, cannabidiolic acid, cannabidiolmonomethylether, cannabidiol-C4, cannabidarinic acid, cannabidivarin, cannabidiol or cannabigerol propyl variant, cannabichromene, cannabichromenic acid, cannabichromevarinic acid, cannabichromevarin, cannabinol, cannabicyclol, tetrahydrocannabivarin, $\Delta^9$-THC, ajulemic acid, and dexanabinol.

In one embodiment the agent is buprenorphine. In another embodiment, the agent is an analogue of buprenorphine. Suitable analogues of buprenorphine include, but are not limited to, BU08028 (as disclosed in Li, PNAS 113(37), 10225-10227, 2016), a compound disclosed in WO/2014/087226, WO/2013/084060, or WO/2012/084060, or HS-559.

In one embodiment, the agent is useful in treating a dopamine responsive condition, including, but not limited to, a disease or condition related to dopamine insufficiency in the peripheral or central nervous system. In another embodiment, the agent is useful in the treatment of Parkinson's disease, restless leg syndrome, schizophrenia, attention-deficit hyperactivity disorder, hypodopaminergic conditions, SSRI-induced sexual dysfunction, depression, obesity, and type II diabetes. Other diseases and conditions that may be treated are described in Rubi et al. (Endocrinology, 151(12), 5570-5581, 2010).

In one embodiment, the agent is a compound useful in the treatment of a disorder characterized by excessive GABA re-uptake or GABA re-uptake. In a particular embodiment, the agent is a compound useful for the treatment of anxiety disorders, social anxiety disorders, panic disorders, neuropathic pain (which includes usefulness in poorly understood disorders like fibromyalgia), chronic pain, muscle tremors, muscle spasms, seizures, convulsions and/or epilepsy.

In one embodiment, the agent is a compound useful in the treatment of a disorder benefiting from agonism or antagonism of a CB1 receptor, CB2 receptor, 5H1-a receptor, 5H2-a receptor, TRP-V1 receptor, TRP-V2 receptor, TRP-V3 receptor, adenosine A2A receptor, GPR55 receptor, GPR18 receptor, PPAR-α, PPAR-γ receptor, or a combination of the foregoing.

In one embodiment, the agent is a compound useful in the treatment of a disease or condition is selected from the group consisting of: pain, acute pain, chronic pain, neuropathic pain, cancer pain, neurodegenerative disease, post-traumatic stress disorder, agitation associated with dementia, insomnia, REM sleep behavior disorder, excessive daytime sleepiness, nightmares associated with posttraumatic stress disorder, obstructive sleep apnea, essential tremor, Tourette syndrome, depression, fibromyalgia, ischemic disease, stroke, cardiac ischemia, coronary artery disease, thromboembolism, myocardial infarction, brain injury, traumatic brain injury, diffuse axonal injury, concussion, contusion, anoxic brain injury, hypoxic brain injury, age related inflammatory disease, age related autoimmune disease, cachexia, AIDS wasting disease, weight loss associated with cancer, weight loss associated with chronic obstructive pulmonary disease, weight loss associated with infectious disease, nausea, vomiting, glaucoma, movement disorders, rheumatoid arthritis, asthma, allergy, psoriasis, Crohn's disease, systemic lupus erythematosus, diabetes, cancer, osteoporosis, renal ischemia, and nephritis.

In one embodiment, the agent is a compound useful in the treatment of a neurodegenerative disease is selected from the group consisting of. Alzheimer's disease, Parkinson's disease, amyotrophic lateral sclerosis, Huntington's disease, multiple sclerosis, multiple sclerosis ataxia/spasticity syndrome, dystonia associated with Parkinson's disease, dystonia associated with Huntington's disease, frontotemporal dementia, prion disease, Lewy body dementia, motor neuron disease, spinomuscular atrophy, spinocerebellar ataxia, progressive supranuclear palsy, Fragile X-associated tremor/ataxia syndrome, Fragile X-associated behavioral abnormalities, autism spectrum disorder, vascular dementia, normal pressure hydrocephalus, traumatic spinal cord injury, HIV dementia, alcohol induced neurotoxicity, Down's syndrome, epilepsy, partial seizures, generalized seizures, tonic-clonic seizures, absence seizures, atonic seizures, treatment-resistant epilepsy, Lennox-Gastaut syndrome, Dravet syndrome, Ohtahara syndrome, West syndrome, Doose syndrome, CDKLS encephalopathy, Landau-Kleffner syndrome, hypoxic-ischemic encephalopathy, early myoclonic epilepsy, Rhett's syndrome, and febrile infection related epilepsy syndrome.

For clarity, the agent may be any of the foregoing classes of compounds or a compound of another class that has appropriate chemical functionality to form a physiologically degradable linkage with a POZ polymer or linking group of the present disclosure. The foregoing examples are presented by way of exemplification and are not intended to be limiting.

Furthermore, the agent may be used to treat a variety of diseases or conditions. The choice of agent should not be limited to the treatment of the exemplified diseases or conditions. Any agent that would benefit from the methods described herein may also be used. The foregoing examples are presented by way of exemplification and are not intended to be limiting.

In one embodiment, when it is desired to stimulate the formation of the compact conformation and/or decrease the rate of release of an agent from the POZ conjugate, the POZ conjugate comprises and agent with a low water solubility. In certain embodiments, an agent with a low water solubility has a log P value of $\geq 0.5$, $\geq 1.0$, $\geq 1.5$, $\geq 2.0$, $\geq 2.5$, $\geq 3.0$, $\geq 3.5$, $\geq 4.0$, $\geq 4.5$, $\geq 5.0$, $\geq 5.5$, $\geq 6.0$, $\geq 6.5$, $\geq 7.0$, $\geq 7.5$, or $\geq 8.0$. In certain embodiments of the foregoing, the agent has a log P value of $\leq 10$. In certain embodiments of the foregoing, the agent has a log P value of $\geq 4.5$ and $\leq 10$.

In one embodiment, when it is desired to inhibit the formation of the compact conformation and/or increase the rate of release of an agent from the POZ conjugate, the POZ conjugate comprises and agent with a high water solubility.

In certain embodiments, an agent with a high water solubility has a log P value of <0.5.

In one embodiment, when it is desired to inhibit the formation of the compact conformation and/or increase the rate of release of an agent from the POZ conjugate, the POZ conjugate comprises and agent with a large molecular volume. In certain embodiments, an agent with a large molecular volume has molecular volume of $\geq 300$, $\geq 350$, $\geq 400$, $\geq 450$, $\geq 500$. In certain embodiments, an agent with a large molecular volume has molecular volume of $\geq 300$ and $\leq 500$. In certain embodiments, an agent with a large molecular volume has molecular volume of $\geq 300$ and $\leq 400$.

In one embodiment, when it is desired to stimulate the formation of the compact conformation and/or decrease the rate of release of an agent from the POZ conjugate, the POZ conjugate comprises and agent with a small molecular volume. In certain embodiments, an agent with a small molecular volume has molecular volume of <300, $\leq 250$, $\leq 200$, $\leq 150$, $\leq 100$, or $\leq 50$. In certain embodiments, an agent with a small molecular volume has molecular volume of $\geq 50$ <300. In certain embodiments, an agent with a small molecular volume has molecular volume of $\geq 100$<300.

In one embodiment, when it is desired to inhibit the formation of the compact conformation and/or increase the rate of release of an agent from the POZ conjugate, the POZ conjugate comprises and agent with a high TPSA. In certain embodiments, an agent with a high TPSA has a TPSA $\geq 35$, $\geq 40$, $\geq 45$, $\geq 50$, $\geq 55$, $\geq 60$, or $\geq 65$. In certain embodiments, an agent with a high TPSA has a TPSA of $\geq 35$ and $\leq 75$. In certain embodiments, an agent with a high TPSA has a TPSA of $\geq 40$ and $\leq 60$.

In one embodiment, when it is desired to stimulate the formation of the compact conformation and/or decrease the rate of release of an agent from the POZ conjugate, the POZ conjugate comprises and agent with a low TPSA. In certain embodiments, an agent with a low TPSA has a TPSA $\leq 30$, $\leq 25$, $\leq 20$, or $\leq 15$. In certain embodiments, an agent with a low TPSA has a TPSA of $\leq 35$ and >15.

Methods of Treatment

The present disclosure also provides for methods of treatment using the methods, POZ conjugates and compositions described herein. In the descriptions of the methods of treatment below, the POZ conjugate may be administered alone or as a part of a composition, preferably a pharmaceutical composition.

In one embodiment, the present disclosure provides a method of treating a disorder as described herein in a subject, the method comprising administering to the subject a dose of a composition comprising a polyoxazoline (POZ) conjugate, or a pharmaceutically acceptable form thereof, according to a dosing interval for a treatment period, the phytocannabinoid-polymer conjugate comprising a water-soluble POZ polymer, a phytocannabinoid linked to the POZ polymer by a physiologically degradable linkage, and an optional pendent moiety containing a hydrophilic or a hydrophobic portion linked to the POZ polymer, wherein the dose contains a therapeutically effective amount of the POZ conjugate.

In certain embodiments, the POZ conjugate contains 1.6%±1.0% to 9.6%±1.0% of the agent (w/w agent to POZ polymer). In certain embodiments, the dose of the composition comprising the POZ conjugate is administered as a single dose. In certain embodiments, the dose of the composition comprising the POZ conjugate is administered in multiple doses.

In certain embodiments, the therapeutically effective amount of the agent in the POZ conjugate ranges from: i)

about 0.05 mg/kg to about 10 mg/kg; ii) about 0.05 mg/kg to about 8 mg/kg; iii) about 0.05 mg/kg to about 6 mg/kg; iv) about 0.05 mg/kg to about 4 mg/kg; v) about 0.05 mg/kg to about 2 mg/kg; or vi) about 0.5 mg/kg to about 8 mg/kg.

In certain embodiments, the therapeutically effective amount of the agent in the POZ conjugate ranges from: i) about 1 mg/kg to about 30 mg/kg; ii) about 1 mg/kg to about 25 mg/kg; iii) about 1 mg/kg to about 20 mg/kg; iv) about 1 mg/kg to about 15 mg/kg; v) about 1 mg/kg to about 10 mg/kg; or vi) about 1 mg/kg to about 5 mg/kg.

In certain embodiments, the therapeutically effective amount of the agent in the POZ conjugate ranges from: i) about 10 mg/kg to about 30 mg/kg; ii) about 10 mg/kg to about 25 mg/kg; iii) about 10 mg/kg to about 20 mg/kg; iv) about 10 mg/kg to about 18 mg/kg; v) about 10 mg/kg to about 16 mg/kg; or vi) about 10 mg/kg to about 14 mg/kg.

In certain embodiments, a plasma concentration of the agent in the subject is greater than a minimum therapeutic level during all or substantially all of the dosing interval or the treatment period. In one aspect of this embodiment, the minimum therapeutic level is 5 ng/ml, 50 ng/ml, 150 ng/ml, 500 ng/ml, 1000 ng/ml, or 1,500 ng/ml.

In certain embodiments, a plasma concentration of the agent in the subject is greater than a minimum therapeutic level during all or substantially all of the dosing interval or the treatment period and a single dose of the POZ conjugate is administered. In certain embodiments, a plasma concentration of the agent in the subject is greater than a minimum therapeutic level during all or substantially all of the dosing interval or the treatment period, multiple doses of the POZ conjugate are administered, and the dose dosing interval is 2 times per week or one time per week. In one aspect of these embodiment, the minimum therapeutic level is 5 ng/ml, 50 ng/ml, 150 ng/ml, 500 ng/ml, 1000 ng/ml, or 1,500 ng/ml.

In certain embodiments, the treatment period is 7 days to 60 months or the treatment period is continuous. In certain embodiments, the dosing interval is every day, every other day, two times per week, one time per week, one time every two weeks or 1 time every 4 weeks.

In one embodiment, the present disclosure provides a method of treating a disorder benefiting from agonism or antagonism of a CB1 receptor, CB2 receptor, 5H1-a receptor, 5H2-a receptor, TRP-V1 receptor, TRP-V2 receptor, TRP-V3 receptor, adenosine A2A receptor, GPR55 receptor, PPAR-$\alpha$, PPAR-$\gamma$ receptor, or a combination of the foregoing in a subject, the method comprising administering to the subject a dose of a composition comprising a polyoxazoline (POZ) conjugate, or a pharmaceutically acceptable form thereof, according to a dosing interval for a treatment period, the phytocannabinoid-polymer conjugate comprising a water-soluble POZ polymer, a phytocannabinoid linked to the POZ polymer by a physiologically degradable linkage, and an optional pendent moiety containing a hydrophilic or a hydrophobic portion linked to the POZ polymer, wherein the dose contains a therapeutically effective amount of the POZ conjugate. In one embodiment, the therapeutically effective amount is 0.25 mg eq/kg to 5 mg eq/kg of the phytocannabinoid.

In certain embodiments, the phytocannabinoid is phytocannabinoid is selected from the group consisting of: cannabidiol, cannabigerol, cannabigerolic acid, cannabidiolic acid, cannabidiolmonomethylether, cannabidiol-C4, cannabidarinic acid, cannabidivarin, cannabidiol or cannabigerol propyl variant, cannabichromene, cannabichromenic acid, cannabichromevarinic acid, cannabichromevarin, cannabinol, cannabicyclol, tetrahydrocannabivarin, $\Delta^9$-THC, ajulemic acid, and dexanabinol.

In certain embodiments, the POZ conjugate contains 1.6%±1.0% to 9.6%±1.0% phytocannabinoid (w/w phytocannabinoid to POZ polymer). In certain embodiments, the POZ conjugate contains 1.6%±1.0% to 9.6%±1.0% CBD (w/w CBD to POZ polymer).

In certain embodiments of any of the methods of treatment described herein, the dose of the composition comprising the POZ conjugate is administered in a single dose. In certain embodiments, the dose of the composition comprising the phytocannabinoid-polymer conjugate is administered in multiple doses.

In certain embodiments, the dose of the POZ conjugate contains between 0.25 mg eq/kg to 2.5 mg eq/kg of the phytocannabinoid. In certain embodiments, the phytocannabinoid is CBD. Such a dose may be delivered as a single dose or in multiple doses.

In certain embodiments, the dose of the POZ conjugate contains between 0.25 mg eq/kg to 2.5 mg eq/kg of the phytocannabinoid, multiple doses of the POZ conjugate are administered, and the dosing interval is 2 times per week or one time per week. In certain embodiments, the phytocannabinoid is CBD.

In certain embodiments, the dose of a POZ conjugate contains between 2.5 mg eq/kg to 5.0 mg eq/kg of the phytocannabinoid. In certain embodiments, the phytocannabinoid is CBD. Such a dose may be delivered as a single dose or in multiple doses.

In certain embodiments, the dose of the POZ conjugate contains between 2.5 mg eq/kg to 5.0 mg eq/kg of the phytocannabinoid, multiple doses of the POZ conjugate are administered, and the dose dosing interval is 2 times per week or one time per week. In certain embodiments, the phytocannabinoid is CBD.

In certain embodiments, a plasma concentration of the phytocannabinoid in the subject is greater than a minimum therapeutic level during all or substantially all of the dosing interval or the treatment period. In one aspect of this embodiment, the minimum therapeutic level is 5 ng/ml, 50 ng/ml, 150 ng/ml, 500 ng/ml, or 1000 ng/ml.

In certain embodiments, a plasma concentration of the phytocannabinoid in the subject is greater than a minimum therapeutic level during all or substantially all of the dosing interval or the treatment period, the dose of the POZ conjugate contains between 2.5 mg eq/kg to 5.0 mg eq/kg of the phytocannabinoid and the dose dosing interval is 2 times per week or one time per week. In one aspect of this embodiment, the minimum therapeutic level is 5 ng/ml, 50 ng/ml, 150 ng/ml, 500 ng/ml, 1000 ng/ml, or 1,500 ng/ml. In another aspect of this embodiment, the phytocannabinoid is CBD.

In certain embodiments, a plasma concentration of the phytocannabinoid in the subject is greater than a minimum therapeutic level during all or substantially all of the dosing interval or the treatment period, the dose of the POZ conjugate contains between 0.25 mg eq/kg to 2.5 mg eq/kg of the phytocannabinoid and the dose dosing interval is 2 times per week or one time per week. In one aspect of this embodiment, the minimum therapeutic level is 5 ng/ml, 50 ng/ml, 150 ng/ml, 500 ng/ml, or 1000 ng/ml. In another aspect of this embodiment, the phytocannabinoid is CBD.

In certain embodiments, the treatment period is 7 days to 60 months or the treatment period is continuous. In certain embodiments, the dosing interval is every day, every other day, two times per week, one time per week, one time every two weeks or 1 time every 4 weeks.

In any of the foregoing embodiments, the disease or condition is selected from the group consisting of: pain, acute pain, chronic pain, neuropathic pain, cancer pain, neurodegenerative disease, post-traumatic stress disorder, agitation associated with dementia, insomnia, REM sleep behavior disorder, excessive daytime sleepiness, nightmares associated with posttraumatic stress disorder, obstructive sleep apnea, essential tremor, Tourette syndrome, depression, fibromyalgia, ischemic disease, stroke, cardiac ischemia, coronary artery disease, thromboembolism, myocardial infarction, brain injury, traumatic brain injury, diffuse axonal injury, concussion, contusion, anoxic brain injury, hypoxic brain injury, age related inflammatory disease, age related autoimmune disease, cachexia, AIDS wasting disease, weight loss associated with cancer, weight loss associated with chronic obstructive pulmonary disease, weight loss associated with infectious disease, nausea, vomiting, glaucoma, movement disorders, rheumatoid arthritis, asthma, allergy, psoriasis, Crohn's disease, systemic lupus erythematosus, diabetes, cancer, osteoporosis, renal ischemia, and nephritis.

In any of the foregoing embodiments, the neurodegenerative disease is selected from the group consisting of: Alzheimer's disease, Parkinson's disease, amyotrophic lateral sclerosis, Huntington's disease, multiple sclerosis, multiple sclerosis ataxia/spasticity syndrome, dystonia associated with Parkinson's disease, dystonia associated with Huntington's disease, frontotemporal dementia, prion disease, Lewy body dementia, motor neuron disease, spinomuscular atrophy, spinocerebellar ataxia, progressive supranuclear palsy, Fragile X-associated tremor/ataxia syndrome, Fragile X-associated behavioral abnormalities, autism spectrum disorder, vascular dementia, normal pressure hydrocephalus, traumatic spinal cord injury, HIV dementia, alcohol induced neurotoxicity, Down's syndrome, epilepsy, partial seizures, generalized seizures, tonic-clonic seizures, absence seizures, atonic seizures, treatment-resistant epilepsy, Lennox-Gastaut syndrome, Dravet syndrome, Ohtahara syndrome, West syndrome, Doose syndrome, CDKL5 encephalopathy, Landau-Kleffner syndrome, hypoxic-ischemic encephalopathy, early myoclonic epilepsy, Rhett's syndrome, and febrile infection related epilepsy syndrome.

In another embodiment, the present disclosure provides a method of treating a disorder characterized by excessive GABA re-uptake or GABA re-uptake in a subject, the method comprising administering to the subject a dose of a composition comprising a therapeutically effective amount of a polyoxazoline (POZ) conjugate, or a pharmaceutically acceptable form thereof, the POZ conjugate comprising a water-soluble POZ polymer, a GABA re-uptake inhibitor linked to the POZ polymer by a physiologically degradable linkage, and an optional pendent moiety containing a hydrophilic or a hydrophobic portion linked to the POZ polymer.

In one embodiment, the dose is administered according to a dosing interval for a treatment period. In certain embodiments, the treatment period is 7 days to 60 months or the treatment period is continuous. In certain embodiments, the dosing interval is every day, every other day, two times per week, one time per week, one time every two weeks or 1 time every 4 weeks.

In one embodiment, the GABA re-uptake inhibitors is tiagabine or nipecotic acid.

In one embodiment, the disorder characterized by excessive GABA re-uptake or GABA re-uptake is an anxiety disorder, a social anxiety disorder, a panic disorders, neuropathic pain (which includes fibromyalgia), chronic pain, muscle tremors, muscle spasms, seizures, convulsions and epilepsy.

In certain embodiments, the therapeutically effective amount of the agent in the POZ conjugate ranges from: i) about 0.05 mg/kg to about 10 mg/kg; ii) about 0.05 mg/kg to about 8 mg/kg; iii) about 0.05 mg/kg to about 6 mg/kg; iv) about 0.05 mg/kg to about 4 mg/kg; v) about 0.05 mg/kg to about 2 mg/kg; or vi) about 0.5 mg/kg to about 8 mg/kg.

In certain embodiments, the therapeutically effective amount of the agent in the POZ conjugate ranges from: i) about 1 mg/kg to about 30 mg/kg; ii) about 1 mg/kg to about 25 mg/kg; iii) about 1 mg/kg to about 20 mg/kg; iv) about 1 mg/kg to about 15 mg/kg; v) about 1 mg/kg to about 10 mg/kg; or vi) about 1 mg/kg to about 5 mg/kg.

In certain embodiments, the therapeutically effective amount of the agent in the POZ conjugate ranges from: i) about 10 mg/kg to about 30 mg/kg; ii) about 10 mg/kg to about 25 mg/kg; iii) about 10 mg/kg to about 20 mg/kg; iv) about 10 mg/kg to about 18 mg/kg; v) about 10 mg/kg to about 16 mg/kg; or vi) about 10 mg/kg to about 14 mg/kg.

In another embodiment, the present disclosure provides a method of treating a dopamine responsive condition in a subject, the method comprising administering to the subject a dose of a composition comprising a therapeutically effective amount of a polyoxazoline (POZ) conjugate, or a pharmaceutically acceptable form thereof, the POZ conjugate comprising a water-soluble POZ polymer, an agent linked to the POZ polymer by a physiologically degradable linkage, and an optional pendent moiety containing a hydrophilic or a hydrophobic portion linked to the POZ polymer.

In one embodiment, the dopamine responsive condition is disease or condition related to dopamine insufficiency in the peripheral or central nervous system. In one embodiment, the dopamine responsive condition is Parkinson's disease, restless leg syndrome, schizophrenia, attention-deficit hyperactivity disorder, hypodopaminergic conditions, SSRI-induced sexual dysfunction, depression, obesity, and type II diabetes.

In one embodiment, the dose is administered according to a dosing interval for a treatment period. In certain embodiments, the treatment period is 7 days to 60 months or the treatment period is continuous. In certain embodiments, the dosing interval is every day, every other day, two times per week, one time per week, one time every two weeks or 1 time every 4 weeks.

In one embodiment, the agent is an anticholinergic (such as, but not limited to, trihexyphenidyl, biperidin and hyoscyamine), a monamine oxidase-B inhibitor (such as, but not limited to, seligiline and rasagiline), a catechol-O-methyl transferase (COMT) inhibitor (such as, but not limited to, tolcapone and entacapone) or an adenosine $A_{2A}$ receptor antagonist (such as, but not limited to, preladenant, theophylline and istradefylline). In one embodiment, the agent is a dopamine agonist. Non-limiting examples of dopamine agonists include, but are not limited to, apomorphine, arbutamine, carbidopa, dobutamine, dopamine, entacapone, epinephrine, fenoldopam, isoetharine, isoproterenol, levopoda, levonordefrin, masaprocol, methyldopa, methyldopate, norepinephrine, protokylol, tolcapone, or (r)-(+)-fenoldopam, rotigotine, pramipexole, quinagolide, 5-OH-DPAT, ropinirole, pergolide, cabergoline, or bromocriptine.

In certain embodiments, the therapeutically effective amount of the agent in the POZ conjugate ranges from: i) about 0.05 mg/kg to about 10 mg/kg; ii) about 0.05 mg/kg to about 8 mg/kg; iii) about 0.05 mg/kg to about 6 mg/kg; iv) about 0.05 mg/kg to about 4 mg/kg; v) about 0.05 mg/kg to about 2 mg/kg; or vi) about 0.5 mg/kg to about 8 mg/kg.

In certain embodiments, the therapeutically effective amount of the agent in the POZ conjugate ranges from: i) about 1 mg/kg to about 30 mg/kg; ii) about 1 mg/kg to about 25 mg/kg; iii) about 1 mg/kg to about 20 mg/kg; iv) about 1 mg/kg to about 15 mg/kg; v) about 1 mg/kg to about 10 mg/kg; or vi) about 1 mg/kg to about 5 mg/kg.

In certain embodiments, the therapeutically effective amount of the agent in the POZ conjugate ranges from: i) about 10 mg/kg to about 30 mg/kg; ii) about 10 mg/kg to about 25 mg/kg; iii) about 10 mg/kg to about 20 mg/kg; iv) about 10 mg/kg to about 18 mg/kg; v) about 10 mg/kg to about 16 mg/kg; or vi) about 10 mg/kg to about 14 mg/kg.

In any of the methods of treatment described herein, the POZ conjugate comprises the optional pendent moiety comprising the hydrophilic of hydrophobic portion.

In any of the methods of treatment described herein, any of the methods for controlling the conformation of a POZ conjugate, controlling the cleavage of the agent from the POZ conjugate, controlling the release of the agent from the POZ, and/or selecting of a release profile of the agent from the POZ conjugate may be used.

In any of the methods of treatment described herein, any of the POZ conjugates described herein may be used.

In any of the methods of treatment described herein, a dose of the POZ conjugate contains a therapeutically effective amount. In any of the methods of treatment described herein, a dose of the POZ conjugate is administered at a therapeutically effective amount per day. Suitable therapeutically effective amounts are described in more detail herein.

In any of the methods of treatment described herein, a single dose of the POZ conjugate is administered during a course of treatment, where the dose preferably contains a therapeutically effective amount of the POZ conjugate. Such dose may be administered in a single administration (q.d.) or such dose may be administered in multiple administration on the same day (such as but not limited to b.i.d. or t.i.d.). When a dose is divided into multiple administrations on a given day, the dose may be divided equally or the dose may be divided unequally at each administration. Any given dose may be delivered in a single dosage form or more than one dosage form (for example, a tablet).

In any of the methods of treatment described herein, multiple doses of the POZ conjugate are administered during a course of treatment, where at least one dose or all doses preferably contains a therapeutically effective amount of the POZ conjugate. Each dose may be administered in a single administration (q.d.) or such dose may be administered in multiple administration on the same day (such as but not limited to b.i.d. or t.i.d.). When a dose is divided into multiple administrations per day, the dose may be divided equally or the dose may be divided unequally at each administration. Any given dose may be delivered in a single dosage form or more than one dosage form (for example, a tablet). The therapeutically effective amount administered in each dose need not be the same. For example, in some embodiments a course of treatment comprises administering at least one loading dose and at least one maintenance dose, wherein the loading dose contains a greater amount of the POZ conjugate as compared to the maintenance dose (such as, but not limited to, 2 to 10 times higher).

In any of the methods of treatment described herein, multiple doses of the POZ conjugate are administered during a course of treatment, and the course of treatment is delivering a dose every day, every other day, twice per week, 1 time per week, every 10 days, every 2 weeks, every three weeks, or every 4 weeks.

In any of the methods of treatment described herein, the POZ conjugate may be administered in a pharmaceutically acceptable form. In any of the methods of treatment described herein, the POZ conjugate may be administered as a part of a pharmaceutical composition.

In any of the methods of treatment described herein, the POZ conjugate is administered by parenteral administration. In any of the methods of treatment described herein, the POZ conjugate is administered by subcutaneous administration. In any of the methods of treatment described herein, the POZ conjugate is administered by intramuscular administration. In any of the methods of treatment described herein, the POZ conjugate is administered by intravenous administration.

Methods of Maintaining a Plasma Concentration of an Agent

In one embodiment, the present disclosure provides a method of achieving a plasma concentration of an agent above a minimum therapeutic level in a subject for all or substantially all of a dosing interval or a treatment period, the method comprising administering to the subject over the dosing interval a dose of a POZ conjugate, or a pharmaceutically acceptable form thereof, comprising a water-soluble polyoxazoline (POZ) polymer, the agent linked to the POZ polymer by a physiologically degradable linkage, and an optional pendent moiety linked to the POZ polymer containing a hydrophilic or a hydrophobic portion.

In one embodiment, the agent is a phytocannabinoid. In one embodiment, the agent is a phytocannabinoid selected from the group consisting of: cannabidiol, cannabigerol, cannabigerolic acid, cannabidiolic acid, cannabidiolmonomethylether, cannabidiol-C4, cannabidarinic acid, cannabidivarin, cannabidiol or cannabigerol propyl variant, cannabichromene, cannabichromenic acid, cannabichromevarinic acid, cannabichromevarin, cannabinol, cannabicyclol, tetrahydrocannabivarin, $\Delta^9$-THC, ajulemic acid, and dexanabinol.

In one embodiment, the agent is an anticholinergic (such as, but not limited to, trihexyphenidyl, biperidin and hyoscyamine), a monamine oxidase-B inhibitor (such as, but not limited to, seligiline and rasagiline), a catechol-O-methyl transferase (COMT) inhibitor (such as, but not limited to, tolcapone and entacapone) or an adenosine $A_{2A}$ receptor antagonist (such as, but not limited to, preladenant, theophylline and istradefylline). In one embodiment, the agent is a dopamine agonist. Non-limiting examples of dopamine agonists include, but are not limited to, apomorphine, arbutamine, carbidopa, dobutamine, dopamine, entacapone, epinephrine, fenoldopam, isoetharine, isoproterenol, levopoda, levonordefrin, masaprocol, methyldopa, methyldopate, norepinephrine, protokylol, tolcapone, or (r)-(+)-fenoldopam, rotigotine, pramipexole, quinagolide, 5-OH-DPAT, ropinirole, pergolide, cabergoline, or bromocriptine.

In one embodiment, the agent is a GABA re-uptake inhibitor. Non-limiting examples of GABA re-uptake inhibitors include, but are not limited to, tiagabine or nipecotic acid.

In certain embodiments, the POZ conjugate contains 1.6%±1.0% to 9.6%±1.0% phytocannabinoid (w/w agent to POZ polymer).

In certain embodiments of any of the methods, the dose of the composition comprising the POZ conjugate is administered as a single dose. In certain embodiments, the dose of the composition comprising the POZ conjugate is administered in multiple doses.

In certain embodiments, a plasma concentration of the agent in the subject is greater than a minimum therapeutic level during all or substantially all of the dosing interval or the treatment period. In one aspect of this embodiment, the minimum therapeutic level is 5 ng/ml, 50 ng/ml, 150 ng/ml, 500 ng/ml, 1000 ng/ml, or 1,500 ng/ml.

In certain embodiments, a plasma concentration of the agent in the subject is greater than a minimum therapeutic level during all or substantially all of the dosing interval or the treatment period and a single dose of the POZ conjugate is administered. In certain embodiments, a plasma concentration of the agent in the subject is greater than a minimum therapeutic level during all or substantially all of the dosing interval or the treatment period, multiple doses of the POZ conjugate are administered, and the dose dosing interval is 2 times per week or one time per week. In one aspect of these embodiment, the minimum therapeutic level is 5 ng/ml, 50 ng/ml, 150 ng/ml, 500 ng/ml, 1000 ng/ml, or 1,500 ng/ml.

In certain embodiments, the treatment period is 7 days to 60 months or the treatment period is continuous. In certain embodiments, the dosing interval is every day, every other day, two times per week, one time per week, one time every two weeks or 1 time every 4 weeks.

In certain embodiments, the agent is a phytocannabinoid. In certain embodiments, the POZ conjugate contains 1.6%±1.0% to 9.6%±1.0% phytocannabinoid (w/w phytocannabinoid to POZ polymer). In certain embodiments, the POZ conjugate contains 1.6%±1.0% to 9.6%±1.0% CBD (w/w CBD to POZ polymer).

In certain embodiments of any of the methods of treatment described herein, the dose of the composition comprising the POZ conjugate is administered in a single dose. In certain embodiments, the dose of the composition comprising the phytocannabinoid-polymer conjugate is administered in multiple doses.

In certain embodiments, the dose of the POZ conjugate contains between 0.25 mg eq/kg to 2.5 mg eq/kg of the phytocannabinoid. In certain embodiments, the phytocannabinoid is CBD. Such a dose may be delivered as a single dose or in multiple doses.

In certain embodiments, the dose of the POZ conjugate contains between 0.25 mg eq/kg to 2.5 mg eq/kg of the phytocannabinoid, multiple doses of the POZ conjugate are administered, and the dosing interval is 2 times per week or one time per week. In certain embodiments, the phytocannabinoid is CBD.

In certain embodiments, the dose of a POZ conjugate contains between 2.5 mg eq/kg to 5.0 mg eq/kg of the phytocannabinoid. In certain embodiments, the phytocannabinoid is CBD. Such a dose may be delivered as a single dose or in multiple doses.

In certain embodiments, the dose of the POZ conjugate contains between 2.5 mg eq/kg to 5.0 mg eq/kg of the phytocannabinoid, multiple doses of the POZ conjugate are administered, and the dose dosing interval is 2 times per week or one time per week. In certain embodiments, the phytocannabinoid is CBD.

In certain embodiments, a plasma concentration of the phytocannabinoid in the subject is greater than a minimum therapeutic level during all or substantially all of the dosing interval or the treatment period. In one aspect of this embodiment, the minimum therapeutic level is 5 ng/ml, 50 ng/ml, 150 ng/ml, 500 ng/ml, or 1000 ng/ml.

In certain embodiments, a plasma concentration of the phytocannabinoid in the subject is greater than a minimum therapeutic level during all or substantially all of the dosing interval or the treatment period, the dose of the POZ conjugate contains between 2.5 mg eq/kg to 5.0 mg eq/kg of the phytocannabinoid and the dose dosing interval is 2 times per week or one time per week. In one aspect of this embodiment, the minimum therapeutic level is 5 ng/ml, 50 ng/ml, 150 ng/ml, 500 ng/ml, 1000 ng/ml, or 1,500 ng/ml. In another aspect of this embodiment, the phytocannabinoid is CBD.

In certain embodiments, a plasma concentration of the phytocannabinoid in the subject is greater than a minimum therapeutic level during all or substantially all of the dosing interval or the treatment period, the dose of the POZ conjugate contains between 0.25 mg eq/kg to 2.5 mg eq/kg of the phytocannabinoid and the dose dosing interval is 2 times per week or one time per week. In one aspect of this embodiment, the minimum therapeutic level is 5 ng/ml, 50 ng/ml, 150 ng/ml, 500 ng/ml, or 1000 ng/ml. In another aspect of this embodiment, the phytocannabinoid is CBD.

In certain embodiments, the treatment period is 7 days to 60 months or the treatment period is continuous. In certain embodiments, the dosing interval is every day, every other day, two times per week, one time per week, one time every two weeks or 1 time every 4 weeks.

In any of the above methods, the POZ conjugate comprises the optional pendent moiety comprising the hydrophilic of hydrophobic portion.

In any of the above methods, any of the methods for controlling the conformation of a POZ conjugate, controlling the cleavage of the agent from the POZ conjugate, controlling the release of the agent from the POZ, and/or selecting of a release profile of the agent from the POZ conjugate may be used.

In any of the above methods, any of the POZ conjugates described herein may be used.

In any of the above methods, a dose of the POZ conjugate contains a therapeutically effective amount. In any of the above methods, a dose of the POZ conjugate is administered at a therapeutically effective amount per day. Suitable therapeutically effective amounts are described in more detail herein.

In any of the above methods, a single dose of the POZ conjugate is administered during a course of treatment, where the dose preferably contains a therapeutically effective amount of the POZ conjugate. Such dose may be administered in a single administration (q.d.) or such dose may be administered in multiple administration on the same day (such as but not limited to b.i.d. or t.i.d.). When a dose is divided into multiple administrations on a given day, the dose may be divided equally or the dose may be divided unequally at each administration. Any given dose may be delivered in a single dosage form or more than one dosage form (for example, a tablet).

In any of the above methods, multiple doses of the POZ conjugate are administered during a course of treatment, where at least one dose or all doses preferably contains a therapeutically effective amount of the POZ conjugate. Each dose may be administered in a single administration (q.d.) or such dose may be administered in multiple administration on the same day (such as but not limited to b.i.d. or t.i.d.). When a dose is divided into multiple administrations per day, the dose may be divided equally or the dose may be divided unequally at each administration. Any given dose may be delivered in a single dosage form or more than one dosage form (for example, a tablet). The therapeutically effective amount administered in each dose need not be the same. For example, in some embodiments a course of treatment comprises administering at least one loading dose and at least one maintenance dose, wherein the loading dose contains a greater amount of the POZ conjugate as compared to the maintenance dose (such as, but not limited to, 2 to 10 times higher).

In any of the above methods, multiple doses of the POZ conjugate are administered during a course of treatment, and the course of treatment is delivering a dose every day, every other day, twice per week, 1 time per week, every 10 days, every 2 weeks, every three weeks, or every 4 weeks.

In any of the above methods, the POZ conjugate may be administered in a pharmaceutically acceptable form. In any of the above methods, the POZ conjugate may be administered as a part of a pharmaceutical composition.

In any of the above methods, the POZ conjugate is administered by parenteral administration. In any of the above methods, the POZ conjugate is administered by subcutaneous administration. In any of the above methods, the POZ conjugate is administered by intramuscular administration. In any of the above methods, the POZ conjugate is administered by intravenous administration.

Pharmaceutical Compositions and Routes of Administration

Pharmaceutical compositions are provided that comprise an amount of a conjugate of the present disclosure. In one embodiment, such pharmaceutical compositions contain a therapeutically effective amount of a conjugate of the present disclosure. In a particular embodiment, the conjugate of the present disclosure is a conjugate of the formula I. In addition, other active agents may be included in such pharmaceutical compositions. Additional active agents to be included may be selected based on the disease or condition to be treated.

The pharmaceutical compositions disclosed may comprise one or more conjugates of the present disclosure, alone or in combination with additional active agents, in combination with a pharmaceutically acceptable carrier. Examples of such carriers and methods of formulation may be found in *Remington's Science and Practice of Pharmacy* (23$^{rd}$ edition, ISBN 9780128200070) and *Handbook of Pharmaceutical Excipients* (8th edition, 978-0-85-7112712). Such conjugates and pharmaceutical compositions may be used in the manufacture of a medicament for use in the methods of treatment described herein. The conjugates of the disclosure are useful in both free form and in the form of pharmaceutically acceptable salts.

The pharmaceutically acceptable carriers described herein, including, but not limited to, vehicles, adjuvants, excipients, or diluents, are well-known to those who are skilled in the art. Pharmaceutically acceptable excipients are also well-known to those who are skilled in the art. The choice of excipient will be determined in part by the particular conjugate(s), as well as by the particular method used to administer the formulation. Accordingly, there is a wide variety of suitable formulations of the pharmaceutical composition. The following methods and excipients are merely exemplary and are in no way limiting. Suitable carriers and excipients include solvents such as water, alcohol, polyethylene glycol, glycofural and propylene glycol, solid absorbents and diluents, surface active agents, suspending agent, tableting binders, lubricants, flavors, and coloring agents. The pharmaceutically acceptable carriers can include polymers and polymer matrices. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. Typically, the pharmaceutically acceptable carrier is chemically inert to the active agents in the composition and has no detrimental side effects or toxicity under the conditions of use. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

In one embodiment, such pharmaceutical compositions contain a therapeutically effective amount of a POZ conjugate of the present disclosure. In a particular embodiment, the POZ conjugate is a conjugate of formula I. In addition, other active agents may be included in such pharmaceutical compositions. Additional active agents to be included may be selected based on the disease or condition to be treated.

The pharmaceutical compositions disclosed may comprise one or more POZ conjugates of the present disclosure, alone or in combination with additional active agents, in combination with a pharmaceutically acceptable carrier.

The POZ conjugates of the present disclosure and pharmaceutical compositions containing such POZ conjugates can be administered by any conventional method available for use in conjunction with pharmaceuticals, either as individual therapeutic agents or in combination with additional therapeutic agents. One skilled in the art will appreciate that suitable methods of administering a conjugates of the present disclosure, either alone or in a pharmaceutical formulation, to an patient are available, and, although more than one route can be used and a particular route can provide a more immediate and more effective reaction than another route.

In one embodiment, the conjugates of the present disclosure are administered in therapeutically effective amount, whether alone or as a part of a pharmaceutical composition. The therapeutically effective amount and the dosage administered will, of course, vary depending upon known factors, such as the pharmacodynamic characteristics of the particular agent and its mode and route of administration, the age, health and weight of the recipient; the severity and stage of the disease state or condition; the kind of concurrent treatment; the frequency of treatment; and the effect desired.

The total amount of the POZ conjugate administered, whether alone or as a part of a pharmaceutical composition, will also be determined by the route, timing and frequency of administration as well as the existence, nature, and extent of any adverse side effects that might accompany the administration of the conjugate and the desired physiological effect. It will be appreciated by one skilled in the art that various conditions or disease states, in particular chronic conditions or disease states, may require prolonged treatment involving multiple administrations.

In one embodiment of the pharmaceutical compositions, the POZ conjugate(s) of the present disclosure will ordinarily be present in an amount of about 0.5-95% weight based on the total weight of the composition. Multiple dosage forms may be administered as part of a single treatment.

The POZ conjugates of the present disclosure, either alone or as a part of a pharmaceutical composition, can be administered enterally in solid dosage forms, such as capsules, tablets, and powders, or in liquid dosage forms, such as milk, elixirs, syrups and suspensions. The conjugates of the present disclosure, either alone or as a part of a pharmaceutical composition, can also be administered parenterally, in sterile liquid dosage forms. The conjugates of the present disclosure, either alone or as a part of a pharmaceutical composition, can also be administered intranasally (nose drops) or by inhalation via the pulmonary system, such as by propellant based metered dose inhalers or dry powders inhalation devices. Other dosage forms include topical administration, such as administration transdermally, via patch mechanism or ointment.

Formulations suitable for enteral or oral administration may be liquid solutions, such as a therapeutically effective amount of a conjugate dissolved in diluents, such as milk, water, saline, buffered solutions, infant formula, other suitable carriers, or combinations thereof. The conjugate can then be mixed to the diluent just prior to administration. In an alternate embodiment, formulations suitable for enteral or oral administration may be capsules, sachets, tablets, lozenges, and troches. In each embodiment, the formulation may contain a predetermined amount of the conjugate of the present disclosure, as solids or granules, powders, suspensions and suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers.

Lozenge forms can comprise a conjugate in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For parenteral administration the POZ conjugate may be combined with a sterile aqueous solution that is isotonic with the blood of the subject. Such a formulation may be prepared by dissolving a POZ conjugate in water containing physiologically-compatible substances, such as sodium chloride, glycine and the like, and having a buffered pH compatible with physiological conditions, so as to produce an aqueous solution, then rendering said solution sterile. The formulation may be presented in unit dose form, such as sealed ampules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's body. A preferred mode of injection is subcutaneous.

Parenteral administration includes aqueous and non-aqueous based solutions. Examples of which include, for example, water, saline, aqueous sugar or sugar alcohol solutions, alcoholic (such as ethyl alcohol, isopropanol, glycols), ethers, oils, glycerides, fatty acids, and fatty acid esters. In some embodiments, water is used for parenteral administration. In some embodiments, saline is used for parenteral administration. Oils for parenteral injection include animal, vegetable, synthetic, petroleum based oils, mineral oil, petrolatum, soybean, corn, cottonseed, peanut, and the like. Examples of sugars for solution include sucrose, lactose, dextrose, mannose, and the like. Examples of fatty acids and esters include oleic acid, myristic acid, stearic acid, isostearic acid, and esters thereof. Parenteral formulations can also be sterile lyophilized powders that need to be reconstituted in WFI, normal saline or 5% dextrose solution. Lyophilized powder contains the drug along with excipients such as mono, di and trisaccharide sugars. Examples include dextrose, sucrose, raffinose, trehalose, mannitol, sorbitol, etc. Such formulations for parenteral administration may also include a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The parenteral formulations typically contain from about 0.5% to about 50% by weight of the conjugate in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Methods

Materials

The ethyl oxazoline monomer was purchased from Polymer Chemistry Innovation, Tucson, Arizona. The functional pentynyl monomer was prepared at Serina Therapeutics. The solvents used in the synthesis and extraction of the polymer and polymer conjugates were ACS anhydrous grade or better and were acquired from EMD Chemicals. The initiators, reagents and catalysts used in the synthesis of the polymer and polymer conjugates were acquired from Sigma-Aldrich in St. Louis, MO. Samples of the active molecules used in the POZ conjugation were rotigotine (from Sai Chemicals, Hyderabad, India), cannabidiol, $\Delta^9$-THC, cannabigerol and buprenorphine (from PuriSys/Noramco, Wilmington, DE), and dexanabinol (from Cayman Chemical, Ann Arbor, MI). Polyethylene glycol (PEG) reagents with 4-arm and 8-arm chains were obtained from Creative PEGWorks, Chapel Hill, NC and the dextran 6-arm polymer was synthesized at Serina Therapeutics.

In-Vitro Release of Drugs from Polymer Conjugates

Approximately 50 mg of a sample of a POZ/PEG/dextran drug conjugate was accurately weighed and added to a 5 mL volumetric flask and a solution of 5% w/w of dextrose was added to dissolve and dilute the sample. Under a laminar flow hood, 300 µL of this solution was added to 3 mL of chilled plasma (rat, monkey or human) and mixed gently by inverting several times. Using an Eppendorf pipettor, 200 µL of the plasma solution was aliquoted into separate microcentrifuge tubes with screw caps and incubated in a shaking water bath at 37° C., to allow for the in-vitro hydrolysis of drug from the POZ conjugate. The experiments were performed in triplicate.

At each time point, a set of tubes was removed, and the samples were quenched by addition of 1000 µL of 0.1% trifluoroacetic acid (TFA) in acetonitrile (ACN). The suspension was vortexed to extract the POZ drug conjugate and the released drug from the crashed plasma proteins. The solution was centrifuged for 5 min at 14000 rpm and the supernatant (500 µL) was added to 500 µL 0.1% TFA in H2O and placed into an HPLC vial.

The samples were analyzed by HPLC, using a Zorbax 300SB C-8 column, 5 mm×4.6×150 mm, and a UV detector, and gradient elution was performed with 0.1% TFA in H$_2$O (Mobile Phase A) and 0.1% TFA in acetonitrile (Mobile Phase B). A calibration curve was created for each drug tested using a peak area versus concentration curve to determine the concentration of hydrolyzed drug at each time point.

Chemical Synthesis of POZ-Cyanine-5 (POZ-Cy5) Conjugates

POZ polymer conjugates of different molecular weights containing cyanine-5 as the agent were synthesized as described below. Poly(2-ethyl-2-oxazoline) (PEOZ) polymers with an average of ten alkyne pendants per POZ polymer were synthesized as described in Example 1. The cyanine5-azide-fluorophore (Cy5, Lumiprobe Corp, Hunt Valley, MD) was attached to the alkyne pendants on the POZ polymer using the quantitative "click chemistry" reaction (generally as described in Example 2). The average number of Cy5 fluorophores attached to each POZ polymer ranged from 1.4-1.8 and was verified by $^1$H-NMR. The purity of each compound was determined by RP-HPLC.

Pharmacokinetics of POZ Polymers of Different Molecular Weights

The pharmacokinetics of different molecular weight POZ polymer conjugates (10, 20, 30, 40 and 60 kDa) were investigated using POZ-Cy5 conjugates (synthesized as described herein) in male Sprague-Dawley rats. An in-house institutional animal care and use committee (IACUC) reviewed and approved the study protocol before start of the study. After arrival at the vivarium, the rats were placed in a rat cages and allowed at least 3 days of acclimatization before initiation of dosing. Thirty animals were divided into 10 groups, with 3 animals per group. Five groups of rats were placed into a restraining device and the POZ-Cy5 conjugate was injected intravenously into the tail vein of each animal using a 25 G BD precision glide needle. The remaining 5 groups of rats were administered the POZ-Cy5 conjugate via subcutaneous injection (with the use of a restraining device) into the left flank using a 23 G BD precision glide needle. The dose was 10 mg/kg, dose volume was 1 mL/kg (~0.25 mL) and the duration of each injection was approximately 10-15 seconds. Serial venous blood samples (100 μL) were collected from the tail vein of each animal at the following time points: 0.25, 1, 3, 8, 12, 24, 48, 72, 96, 120, 144, 168, 240, 336, 408, 504, 576, and 672 hours post-dose. Blood was transferred into 1.5 mL Eppendorf tubes containing a fixed volume (150 μL) of 1×PBS with 1.2% of a 0.2N EDTA solution. Samples were briefly mixed by repeated up and down pipetting. Samples were immediately placed in ice and covered to minimize exposure to light. The samples were then centrifuged at 10,000 rpm for 3 minutes at 4° C. Supernatant from each tube (100 μL) was removed and placed in a cryo-tube. The samples were immediately frozen on dry ice and then transferred to a minus 80° C. freezer.

Fluorescence spectrophotometry was used to measure the amount of POZ-Cy5 conjugate in each sample. The excitation and emission wavelength of Cy5 fluorophore is 650 nm and 670 nm, respectively. An aliquot of thawed sample was placed in a 96 well plate and the absorption data was recorded between 660-750 nm at 1 nm intervals.

A stock solution was prepared with each molecular weight of POZ-Cy5 conjugate by dissolving a known weight of the conjugate in PBS EDTA stock solution. Dilutions of the stock solution were made in PBS EDTA to make final concentrations of 20, 10, 5, 1, 0.5, 0.1 and 0.05 μg/mL. 150 μL, of each standard solution was placed in a 1.5 mL centrifuge tube and 50 μL, of freshly collected whole blood was placed in each tube. The solutions were gently mixed and centrifuged at 3000 rpm for 3 minutes. 75 μL, of supernatant of each standard was pipetted out and placed in the top row of the 96-well plate. Standards were prepared fresh daily before each measurement. One plate was prepared for each molecular weight POZ-Cy5 conjugate. The plates were placed in the spectrophotometer holder, one at a time, and the emission absorbance values were recorded (Au) at 670 nm at signal gain values set at 80, 100, 120 and 150. A standard curve equation (peak area versus concentration curve with linear regression) was calculated for each POZ molecular weight standard. These measurements were done in duplicate for each time point. The concentration of POZ Cy5 in plasma at each time point was calculated from this equation.

Pharmacokinetics of Drugs Released from POZ Conjugates

The plasma levels of drugs released into the blood stream were measured in rodent (Sprague Dawley rats) and non-human primates (*Macaca fascicularis*, cynomolgus monkeys) following single subcutaneous injections of their respective POZ conjugates with different linkers and drug loading wt %. An in-house institutional animal care and use committee (IACUC) reviewed and approved each study protocol before start of the studies[.]

Male Sprague Dawley naive rats (age 8-9 weeks, weight 200-250 g) were acquired and placed in rat cages and allowed at least 3 days of acclimatization before the start of the dosing. Each test group contained 3 rats. The POZ conjugates were dissolved 5% dextrose injection and the pH of the solution was adjusted to about 4.0 with 0.1 N hydrochloric acid. Each animal received a single subcutaneous (SC) injection of test article solution equivalent to a dose of 1.5-1.6 mg/kg (based in drug equivalents) and at a volume of 1 mL/kg, and into the left flank using a 23 G BD precision glide needle. The duration of each injection was approximately 10-15 seconds. Serial venous blood samples of 400-500 μL were collected from the tail vein of each animal at the following time points: 3, 6, 12, 24, 48, 72, 96, and 168 hours post-dose. All blood samples were collected in pre-labeled BD Microtainer tubes containing NaF/disodium EDTA, gently mixed and placed in an ice batch. Plasma was harvested by centrifugation at 3000 rpm for 15 minutes at 4° C. Plasma aliquots of 100 μL were collected in separate tubes containing 10 μL of a solution of 3N HCl acid, gently mixed and immediately frozen and stored at −70° C.

Female cynomolgus non-naive monkeys (>2 years of age, weight 2.5-3.5 kg) were acquired and placed in cages for the studies. The animals (n=3 per group) had a washout period of at least 30 days since the end of the previous study. The POZ conjugates were dissolved 5% dextrose injection and the pH of the solution was adjusted to about 4.0 with 0.1 N hydrochloric acid. Each animal received a single subcutaneous (SC) injection of test article solution equivalent to a dose of 1.5 mg/kg (based in drug equivalents) and at a volume of 0.3 mL/kg, and into the right shoulder using a 23 G BD precision glide needle. The duration of each injection was approximately 10-15 seconds. Blood samples of about 1000 μL were collected from a peripheral vein of each animal at the following time points: 3, 6, 12, 24, 48, 72, 96, 120, 144, 168, 240 and 336 hours post-dose. All blood samples were collected in pre-labeled BD Microtainer tubes containing NaF/disodium EDTA, gently mixed and placed in an ice batch. Plasma was harvested by centrifugation at 3000 rpm for 15 minutes at 4° C. Plasma aliquots of 250 μL were collected in separate tubes containing 10 μL of a solution of 3N HCl acid, gently mixed and immediately frozen and stored at −70° C.

The plasma samples were processed by the 'protein crash' method using cold acetonitrile. The samples were mixed, centrifuged at 13,000 rpm for 15 min and the organic phase sampled and assayed for either rotigotine, buprenorphine or cannabidiol using a qualified LC-MS/MS method. Internal standards of rotigotine-d3, buprenorphine-d4 and cannabidiol-d3 were used in the assays.

Chemical Synthesis of POZ and POZ Conjugates

Methods for the synthesis of POZ polymers and POZ polymer conjugates have been described in the art. POZ polymers are generally prepared by reaction of the appropriate stoichiometric amount of one or more 2-alkyl-2-oxazoline monomers with an electrophilic initiator (such as, but not limited to, methyl triflate; MeOTF) or a strong acid (such as, but not limited to, triflic acid; HOTf), followed by termination with a nucleophile (such as, but not limited to, mercaptans/mercaptides, hydroxides, a thiols, or amine). Exemplary mercaptans include but are not limited to, mercapto-esters (such as, but not limited to, S—$CH_2CH_2$—$CO_2CH_2CH_3$) and mercapto-protected amines (such as, but not limited to, —S—$CH_2CH_2$—NH-tBoc). In a particular embodiment, when mercapto-esters are used as the terminating agent, effective, large-scale purification by ion-exchange chromatography (to remove impurities such as secondary amines) may be used after hydrolysis of the ester to yield the carboxylic acid or other group suitable for use in ion-exchange chromatography. The subsequent POZ polymers exhibit low polydispersity values and low levels of impurities. The nature of the 2-alkyl-2-oxazoline monomers used to produce the POZ polymer may be the same, resulting in a homopolymer (such as, but not limited to, poly(methyl oxazoline) or poly(ethyl oxazoline) two or more 2-alkyl-2-oxazoline monomers may be used to produce the POZ polymer resulting in copolymers, such as, but not limited to, random copolymers or block copolymers.

Methods for the synthesis of POZ polymers with single functional groups on a terminal end of the polymer have been described in U.S. Pat. No. 7,943,141, and methods of synthesis of POZ polymers with pendent functional groups and POZ polymer conjugates with agents linked to the pendent functional groups have been described in U.S. Pat. No. 8,393,093 (which patent is specifically incorporated herein for such teachings).

An exemplary synthesis of POZ random co-polymer is provided below. Desired 2-alkyl-2-oxazoline monomers (for example, 2-(4-pentynyl)-2-oxazoline; PtynOZ; ethyl oxazoline; EOZ; and T-methyl propionate oxazoline; TMPOZ) are prepared in a suitable solvent at room temperature (for example, chlorobenzene). The percentage of each monomer is controlled by reaction of the appropriate stoichiometric amount of the 2-alkyl-2-oxazoline monomers. To this solution is added an initiator as described below (such as MeOTF). The solution is stirred at room temperature for a period of time (for example, 5 minutes to 120 minutes) and then heated (for example, at 70° C. to 130° C. for 10 min. to 12 hours). The mixture is cooled to 0° C. and then terminated using a desired nucleophile (for example a mercapto-ester). The mixture is stirred to allow for termination of the polymerization reaction. The POZ polymer is then recovered.

An exemplary synthesis of POZ block polymer is provided below. An initiating agent (for example, MeOTf) is added to a solution of a first 2-alkyl-2-oxazoline monomer (for example, PtynOZ) in a suitable solvent at room temperature (for example, chlorobenzene). The solution is stirred at room temperature for a period of time (for example, 5 minutes to 120 minutes) and then heated (for example, at 70° C. to 130° C. for 10 min. to 12 hours). A second 2-alkyl-2-oxazoline monomer (for example, EOZ) is added to the reaction and the mixture is stirred and heated (for example, at 70° C. to 130° C. for 10 min. to 12 hours). The mixture is cooled to room temperature and terminated by the addition of piperidine (0.4 mL, 0.004 mol). The mixture is stirred to allow for termination of the polymerization reaction. The POZ polymer is then recovered.

An exemplary synthesis of a random POZ polymer with pendent functional groups and POZ conjugates are provided in Examples 1 and 2 herein.

EXAMPLES

Example 1—Exemplary Synthesis of Random H-[(Ptyn)$_{10}$(EOZ)$_{190}$]-T-$CO_2$H (POZ10p20k)

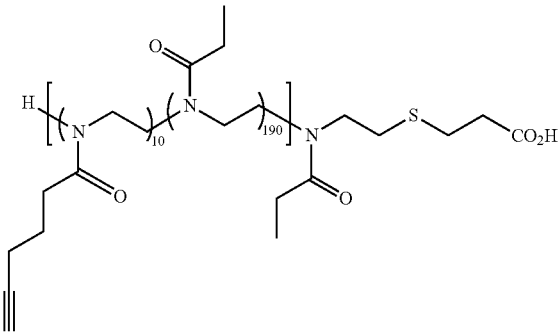

This example describes the synthesis of H-[(Ptyn)$_{10}$(EOZ)$_{190}$]-T-$CO_2$H. However, other POZ polymers of different molecular weights, different initiating and terminating groups as well as different groups at the pendent position may be produced by the same method. In addition, block copolymers may be produced in addition to the random copolymers described in this example.

For the synthesis of H-[(Ptyn)$_{10}$(EOZ)$_{190}$]-T-$CO_2$H, triflic acid (HOTf, 173.3 μL, 1.96 mmol) was added to a solution of 2-pentynyl-2-oxazoline (PtynOZ, 3.76 g, 27.4 mmol, 14 eq) and 2-ethyl-2-oxazoline (EOZ, 46.61 g, 470.2 mmol, 240 eq) in chlorobenzene (124 mL). After stirring for 5 minutes at room temperature, the mixture was heated to 80° C. for 10 hours followed by cooling to room temperature. In a separate flask, the terminating reagent was prepared by the dropwise addition of methyl 3-mercaptopropionate (1.23 mL, 0.0114 mol) into a suspension of sodium hydride (60% in mineral oil, 0.272 g, 0.0068 mol) in chlorobenzene (34 mL). This mixture was stirred for 7 hours, before the solution of living polymer of H-(Ptyn)$_{10}$(EOZ)$_{200}$⁺ was added. The resulting mixture was then stirred for 18 hours. The solvent was removed by rotary evaporation to yield a white residue. This residue was dissolved in water and the pH adjusted to 12.0. The resulting aqueous solution was purified by ion-exchange chromatography using DEAE Sepharose FF. The aqueous solution was saturated with NaCl (15% w/w) and extracted with dichloromethane. The combined organic phases were dried over anhydrous sodium sulfate, filtered, and concentrated using a rotary evaporator. The residue was precipitated by adding the dichloromethane concentrate to diethyl ether. The precipitated material was collected and dried in vacuo to give 22.8 g of desired product as a white powder (50% yield).

$^1$H NMR (Varian, 500 MHz, 10 mg/mL CDCl$_3$) showed the usual backbone peaks at 1.13 ppm (m, 3H, CH$_3$CH$_2$CO—); 2.32 ppm (m) and 2.41 (s) (total area 2H, CH$_3$CH$_2$CO—); and 3.47 ppm (m, 4H, —NCH$_2$CH$_2$N—). The terminal group peaks appear at 2.63 ppm (m, 2H, —SCH$_2$CH$_2$CO$_2$H), 2.74 ppm (m, 2H, —CH$_2$SCH$_2$CH$_2$CO$_2$H), and 2.85 ppm (m, 2H, —SCH$_2$CH$_2$CO$_2$H). The pendent pentynyl group peaks appear at 1.85 ppm (m, 2H, —CH$_2$CH$_2$C≡CH) and 2.03 ppm (br s, 1H, —CH$_2$CH$_2$C≡CH). The number of pendent, Ptyn, groups were determined as 8.5 by comparing the integrations of terminal acetylene proton and polymer backbone protons. GPC gave Mn=19,500 Da and Mp=20,800 Da with PDI of 1.07.

Example 2—General Preparation of POZ Conjugates

Synthesis of POZ with pendent functional groups and pendent, releasable drugs (typically with ester linkers to phenolic drugs) via the route shown in the reaction scheme below has been described in several of our publications and patents [4, 7].

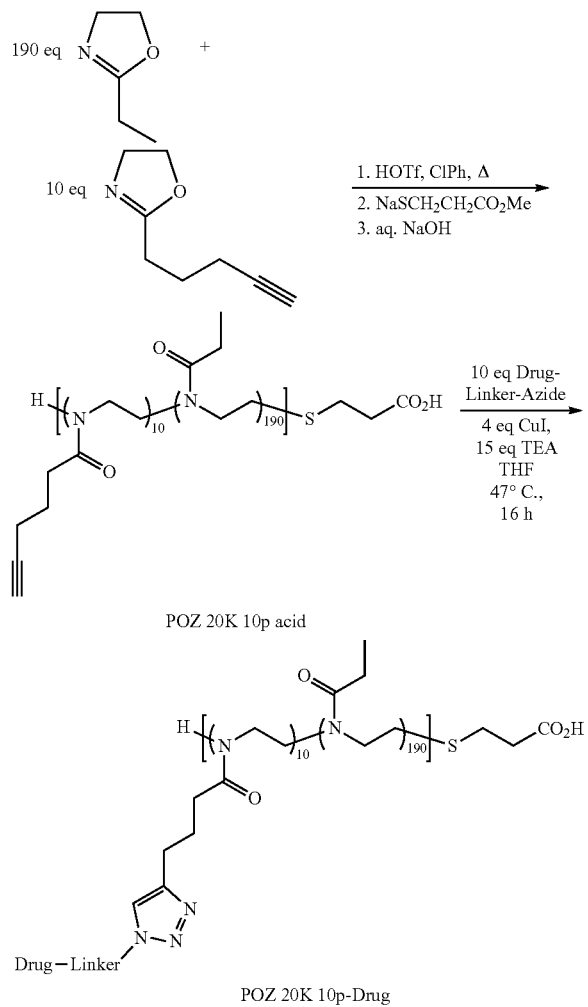

Figure 1:
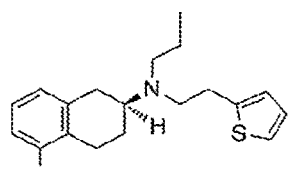
FIG. 1 shows structures of selected compounds of the Examples.
Figure 1:
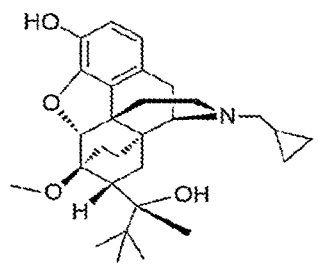
Figure 1:
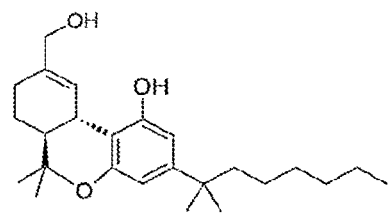
Figure 1:
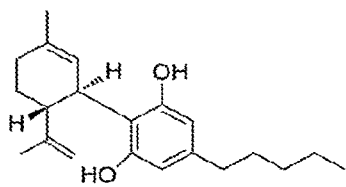
Figure 1:
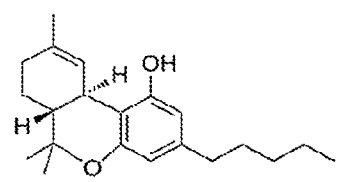
Figure 1:
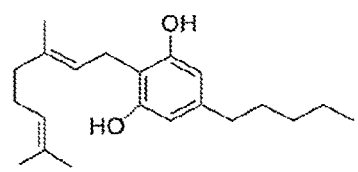

POZ conjugates of the phenolic drugs shown in FIG. 1 were prepared by this procedure. An azido alkyl carboxylic acid linker was first coupled to the phenolic —OH of the small molecule drug to make a mono-ester. Drugs such as cannabidiol and cannabigerol have two potential phenolic —OH groups, and the diesters formed were removed by preparative chromatography. The azido alkyl esters of these drugs were then "clicked" to the pentynyl pendants on the POZ polymer as above. Examples of alkyl carboxylic acid linkers include, but are not limited to, acetic, 2-propionic and 3-propionic acid. The number of drug molecules loaded can vary and will depend on the number of equivalents (eq) of the Drug-Linker-Azide used in the click reaction. When 10 eq are used the conjugate is found to be fully clicked on all 10 pendants of the POZ polymer chain. Conjugates with lower number of drug loading were also prepared using less than 10 eq of the Drug-Linker-Azide compound, i.e. 8 and 6 eq. The percentage (% w/w) of drug loaded was chromatographically assayed then calculated using the molecular weight of the small molecule drug.

PEG and dextran conjugates of rotigotine were also prepared using similar click chemistry conditions as used with the POZ polymer. Procedures to purify and assay these conjugates were the same.

Example 3—the Presence of Hydrophilic Propionic Acid Pendent Moities Increases Hydrolysis Rates As discussed above, the presence of a hydrophilic pendent moiety is hypothesized to increase the hydrolysis rate of agents from a POZ polymer conjugate, resulting in shorter half-lives of the POZ polymer conjugate in vivo. To determine if hydrophilic pendent moieties impacted hydrolysis rates of an agent from a POZ polymer conjugate in vitro, two pairs of POZ polymer conjugates containing cannabidiol (CBD) as the agent with the 2-propionate linker were prepared (POZ-CBD conjugates) with and without hydrophilic propionic acid pendent moieties.

The first pair of POZ-CBD conjugates contained six pendent CBD molecules with and without four pendent propionic acid groups. The second pair of POZ-CBD conjugates contained eight pendent CBD molecules with and without two pendent propionic acid groups. The structure of the POZ-CBD conjugates is shown below:

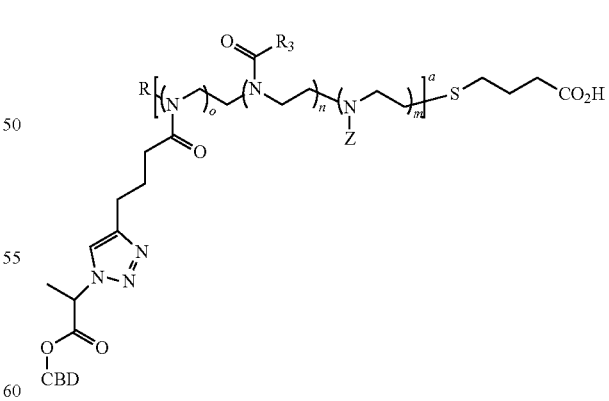

Wherein:
o is 6 for the first POZ-CBD conjugate pair or is 8 for the second POZ-CBD conjugate pair;
p is 190;
a is random;
R is H;

$R_3$ is —$CH_2CH_3$;

m is 4 for the first POZ-CBD conjugate pair or 2 for the second POZ-CBD conjugate pair; and Z is either

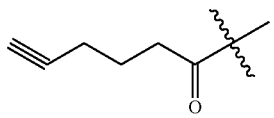 [SMILES: *C(=O)CCCC#C]

(when the POZ-CBD conjugate lacks a hydrophilic propionic acid group) or

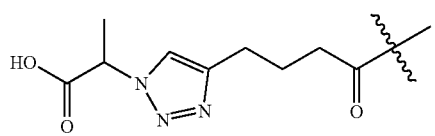 [SMILES: *C(=O)CCCc1cn(C(C)C(=O)O)nn1]

(when the POZ-CBD conjugate contains a hydrophilic propionic acid group).

Figure 2:
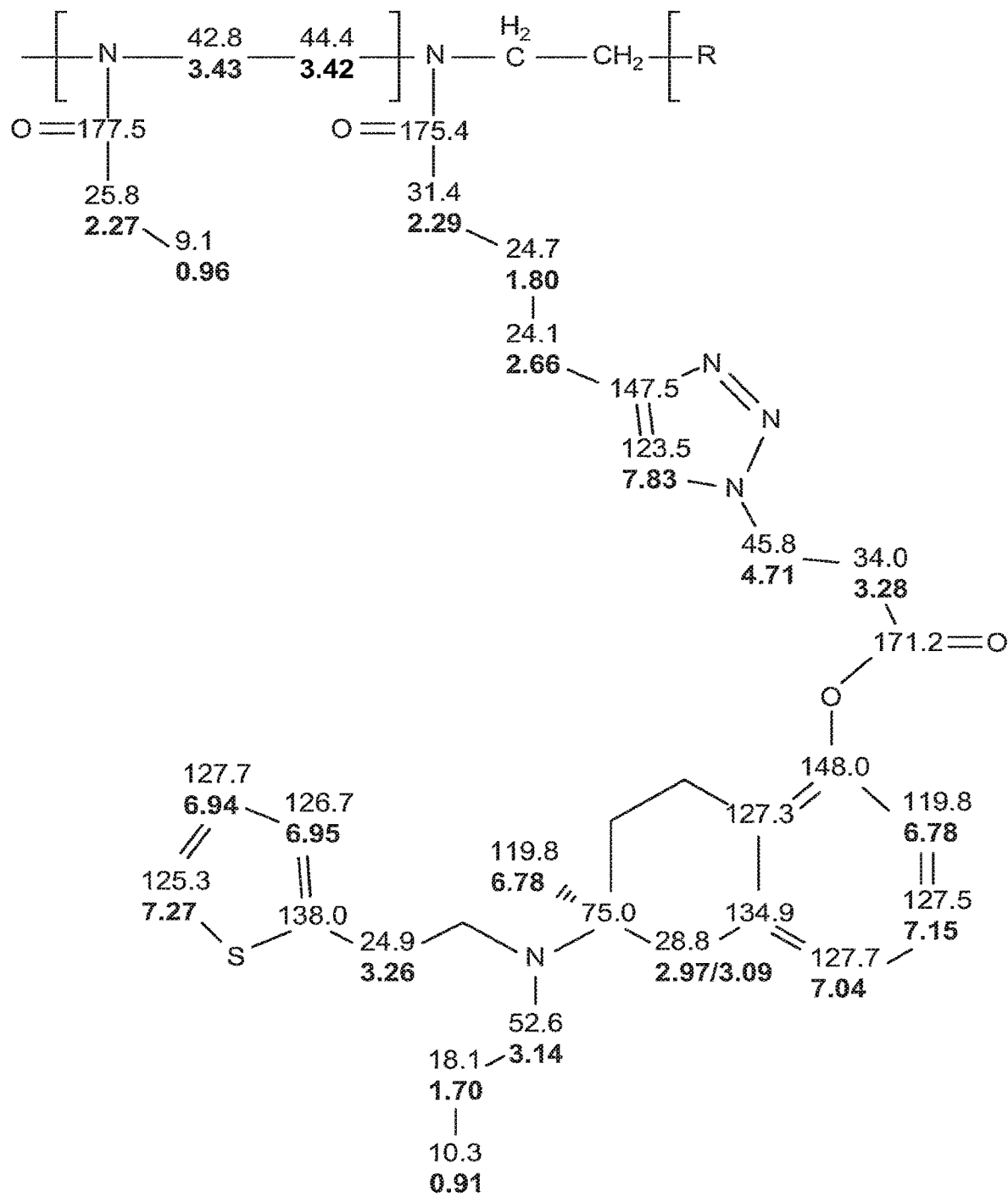
FIG. 2 shows assigned chemical shifts for the POZ conjugate structure with rotigotine attached to POZ.

The half-life ($t_{1/2}$) of each POZ-CBD conjugate was determined as described in the Methods section herein. The results are presented in FIG. 2 and the table below. FIG. 2 shows that in POZ-CBD conjugates with hydrophilic pendent moieties, the CBD molecule hydrolyzed faster from the POZ-CBD conjugate as compared to a POZ-CBD conjugate without hydrophilic moieties. The half-lives for each conjugate are shown in the table below:

| POZ-CBD Conjugate | $t_{1/2}$ (hours) |
| --- | --- |
| 6 CBD and 0 hydrophilic pendants | 64 |
| 6 CBD and 4 hydrophilic pendants | 54 |
| 8 CBD and 0 hydrophilic pendants | 87 |
| 8 CBD and 2 hydrophilic pendants | 74 |

For the POZ-CBD conjugates with 6 pendent CBD molecules, the presence of the hydrophilic pendent moieties decreased the $t_{1/2}$ from 64 hours to 54 hours indicating a more rapid hydrolysis of the CBD molecules from the POZ-CDB conjugate. The same increased hydrolysis rate was also seen for the POZ CDB conjugates with 8 pendent CBD molecules, where the presence of 2 hydrophilic pendent moieties decreased the $t_{1/2}$ from 87 hours to 74 hours, again indicating a more rapid hydrolysis of the CBD molecules from the POZ-CDB conjugate. Furthermore, as discussed above, the increased drug loading (from 6 to 8 CBD molecules) decreased hydrolysis rates. POZ-CBD conjugates with 8 pendent CBD molecules exhibited increased $t_{1/2}$ as compared to POZ-CBD conjugates with 6 pendent CBD molecules (both with and without the presence of hydrophilic pendants).

Example 4—the Presence of Hydrophilic PEG Pendent Moieties Increases Hydrolysis Rates To further investigate the role of hydrophilic pendent moieties on hydrolysis rates of an agent from a POZ polymer conjugate in vitro, POZ-CBD conjugates with and without hydrophilic propionic acid pendent moieties and polyethylene glycol (PEG$_7$-OH) were prepared. A different batch of female human plasma was used in this Example 4 as compared to Example 3. The measured half-lives for certain POZ-CBD conjugates used in both Examples were slightly different, but the trends remain the same. The slight difference is attributed to the different levels of butrylcholinesterase activity in blood [13].

A POZ-CBD conjugate with eight pendent CBD molecules was prepared along with POZ-CBD conjugates with eight pendent CBD molecules and either i) two pendent propionic acid groups; or ii) two PEG$_7$-OH pendent moieties. A POZ-CBD conjugate with ten pendent CBD molecules and no hydrophilic pendants was also prepared. The structure of the POZ-CBD conjugates is as shown in Example 5 with the exception that when the POZ-CBD conjugate contains a hydrophilic group, Z is either

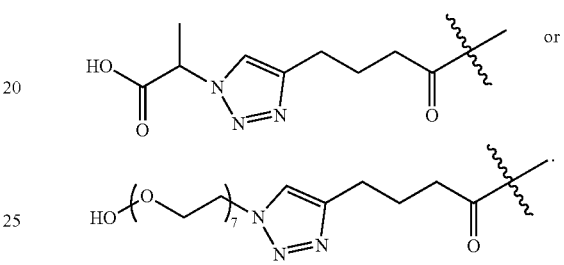

The $t_{1/2}$ of each POZ-CBD conjugate was determined as described in the Methods section herein. The results are presented in the table below and show that in POZ-CBD conjugates with hydrophilic pendent moieties, the CBD molecule hydrolyzed faster from the POZ-CBD conjugates as compared to POZ-CBD conjugates without hydrophilic pendent moieties. The half-lives for each conjugate are shown in the table below:

| POZ-CBD Conjugate | $t_{1/2}$ (hours) |
| --- | --- |
| 10 CBD and 0 hydrophilic pendants | 70 |
| 8 CBD and 0 hydrophilic pendants | 61 |
| 8 CBD and 2 hydrophilic propionic acid pendants | 45 |
| 8 CBD and 2 hydrophilic PEG$_7$-OH pendants | 40 |

For the POZ-CBD conjugates with 10 pendent CBD molecules, the $t_{1/2}$ was 70 hours, an increase over the $t_{1/2}$ of the POZ-CBD conjugate with 8 pendent CBD molecules.

For the POZ-CBD conjugates with 8 pendent CBD molecules, the presence of the hydrophilic propionic acid pendent moieties decreased the $t_{1/2}$ from 61 hours to 43 hours and the presence of the hydrophilic PEG$_7$-OH pendent moieties decreased the $t_{1/2}$ from 61 hours to 39 hours. These results again show a more rapid hydrolysis of the CBD molecules from the POZ-CDB conjugate. Furthermore, these results show that various hydrophilic pendent moieties are effective in increasing hydrolysis rates as pendent propionic acid and pendent PEG$_7$-OH groups were equally effective.

Example 5—the Presence of Hydrophilic Pendent Moieties on POZ Conjugates with Relatively Hydrophilic Drugs To further investigate the role of hydrophilic pendent moieties on hydrolysis rates of an agent from a POZ polymer conjugate in vitro, POZ polymer conjugates of buprenorphine (POZ-BUP) with the 3-propionate linker with and without hydrophilic propionic acid pendent moieties and polyethylene glycol (PEG$_7$-OH) were prepared.

POZ-BUP conjugates with eight pendent BUP molecules were prepared along with POZ-BUP conjugates with eight pendent BUP molecules and either i) two pendent propionic acid groups; or ii) two PEG$_7$-OH pendent moiety s. A POZ-BUP conjugate with ten pendent BUP molecules and no hydrophilic pendants was also prepared. The structure of the POZ-BUP conjugates is shown below, wherein o=10 or 8, p=190, a=random, R=H, R$_3$=—CH$_2$CH$_3$, m=2 or =0 (when the POZ-BUP conjugate did not contain hydrophilic pendants), and Z is either

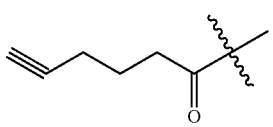 [SMILES: *C(=O)CCCC#C]

(when the POZ-BUP conjugate lacks a hydrophilic group) or

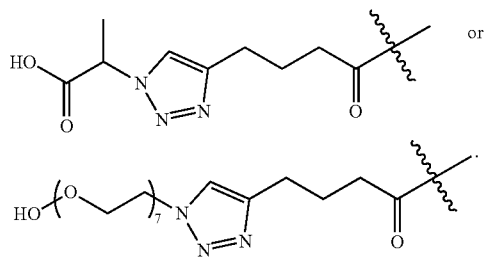

(when the POZ-BUP conjugate contains a hydrophilic group).

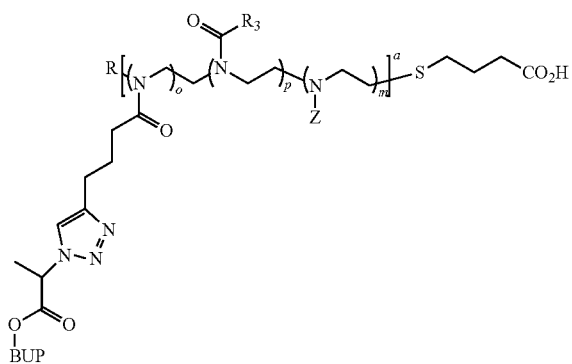

The t$_{1/2}$ of each POZ-BUP conjugate was determined as described in the Methods section herein. The results are presented in the table below.

| POZ-BUP Conjugate | t$_{1/2}$ (hours) |
|---|---|
| 10 BUP and 0 hydrophilic pendants | 17 |
| 8 BUP and 0 hydrophilic pendants | 11 |
| 8 BUP and 2 hydrophilic propionic acid pendants | 14 |
| 8 BUP and 2 hydrophilic PEG$_7$-OH pendants | 12 |

In this case, the human plasma hydrolysis rates showed the following pattern: 10 BUP pendants, 17 h; 8 BUP pendants, 11 h; 8 BUP and 2 propionic acid pendants, 14 h; and 8 BUP and 2 PEG$_7$-OH pendants, 12 h. Thus, the conjugates with pendent propionic acids and pendent PEGs have about the same hydrolysis rates, but they do not hydrolyze faster than the corresponding conjugate without these pendants. This result contrasts with the above results for the cannabidiol conjugate and would appear to be inconsistent with the folding hypothesis.

The buprenorphine and cannabidiol conjugates do show some interesting differences in physical properties. Buprenorphine is more hydrophilic than cannabidiol (Log P$_{oct/wat}$ values of 5.0 and 6.1, at 25° C., respectively), and it has been observed in this work that the buprenorphine conjugates are readily soluble in aqueous media while the cannabidiol conjugates dissolve slowly in buffer and are sparingly soluble in water. In addition, cannabidiol conjugates that are highly drug loaded are prone to "cloud point" behavior [14-16]. Based on these differences, it is not surprising that, the buprenorphine conjugates undergo plasma hydrolysis much more rapidly than cannabidiol conjugates, indicating that the buprenorphine conjugates are not tightly folded and are relatively open to enzymatic access.

Taking the foregoing into account, tightly folded conjugates, such as those formed with the relatively hydrophobic cannabidiol, will be responsive to introduction of inert hydrophilic groups, and will swell substantially upon introduction of these groups. On the other hand, loosely folded conjugates, such as those formed with the relatively hydrophilic buprenorphine, will not swell substantially upon introduction of hydrophilic pendants and thus will not show enhanced enzymatic hydrolysis upon introduction of these groups.

Example 6—Drug Loading Affects Hydrolysis Rates in Human and Rat Plasma

As discussed above, the amount of agent loaded on a POZ polymer conjugate is hypothesized to impact the hydrolysis rate of an agent from the POZ polymer conjugate, with higher drug-loading resulting in longer half-lives and lower drug loading resulting in shorter half-lives. The effect of ester linkage has been described previously [4,7], and as noted the plasma hydrolysis rates decrease in the order acetate>2-propionate>3-propionate. To determine the effect of drug loading on the hydrolysis rates of an agent from a POZ polymer conjugate in vitro, POZ polymer conjugates (PEOZ-20K-10P-COOH) were prepared with cannabidiol (POZ-CBD; drug loading 1.6% to 10.3%), rotigotine (POZ-ROT; drug loading 7.5% to 11.8%), d9-tetrahydrocannabinol (POZ-d9THC; drug loading 6.1% to 10.3%), buprenorphine (POZ-BUP; drug loading 11.3% to 15.5%), cannabigerol (POZ-CBG; drug loading 4.3% to 10.5%), and dexanabinol (POZ-DEX; drug loading 8.8%).

The Table below shows the t$_{1/2}$ values (determined as described in the Methods section) for the POZ-polymer conjugates in female human plasma at 37° C. As can be seen, the hydrolysis half-lives are longer for the more highly loaded conjugates. For the POZ-CBD conjugates with the 2-propionate linker, increasing drug loading from 1.6% to 8.9% increased the hydrolysis half-life from 10 hour to 87 hours. An increase in the hydrolysis half-life was also observed for the POZ-ROT conjugates (with the 3-propionate linker), where increasing drug loading from 7.5% to 11.8% increased the hydrolysis half-life from 17 hour to 76 hours, and POZ-d9THC conjugates (with the 3 propionate linker), where increasing drug loading from 6.1% to 10.3% increased the hydrolysis half-life from 49 hour to over 7 days.

There is a correlation between log P values and hydrolysis rates, with higher log P giving slower hydrolysis and longer half-lives. For example, with 3-propionate linker and 7.5% loading, rotigotine, with a log P of 4.9, undergoes hydrolysis faster (half-life 17 hours) than THC with a log P of 7.2 (half-life 90 hours), as predicted. However, there are some exceptions in the Table. For example, for 3-propionate linker and 6.1% loading, cannabidiol with log P of 6.1 has a half-life of 168 hours, while the more hydrophobic THC with log P of 7.0 has a half-life of 49 hours, counter to the general trend. While our folding hypothesis suggests that increasing log P should lead to a tighter core and a slower hydrolysis rate, it is also expected that changing the pendent drug changes more factors than log P. For example, even though the attachment point in all cases is a phenolic group on the drug and the ester linkages are the same, the size and shape of these molecules varies significantly. This variation would be expected to lead to different steric effects on folding and on esterase binding. Also, there are probably small but significant differences in electronic effects for the different drugs, and these also would affect hydrolysis rates for the ester linkages. Thus, it is not surprising that the correlation between drug log P and hydrolysis half-life is rough because of the difficulty in controlling steric and electronic effects among different drugs.

| Drug | Log P | % Loading | Hydrolysis half-life (hours) of different ester linkages | | |
|---|---|---|---|---|---|
| | | | acetate | 2-propionate | 3-propionate |
| Rotigotine | 4.9 | 7.5 | — | — | 17 |
| | | 7.9 | — | 8.2 | — |
| | | 8.5 | 2.5 | — | 31 |
| | | 9.7 | — | — | 52 |
| | | 10.7 | — | — | 60 |
| | | 11.8 | — | — | 76 |
| Buprenorphine | 5.0 | 11.3 | — | — | 18 |
| | | 15.5 | — | 5 | — |
| Cannabidiol | 6.1 | 1.6 | — | 10 | — |
| | | 3.6 | — | 16 | — |
| | | 6.1 | — | — | 168 |
| | | 6.3 | 11 | — | — |
| | | 6.6 | — | 37 | — |
| | | 8.9 | — | 87 | — |
| | | 10.3 | 37 | — | — |
| Δ⁹-THC | 7.0 | 6.1 | — | — | 49 |
| | | 6.6 | — | — | 65 |
| | | 7.5 | — | — | 90 |
| | | 10.2 | — | 10 | — |
| | | 10.3 | — | — | >7 days |
| Cannabigerol | 7.2 | 4.3 | — | — | 54 |
| | | 5.7 | — | — | >3 days |
| | | 7.6 | — | 14 | — |
| | | 10.5 | — | 17 | — |
| Dexanabinol | 7.6 | 8.8 | — | — | 210 |

Example 7—Drug Loading Affects Hydrolysis Rates In Vivo

The data in Example 6 showed that increasing the drug loading percentage decreased the hydrolysis half-life of five exemplary POZ conjugates in vitro. In general, one can expect that slowing plasma hydrolysis rate of a POZ-agent conjugate will lead to a longer in vivo plasma presence for the released agent. To determine the effect of drug loading on the hydrolysis rates and pharmacokinetics of an agent from a POZ conjugate in vivo, POZ conjugates (agent linked using a 3-propionate ester linkage) were prepared with cannabidiol (POZ-CBD; drug loading 2.8% or 7.1%) and rotigotine (POZ-ROT; drug loading 7.5% to 11.8%). The polymer conjugates were administered to the animals and the plasma samples analyzed for released agent as described in the Methods section.

FIG. 3 shows the plasma concentration of free rotigotine released from POZ-ROT conjugate after a single injection of POZ-ROT at drug loading percentages of 7.5%, 9.7%, and 11.8%. As can be seen in FIG. 3, the POZ-ROT conjugate at 7.5% drug loading provided a higher initial concertation of free rotigotine (as compared to POZ-ROT conjugates at 9.7% and 11.8% drug loading) between days 1 to 3, after which the concentration decreased from days 3 to 5. This indicates that rotigotine was released faster from the POZ-ROT conjugate at 7.5% drug loading (i.e., had a shorter $t_{1/2}$) as compared to the POZ-ROT conjugates at 9.7% and 11.8% drug loading. The POZ-ROT conjugate at 9.7% and 11.8% drug loading provided lower initial concertation of free rotigotine (as compared to POZ-ROT conjugates at 7.5% drug loading) between days 1 to 3 but maintained higher concentration from days 3 to 5. This indicates that rotigotine was released slower from the POZ-ROT conjugate at 9.7% and 11.8% drug loading (i.e., had a longer $t_{1/2}$) as compared to the POZ-ROT conjugates at 7.5% drug loading. These results are consistent with the data from Example 7 showing that the POZ-ROT conjugate at 7.5% drug loading had a shorter $t_{1/2}$ as compared to the POZ-ROT conjugate at 11.8% drug loading.

FIG. 4 shows the plasma concentration of free cannabidiol released from POZ-CBD conjugate after a single injection of POZ-CBD at drug loading percentages of 2.8 and 7.1%. As can be seen in FIG. 4, the POZ-CBD conjugate at 2.8% drug loading provided a higher initial peak concertation of free cannabidiol between days 1 and 2 (as compared to POZ-CBD conjugate at 7.1% drug loading), after which the concentration decreased from days 2 to 14. This indicates that cannabidiol was released faster from the POZ-CBD conjugate at 2.8% drug loading (i.e., had a shorter $t_{1/2}$) as compared to the POZ-CBD conjugates at 7.1% drug loading. The POZ-CBD conjugate at 7.1% drug loading provided lower initial concertation of free cannabidiol between days 1 and 2 (as compared to POZ-CBD conjugates at 2.8% drug loading), but maintained higher concentration from days 3 to 14. This indicates that cannabidiol was released slower from the POZ-CBD conjugate at 7.1% drug loading (i.e., had a longer $t_{1/2}$) as compared to the POZ-CBD conjugates at 2.8% drug loading. These results are consistent with the data from Example 7 showing that the POZ-CBD conjugates at lower drug loading percentages had shorter $t_{1/2}$ values as compared to the POZ-CBD conjugates with higher drug loading percentages.

Example 8—POZ Polymer Molecular Weight Effects on Circulation Lifetime In Vivo As discussed above, the POZ polymer portion of the POZ conjugate is hypothesized to impact the hydrolysis rate of an agent from the POZ conjugate, with higher molecular weight POZ polymer portions resulting in longer half-lives and lower molecular weight POZ polymer portions resulting in shorter half-lives. It is also of interest to determine the effect of POZ molecular weight on circulation lifetime in vivo. POZ conjugates of 10, 20, 30, 40, and 60 kD were prepared with the fluorescent dye cyanine-5 attached via a non-degradable linkage. The labeled POZ conjugates were injected intravenously and subcutaneously into male rats and the blood concentration of cyanine-5 was monitored over time via fluorescence spectrophotometry as described in the Methods section.

The results are shown in FIGS. 7 and 8. As can be seen from FIGS. 7 and 8, the expected molecular weight dependent clearance pattern is observed [Yamaoka et al., J. Pharm Sci., 83, 601-606, 1994]. The 10 kD POZ-cyanine concentration falls below the level of detection after three days, while the 40 and 60 kD POZ-cyanine concentrations are still present at significant levels after 28 days when the experiment was terminated. The 20 and 30 kDa POZ polymers gave steady blood levels over 14 and 21 days, respectively. The cut-off for glomerular filtration of POZ was reported to be around 40 kD (Wyffels et al., J. Cont. Rel., 235, 63-71 (2016).

Example 9—Tuning Pharmacokinetics of POZ-Conjugates In Vivo

The previous Examples have shown that POZ-drug in-vitro hydrolysis rates can be varied (i.e., tuned) to produce a specific release profile by changing the linker, by changing loading % of drug, and by adding inert hydrophilic pendent moieties. To explore the effects of these parameters in vivo, several POZ conjugates were studied. Pharmacokinetics in vivo is complicated by many factors, including, but not limited to, renal and hepatic clearance. In many instances a once-a-week injection with a flat steady-state PK profile would be of great utility, especially for drugs having short half-lives in-vivo.

In general, one can expect that slow in-vitro plasma hydrolysis rates of an agent from a POZ conjugate will lead to a longer in-vivo plasma presence for the released drug and this is observed in the experiments in this Example. FIG. 9 shows the pharmacokinetic (PK) profile of rotigotine in rats following a single SC injection of rotigotine and POZ-rotigotine (structure 1) with acetyl (drug loading 10.9%) and 3-propionyl (drug loading 13.3%) ester linkages. The POZ-ROT conjugates were administered at a dose of 1.6 mg/kg and free rotigotine was administered at a dose of 0.5 mg/kg. As shown in Example 7, the 3-propionate ester undergoes plasma hydrolysis substantially more slowly than the acetate ester, and as expected the in-vivo steady-state PK profile of FIG. 9 shows that the 3-propionate ester has a longer blood residence time and less of an initial Cmax "burst effect" than the acetate ester. An injection of rotigotine alone, clears the body in less than 24 hours.

FIG. 10 shows the pharmacokinetic (PK) profile of buprenorphine in male monkeys following a single SC injection of POZ-BUP with 2-propionyl (drug loading 11.2%) and 3-propionyl (drug loading 13.3%) ester linkages. The POZ-ROT conjugates were administered at a dose of 1.5 mg/kg. As expected, the in-vivo steady-state PK profile of FIG. 10 shows that the 3-propionate ester has a longer blood residence time and less of an initial Cmax "burst effect" than the acetate ester. Plasma levels for buprenorphine are virtually flat for 4-5 days in both rat and monkey, at the dose of 1.5 mg/kg (based on buprenorphine equivalents). Such a profile indicates that POZ conjugates are suitable compounds for a once-a-week subcutaneous injection to treat post-operative pain.

Example 10—the Presence of Hydrophobic Octyl Pendent Moieties Decreases Hydrolysis Rates To study the effect of hydrophobic pendent moieties on plasma hydrolysis rates three different POZ conjugates were prepared, all having sufficient pendent pentynyl groups for linking of the agent to the POZ conjugate: (1) PEOZ-20K with 10 buprenorphine molecules and no hydrophobic pendent moieties; (2) PEOZ-20K with 8 buprenorphine molecules and no hydrophobic pendent moieties; and (3) PEOZ-20K with 8 buprenorphine molecules and 2 hydrophobic octyl (C8) pendent moieties. Hydrolysis rates were determined in female human plasma at 37 degrees and the half-life of each POZ conjugate was determined.

The results were as follows: PEOZ-20K with 10 buprenorphine molecules and no hydrophobic pendent moieties (half-life 16 h); PEOZ-20K with 8 buprenorphine molecules and no hydrophobic pendent moieties (half-life 12 h); and PEOZ-20K with 8 buprenorphine molecules and 2 hydrophobic pendent moieties (half-life 15 h). These results confirm the results of earlier examples showing that increasing the loading percentage of an agent decreases the release rate of the agent from the POZ conjugate. In addition, these results show the presence of a hydrophobic pendent moiety decreases the hydrolysis rate of the agent from the POZ polymer portion as expected. Therefore, hydrophobic pendent moieties may be used to decrease the release rate of an agent from a POZ-conjugate and to select a desired release profile an agent from a POZ conjugate.

Example 11—Increasing the Molecular Weight of the POZ Polymer Portion Decreases the Hydrolysis Rate of an Agent from POZ Conjugates To study the effect of the molecular weight of the POZ polymer portion on plasma hydrolysis rates two different POZ conjugates were prepared, all having sufficient pendent pentynyl groups for linking of the agent to the POZ conjugate: (1) PEOZ-20K and (2) PEOZ-8K. CBD was conjugated to POZ polymer portion via an acetate linker to give 8.7% drug loading for each POZ conjugate. Hydrolysis rates were determined in female human plasma at 37 degrees and the half-life of each POZ conjugate was determined.

The results were as follows: POZ-8K (half-life 5 h) and POZ-20K (half-life 11 h). These results confirm that increasing the molecular weight of the POZ polymer portion decreases the hydrolysis rate of the agent from the POZ polymer portion as expected. Therefore, modulating the molecular weight of the POZ polymer portion may be used to increase or decrease the release rate of an agent from a POZ-conjugate and to select a desired release profile an agent from a POZ conjugate.

Example 12—Increasing the Hydrophobic Character of the Pendent Groups on the POZ Polymer Portion Decreases the Hydrolysis Rate of an Agent from POZ Conjugates To study the effect of the hydrophobic character of the pendent groups on the POZ polymer portion on plasma hydrolysis rates two different polyoxazolines were prepared, all having sufficient pendent pentynyl groups for linking of the agent to the POZ conjugate: (1) PEOZ-20K, and (2) a copolymer of polyoxazoline with 15% methyl oxazoline and 85% ethyl oxazoline (Co-POZ-20K). CBD was conjugated to POZ polymer portion via an acetate linker to give 8.7% drug loading for each POZ conjugate. Hydrolysis rates were determined in female human plasma at 37 degrees and the half-life of each POZ conjugate was determined. POZ conjugate 1 has a more hydrophobic character as all the pendent groups (approximately 190) are the more hydrophobic ethyl groups wherein only 85% of the pendent groups (approximately 160) are ethyl groups with the remainder being methyl.

The results were as follows: CoPOZ-20K (half-life 8 h), and POZ-20K (half-life 11 h). These results confirm that increasing the hydrophobic character of the pendent groups on the POZ polymer portion decreases the hydrolysis rate of the agent from the POZ polymer portion as expected. Therefore, modulating the hydrophobic character of the pendent groups on the POZ polymer portion may be used to increase or decrease the release rate of an agent from a POZ-conjugate and to select a desired release profile an agent from a POZ conjugate.

What is claimed:

1. A polyoxazoline (POZ) conjugate comprising:
a water-soluble POZ polymer comprising one or more inert pendent groups having hydrophilic character; and
an agent linked to the water-soluble POZ polymer by a physiologically degradable linkage, wherein a release rate of the agent from the POZ conjugate is modulated based on the hydrophilic character of the inert pendent groups and a loading percentage and/or hydrophobic character of the agent.

2. The POZ conjugate of claim 1, wherein the agent is a phytocannabinoid, a dopamine agonist, an anticholinergic, a monoamine oxidase-B inhibitor, a catechol-O-methyl transferase (COMT) inhibitor, an adenosine $A_{2A}$ receptor antagonist, or a GABA-uptake inhibitor.

3. The POZ conjugate of claim 2, wherein the phytocannabinoid is selected from the group consisting of: cannabidiol, cannabigerol, cannabigerolic acid, cannabidiolic acid, cannabidiolmonomethylether, cannabidiol-C4, cannabidarinic acid, cannabidivarin, cannabigerol propyl variant, tetrahydrocannabivarin, $\Delta^9$-THC, ajulemic acid, and dexanabinol.

4. The POZ conjugate of claim 2, wherein the dopamine agonist is selected from the group consisting of: apomorphine, arbutamine, carbidopa, dobutamine, dopamine, entacapone, epinephrine, fenoldopam, isoetharine, isoproterenol, levodopa, levonordefrin, masaprocol, methyldopa, methyldopate, norepinephrine, protokylol, tolcapone, (r)-(+)-fenoldopam, rotigotine, pramipexole, quinagolide, 5-OH-DPAT, ropinirole, pergolide, cabergoline, and bromocriptine.

5. The POZ conjugate of claim 2, wherein the anticholinergic is selected from the group consisting of: trihexyphenidyl, biperidin and hyoscyamine.

6. The POZ conjugate of claim 2, wherein the monoamine oxidase-B inhibitor is selected from the group consisting of: seligiline and rasagiline.

7. The POZ conjugate of claim 2, wherein the COMT inhibitor is selected from the group consisting of: tolcapone and entacapone.

8. The POZ conjugate of claim 2, wherein the adenosine $A_{2A}$ receptor antagonist is selected from the group consisting of: preladenant, theophylline and istradefylline.

9. The POZ conjugate of claim 2, wherein the GABA-uptake inhibitor is selected from the group consisting of: tiagabine and nipecotic acid.

10. The POZ conjugate of claim 1, wherein the release rate of the agent from the POZ conjugate is further modulated based on the molecular weight for the POZ polymer portion.

11. The POZ conjugate of claim 1, wherein the inert pendent groups are linked to the POZ polymer by a non-degradable linkage.

12. The POZ conjugate of claim 1, having the structure

A is the agent;
R is hydrogen, unsubstituted alkyl or substituted alkyl;
$R_1$ is an inert pendant group, wherein the inert pendant group comprises one or more hydrophilic pendent moieties;
$L_1$ is a linking group linking $R_1$ to the POZ polymer or is absent;
$R_2$ is a pendent moiety comprising the physiologically degradable linkage linking the POZ polymer and A;
X is a pendant group;
T is a terminating group;
a is ran, which indicates a random copolymer or block which indicates a block copolymer;
m is an integer from 1 to 50;
n is an integer from 0 to 1000; and
o is an integer from 1 to 50.

13. A polyoxazoline (POZ) conjugate comprising:
a water-soluble POZ polymer;
an inert pendant moiety containing a hydrophilic portion linked to the POZ polymer; and
an agent linked to the water-soluble POZ polymer by a physiologically degradable linkage, wherein a release rate of the agent from the POZ conjugate is modulated based on the hydrophilic portion of the pendant moiety and a loading percentage of the agent.

14. The POZ conjugate of claim 13, wherein the agent is a phytocannabinoid, a dopamine agonist, an anticholinergic, a monoamine oxidase-B inhibitor, a catechol-O-methyl transferase (COMT) inhibitor, an adenosine $A_{2A}$ receptor antagonist, or a GABA-uptake inhibitor.

15. The POZ conjugate of claim 14, wherein the phytocannabinoid is selected from the group consisting of: cannabidiol, cannabigerol, cannabigerolic acid, cannabidiolic acid, cannabidiolmonomethylether, cannabidiol-C4, cannabidarinic acid, cannabidivarin, cannabigerol propyl variant, tetrahydrocannabivarin, $\Delta^9$-THC, ajulemic acid, and dexanabinol.

16. The POZ conjugate of claim 13, having the structure

A is the agent;
R is hydrogen, unsubstituted alkyl or substituted alkyl;
$R_1$ is the inert pendant moiety;
$L_1$ is a linking group linking $R_1$ to the POZ polymer or is absent;
$R_2$ is a pendent moiety comprising the physiologically degradable linkage linking the POZ polymer and A;
X is a pendant group;
T is a terminating group;
a is ran, which indicates a random copolymer or block which indicates a block copolymer;
m is an integer from 1 to 50;
n is an integer from 0 to 1000; and
o is an integer from 1 to 50.

17. A method for modulating the release rate of an agent from a polyoxazoline (POZ) conjugate comprising:
linking an agent to a water-soluble POZ polymer by a physiologically degradable linkage to form a POZ conjugate, wherein the POZ conjugate has a loading percentage of the agent, and wherein the water-soluble POZ polymer comprises one or more inert pendent groups with hydrophilic or hydrophobic character; and modulating the release rate of the agent from the POZ conjugate through selection of the hydrophilic or hydrophobic character and the loading percentage of the agent.

18. The method of claim 17, wherein the loading percentage is from 1.6% to 10.3% (w/w agent to POZ polymer).

19. The method of claim 17, wherein the loading percentage is from 1.6% to 8.9% (w/w agent to POZ polymer).

20. The method of claim 17, wherein the POZ conjugate has the structure:

$$R-\{[N(CO-L_1-R_1)CH_2CH_2]_m-[N(COR_2-A)CH_2CH_2]_o-[N(COX)CH_2CH_2]_n\}_a-T$$

wherein:
A is the agent;
R is hydrogen, unsubstituted alkyl or substituted alkyl;
$R_1$ is an inert hydrophilic pendent group;
$L_1$ is a linking group linking $R_1$ to the POZ polymer or is absent;
$R_2$ is a pendent moiety comprising the physiologically degradable linkage linking the POZ polymer and A;
X is a pendant group;
T is a terminating group;
a is ran that indicates a random copolymer or block that indicates a block copolymer;
m is an integer from 1 to 50;
n is an integer from 0 to 1000; and
o is an integer from 1 to 50.

* * * * *